US007355001B2

(12) United States Patent
Nakanishi et al.

(10) Patent No.: US 7,355,001 B2
(45) Date of Patent: Apr. 8, 2008

(54) ORGANIC ANION TRANSPORT PROTEIN TCH229

(75) Inventors: Atsushi Nakanishi, Tsukuba (JP); Yukiko Hikichi, Tsukuba (JP); Yumiko Uno, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 264 days.

(21) Appl. No.: 10/506,308

(22) PCT Filed: Mar. 5, 2003

(86) PCT No.: PCT/JP03/02564

§ 371 (c)(1),
(2), (4) Date: Sep. 1, 2004

(87) PCT Pub. No.: WO03/074702

PCT Pub. Date: Sep. 12, 2003

(65) Prior Publication Data

US 2005/0233323 A1    Oct. 20, 2005

(30) Foreign Application Priority Data

Mar. 6, 2002 (JP) ............................. 2002-061133
Apr. 1, 2002 (JP) ............................. 2002-098852
Jun. 25, 2002 (JP) ............................. 2002-184883

(51) Int. Cl.
    *C07K 14/00* (2006.01)
(52) U.S. Cl. ..................................................... 530/350
(58) Field of Classification Search ...................... None
    See application file for complete search history.

(56) References Cited

U.S. PATENT DOCUMENTS 6,972,187 B2 * 12/2005 Curtis et al. ................ 435/69.1

FOREIGN PATENT DOCUMENTS

WO         WO 01/54477 A2        8/2001

OTHER PUBLICATIONS

Skolnick et al. Trends in Biotech. 2000. vol. 34, p. 34-39.*
Bork P. Genome Research. 2000. vol. 10, p. 398-400.*
Doerks et al. Trends in Genetics. 1998. vol. 14, p. 248-250.*
Smith et al. Nature Biotechnology. 1997. vol. 15, p. 1222-1223.*
Brenner S.E. Trends in Genetics. 1999. vol. 15, p. 132-133.*
Bork et al. Trends in Genetics. 1996. vol. 12, p. 425-427.*
Mikkaichi T, et al. Isolation and characterization of a digoxin transporter and its rat homologue expressed in the kidney. Proc. Natl. Acad. Sci. USA. 2004. vol. 101, pp. 3569-3574.*
Y. Okazaki, et al., "Analysis of the Mouse Transcriptome Based on Functional Annotation of 60,770 Full-Length cDNAs", Nature, (2002), pp. 563-573, vol. 420, No. 6915.

S. Kondo, et al., "Computational Analysis of Full-Length Mouse cDNAs Compared with Human Genome Sequences", Mammalian Genome, (2001), pp. 673-677, vol. 12, No. 9.
H. Konno, et al., "Computer-Based Methods for the Mouse Full-Length cDNA Encyclopedia: Real-Time Sequence Clustering for Construction of a Nonredundant cDNA Library", Genome Research, (2001), pp. 281-289, vol. 11, No. 2.
H. Kusuhara, et al., "Role of Transporters in the Tissue-Selective Distribution and Elimination of Drugs: Transporters in the Liver, Small Intestine, Brain and Kidney", Journal of Controlled Release, (2002), pp. 43-54, vol. 78, Nos. 1-3.
I. Tamai, et al., "Molecular Identification and Characterization of Novel Members of the Human Organic Anion Transporter (OATP) Family", Biochemical and Biophysical Research Communications, (2000), pp. 251-260, vol. 273.
B. Hagenbuch, et al., "The Superfamily of Organic Anion Transporting Polypeptides", Biochim. Biophys. Acta (2003), pp. 1-18, vol. 1609, No. 1.GenBank#NM030958.
R.L. Strausberg, et al., "Generation and Initial Analysis of More than 15,000 Full-Length Human and Mouse CDNA Sequences", Proc. Natl. Acad. Sci. USA (2002), pp. 16899-16903, vol. 99, No. 26., GenBank#NP076397.
K. Fujiwara, et al., "Identification of Thyroid Hormone Transporters in Humans: Different Molecules are Involved in a Tissue-Specific Manner", (2001), pp. 2005-2012, vol. 142, No. 5.
Database EMBL, Online, "Mus Musculus Adult Male Hippocampus cDNA", (2001), XP002331333, retrieved from EBI, Database accession No. BB653181.
Database EMBL, Online, "vl58a09.s1 Knowles Solter Mouse 2 Cell Mus Musculus cDNA Clone Image:976408", (1997), XP002331334, retrieved from EBI, database accession No. AA619778.
Database EMBL, Online, "H3089D08-5 NIA Mouse 15K cDNA Clone set Mus Musculus cDNA Clone", (2001), XP002331335, retrieved from EBI, database accession No. BG083458.

* cited by examiner

*Primary Examiner*—Robert Landsman
*Assistant Examiner*—Bruce D. Hissong
(74) *Attorney, Agent, or Firm*—Wenderoth, Lind & Ponack, L.L.P.

(57) ABSTRACT

Novel proteins of the present invention that have an organic anion transport activity are useful as, for example, a diagnostic marker for kidney diseases, liver diseases, pancreas diseases, immunological diseases associated with thymus failures, reproductive diseases, digestive diseases, spleen diseases, cancer, respiratory diseases, myelitis, diabetes, hypertension, reperfusion injury following ischemia, retinitis, central nervous diseases, skin diseases, thyroid hormone-associated diseases, etc. Compounds that promote or inhibit the activity of the above protein, which are obtained by a screening method using the protein, can be used as, for example, prophylactic/therapeutic agents for the above-described diseases.

3 Claims, 17 Drawing Sheets

```
TCH229   MKSA KGIEN LAFVPSSP DIL RR L SASPSQ I EVSA L S S D P Q REN SQPQ E LQ  50
mTCH229  MQGS KGIEN PAFVPSSP GTP RR A SASPSQ V EVSA V A S R N Q NGG SQPRE - -  48

TCH229   KPQ EPQKS P EPS L P S A P P NV S EE KLRSLS L S E FEEG S Y GWR N FHPQCLQR 100
mTCH229  - SE EPQKS T EPS P P S S N P PA S DE P - PGSQ L S E LEEG P C GWR G FHPQCLQR  96
                                                TM1
TCH229   CNTP G GFLLHYCLLA V TQGIVVNGLVNISIST V EKRYEMKSSLTGLISSS 150
mTCH229  CNTP Q GFLLHYCLLA L TQGIVVNGLVNISIST I EKRYEMKSSLTGLISSS 146
              TM2                                          TM3
TCH229   YDISFC L LSLFVSFFGERGHKPRWLAFA A FMIGLGALVFSLP Q FFSG E Y K 200
mTCH229  YDISFC V LSLFVSFFGERGHKPRWLAFA S FMIGLGALVFSLP H FFSG R Y E 196
                                              TM4
TCH229   LGS L FEDTC V T T RNST S C TSSTS S LSNY L Y VF I LGQLLLG A GGTPLYTLG 250
mTCH229  LGS I FEDTC L T - RNST R C SSSTS L LSNY F Y VF V LGQLLLG T GGTPLYTLG 245
                                                        TM5
TCH229   TAF L DDSVPTHKSSLYIG T GY A MSILGPAIGYVLGGQLLT I YID V AMG E S 300
mTCH229  TAF I DDSVPTHKSSLYIG I GY S MSILGPAIGYVLGGQLLT M YID I AMG Q S 295
                                        TM6
TCH229   T D V TEDDPRWLGAWWIGFLL S W IFAWSLI I PFSCFPKHLPGTA E IQAGKT 350
mTCH229  S D L TEDDPRWLGAWWIGFLL A W LFAWSLI M PFSCFPKHLPGTA K IQAGKT 345
                                                                    TM7
TCH229   SQ A HQ S NS NA - - - - D VK FGKSIKDFP A A L KNLM K N A VF M CLVLST S SEAL 396
mTCH229  SQ T HQ N NS TSFQHT D EN FGKSIKDFP T A V KNLM R N T VF I CLVLST T SEAL 395
                                                               TM8
TCH229   ITTGFATFLPKFIENQFGLTSSFAATLGGAVLIPGAALGQILGG F LVSKF 446
mTCH229  ITTGFATFLPKFIENQFGLTSSFAATLGGAVLIPGAALGQILGG V LVSKF 445
                            TM9
TCH229   R M TCKNTMKFAL F TSGVAL T L SFVF M YAKCENEPFAGVSESYNGTGE L GN 496
mTCH229  K M KCKNTMKFAL C TSGVAL V L SFVF I YAKCENEPFAGVSESYNGTGE M GN 495

TCH229   L I APCNANCNC S RSYYYP V CG - D GV QYFSPCFAGC S NP V A HRKPKVYYNC 545
mTCH229  L T APCNANCNC L RSYYYP L CG S D GI QYFSPCFAGC L NS V S NRKPKVYYNC 545
                                                             TM10
TCH229   SCIER K TE ITSTAE T FG FEAKAGKC E T HC A K LPIFL C IFFIV I IFTFMAG 595
mTCH229  SCIER - - K ITSTAE S TD FEAKAGKC R T RC S N LPIFL G IFFI T V IFTFMAG 593
                                               *         TM11
TCH229   TPITVSILRCVNHR Q RSLALG I QFM V LRLLGTIPGPIIFG F T IDSTC I LW 645
mTCH229  TPITVSILRCVNHR H RSLALG V QFM L LRLLGTIPGPIIFG V I IDSTC V LW 643
                                                  TM12
TCH229   D I N D CGIKGACWIYDNIKMAHMLVAISVTCKVIT M FFNG F A I FLYKPPP S 695
mTCH229  D V N E CGIKGACWIYDNIKMAHMLVAISVTCKVIT I FFNG L A I VLYKPPP P 693

TCH229   A T D VSF HKE N AV V TNVLAE Q DLN K IVK E G .                              725
mTCH229  G T E VSF QSQ N VI V STISVE E DLD K AEN E G .                              723
```

Fig. 7

```
TCH229     MKSAKGIENLAFVPSSPDILRRLSASPSQIEVSALSSDPQRENSQ  45
rTCH229No.1 MQGSKGVENPAFVPSSPDTPRRASASPSQVEVSAVASRNQNGGSQ  45
rTCH229No.2 MQGSKGVENPAFVPSSPDTPRRASASPSQVEVSAVASRNQNGGSQ  45

TCH229     PQELQKPQEPQKSPEPSLPSAPPNVSEEKLRSLSLSEFEEGSYGW  90
rTCH229No.1 PRE---SEDPQKSTEPSPPSSTLPASDEP-PGSQLSELEEGPCGW  86
rTCH229No.2 PRD---SEDPQKSTEPSPPSSTLPASDEP-PGSQLRELEEGPCGW  86
                                                      TM1
TCH229     RNFHPQCLQRCNTPGGFLLHYCLLAVTQGIVVNGLVNISISTVEK 135
rTCH229No.1 RNFHPQCLQRCNNPKGFLLHYCLLALTQGIVVNGLVNISISTIEK 131
rTCH229No.2 RNFHPQCLQRCNNPKGFLLHYCLLALTQGIVVNGLVNISISTIEK 131
                                           TM2
TCH229     RYEMKSSLTGLISSSYDISFCLLSLFVSFFGERGHKPRWLAFAAF 180
rTCH229No.1 RYEMKSSLTGLISSSYDISFCVLSLFVSFFGERGHKPRWLAFASF 176
rTCH229No.2 RYEMKSSLTGLISSSYDISFCVLSLFVSFFGERGHKPRWLAFASF 176
                   TM3
TCH229     MIGLGALVFSLPQFFSGEYKLGSLFEDTCVTTRNSTSCTSSTSSL 225
rTCH229No.1 MIGLGALVFSLPHFFSGRYELGTIFEDTCLT-RNSTRCASSTSLL 220
rTCH229No.2 MIGLGALVFSLPHFFSGRYELGTIFEDTCLT-RNSTRCASSTSLL 220
                         TM4
TCH229     SNYLYVFILGQLLLGAGGTPLYTLGTAFLDDSVPTHKSSLYIGTG 270
rTCH229No.1 SNYFYVFVLGQLLLGTGGTPLYTLGTAFIDDSVPTHKSSLYIGIG 265
rTCH229No.2 SNYFYVFVLGQLLLGTGGTPLYTLGTAFIDDSVPTHKSSLYIGIG 265
                            TM5
TCH229     YAMSILGPAIGYVLGGQLLTIYIDVAMGESTDVTEDDPRWLGAWW 315
rTCH229No.1 YSMSILGPAIGYVLGGQLLTMYIDVAMGQSSDLTEDDPRWLGAWW 310
rTCH229No.2 YSMSILGPAIGYVLGGQLLTMYIDVAMGQSSDLTEDDPRWLGAWW 310
                        TM6
TCH229     IGFLLSWIFAWSLIIPFSCFPKHLPGTAEIQAGKTSQAHQSNSNA 360
rTCH229No.1 IGFLLAWLFAWSLIMPFSCFPKHLPGTAKIQAGKTSQTHQNNSTS 355
rTCH229No.2 IGFLLAWLFAWSLIMPFSCFPKHLPGTAKIQAGKTSQTHQNNSTS 355
                                                  TM7
TCH229     ----DVKFGKSIKDFPAALKNLMKNAVFMCLVLSTSSEALITTGF 401
rTCH229No.1 FQHMDENFGKSIKDFPTAVKNLMRNTVFICLVLSTTSEALVTTGF 400
rTCH229No.2 FQHMDENFGKSIKDFPTAVKNLMRNTVFICLVLSTTSEALVTTGF 400
                                          TM8
TCH229     ATFLPKFIENQFGLTSSFAATLGGAVLIPGAALGQILGGFLVSKF 446
rTCH229No.1 ATFLPKFIENQFGLTSSIAATLGGAVLIPGAALGQILGGVLVSKF 445
rTCH229No.2 ATFLPKFIENQFGLTSSFAATLGGAVLIPGAALGQILGGVLVSKF 445
                             TM9
TCH229     RMTCKNTMKFALFTSGVALTLSFVFMYAKCENEPFAGVSESYNGT 491
rTCH229No.1 KMKCKNTMKFALCTSGVALMLSFVFIYAKCENGPFAGVSESYNGT 490
rTCH229No.2 KMKCKNTMKFALCTSGVALMLSFVFIYAKCENGPFAGVSESYNGT 490
```

Fig. 8

```
TCH229      GELGNLIAPCNANCNCSRSYYYPVCG-DGVQYFSPCFAGCSNPVA 535
rTCH229No.1 GEMGNLTAPCNANCNCLRSYYYPLCGSDGVQYFSPCFAGCLNSVS 535
rTCH229No.2 GEMGNLTAPCNANCNCLRSYYYPLCGSDGVQYFSPCFAGCLNSVS 535

TCH229      HRKPKVYYNCSCIERKTEITSTAETFGFEAKAGKCETHCAKLPIF 580
rTCH229No.1 NRKPKAYYNCSCIERKVDITSTAESPDFEARAGKCKTQCSNLPIF 580
rTCH229No.2 NRKPKAYYNCSCIERKVDITSTAESPDFEARAGKCKTQCSNLPIF 580
                         TM10                              *
TCH229      LCIFFIVIIFTFMAGTPITVSILRCVNHRQRSLALGIQFMVLRLL 625
rTCH229No.1 LGIFFITVIFTFMAGTPITVSILRCVNHRQRSLALGVQFMLLRLL 625
rTCH229No.2 LGIFFITVIFTFMAGTPITVSILRCVNHRQRSLALGVQFMLLRLL 625
                    TM11
TCH229      GTIPGPIIFGFTIDSTCILWDINDCGIKGACWIYDNIKMAHMLVA 670
rTCH229No.1 GTIPGPIIFGVTIDSTCVLWDINECGTKGACWIYDNIRMAHMLVA 670
rTCH229No.2 GTIPGPIIFGVTIDSTCVLWDINECGTKGACWIYDNIRMAHMLVA 670
                              TM12
TCH229      ISVTCKVITMFFNGFAIFLYKPPPSATDVSFHKENAVVTNVLAEQ 715
rTCH229No.1 ISVTCKVITIFFNGLAIVLYKPPPPGTEVSFQSQNVVVSTITVEE 715
rTCH229No.2 ISVTCKVITIFFNGLAIVLYKPPPPGTEVSFQSQNVVVSTITVEE 715

TCH229      DLNKIVKEG. 725
rTCH229No.1 DLNKIENEG. 725
rTCH229No.2 DLNKIENEG. 725
```

ORGANIC ANION TRANSPORT PROTEIN TCH229

This application is the National Phase filing of International Patent Application No. PCT/JP03/02564, filed Mar. 5, 2003.

TECHNICAL FIELD

The present invention provides novel organic anion transporter (oatp/LST) proteins, DNAs encoding these proteins, a method of screening compounds that promote or inhibit the activities of these proteins, compounds obtained by the screening method, etc.

BACKGROUND ART

An oatp/LST gene group (SLC21 family) of organic anion transporters is a group of sodium-independent transporters known to play an important role plays an important role in homeostasis of the living body, such as incorporation of thyroid hormones via the blood-brain barrier into the central nerve system in the living body, transfer of bile acid or chemicals from blood to the liver, removal of inflammatory mediators such as pristanglandine or leukotriene, and excretion of foreign matters into bile or urine. For the oatp/LST group, there are reports on 13 types of transporters in human (for example, SLC21A3, SLC21A6, SLC21A11, SLC21A12 (Biochemical and Biophysical Research Communications, 273, 251, 2000) and 10 types of transporters in rat (for example, Slc21a1, Slc21a5 etc.), and depending on distribution of expression, the oatp/LST group is classified roughly into three types, i.e., transporters expressed specifically in the brain, expressed specifically in the liver, and expressed ubiquitously.

The organic anion transporters transport not only bile acid as substrate but also physiologically active substances such as thyroid hormones and conjugated steroids. Many of these substrates are ligands of intracellular receptors, and thus the organic anion transporters are considered to play an important role in initially taking the ligands of intracellular receptors into cells. However, the detailed mechanism is still not well elucidated. Accordingly, elucidation of the role of these transporters is considered to lead to development of therapeutic agents for various diseases.

DISCLOSURE OF THE INVENTION

As a result of extensive study, the present inventors found a novel organic anion transporter protein. Methods of inhibiting the protein may include, for example, a method of inhibiting the transport of organic anions, and a method of inhibiting the transcription of the protein to reduce the expression level. Methods of activating the protein may include, for example, a method of activating the transport of organic anions, and a method of activating a promoter for the protein, and a method of stabilizing mRNA to promote the expression level.

On the basis of these findings, the present inventors made further extensive study, and as a result the present invention was completed.

That is, the present invention provides:
(1) A protein comprising the same or substantially the same amino acid sequence as an amino acid sequence represented by SEQ ID NO: 1, SEQ ID NO: 26 or SEQ ID NO: 52, or a salt thereof.
(2) A protein consisting of an amino acid sequence represented by SEQ ID NO: 1, or a salt thereof.
(3) A protein consisting of an amino acid sequence represented by SEQ ID NO: 26, or a salt thereof.
(4) A protein consisting of an amino acid sequence represented by SEQ ID NO: 52, or a salt thereof.
(5) The protein according to the above-mentioned (1) or a salt thereof, wherein substantially the same amino acid sequence as an amino acid sequence represented by SEQ ID NO: 52 is an amino acid sequence represented by SEQ ID NO: 54.
(6) A protein consisting of an amino acid sequence represented by SEQ ID NO: 54, or a salt thereof.
(7) A partial peptide of the protein according to the above-mentioned (1), or a salt thereof.
(8) A polynucleotide comprising a polynucleotide encoding the protein according to the above-mentioned (1) or the partial peptide according to the above-mentioned (7).
(9) The polynucleotide according to the above-mentioned (8), which is DNA.
(10) A polynucleotide consisting of a nucleotide sequence represented by SEQ ID NO: 2, SEQ ID NO: 27, SEQ ID NO: 53 or SEQ ID NO: 55.
(11) A recombinant vector comprising the polynucleotide according to the above-mentioned (8).
(12) A transformant transformed with the recombinant vector according to the above-mentioned (11).
(13) A method of manufacturing the protein or its salt according to the above-mentioned (1) or the partial peptide or its salt according to the above-mentioned (7), which comprises culturing the transformant according to the above-mentioned (12), forming and accumulating the protein according to the above-mentioned (1) or the partial peptide according to the above-mentioned (7), and recovering it.
(14) A pharmaceutical comprising the protein according to the above-mentioned (1) or the partial peptide according to the above-mentioned (7).
(15) A pharmaceutical comprising the polynucleotide according to the above-mentioned (8).
(16) A diagnostic agent comprising the polynucleotide according to the above-mentioned (8).
(17) An antibody to the protein according to the above-mentioned (1), the partial peptide according to the above-mentioned (7), or a salt of the protein or partial peptide.
(18) A diagnostic agent comprising the antibody according to the above-mentioned (17).
(19) A pharmaceutical comprising the antibody according to the above-mentioned (17).
(20) A polynucleotide comprising a nucleotide sequence complementary or substantially complementary to that of the polynucleotide according to the above-mentioned (8) or a part of the nucleotide sequence.
(21) A diagnostic agent comprising the polynucleotide according to the above-mentioned (20).
(22) A pharmaceutical comprising the polynucleotide according to the above-mentioned (20).
(23) A method of screening a compound or its salt that promotes or inhibits the activity of the protein or its salt according to the above-mentioned (1) or the partial peptide or its salt according to the above-mentioned (7), which comprises using the protein or its salt according to the above-mentioned (1) or the partial peptide or its salt according to the above-mentioned (7).
(24) A kit for screening a compound or its salt that promotes or inhibits the activity of the protein or its salt according to the above-mentioned (1) or the partial peptide or its salt according to the above-mentioned (7), which comprises the protein or its salt according to the above-mentioned (1) or the partial peptide or its salt according to the above-mentioned (7).

(25) A compound or its salt that promotes or inhibits the activity of the protein or its salt according to the above-mentioned (1) or the partial peptide or its salt according to the above-mentioned (7), which is obtained by using the screening method according to the above-mentioned (23) or the screening kit according to the above-mentioned (24).

(25a) A compound or its salt that promotes the activity of the protein or its salt according to the above-mentioned (1) or the partial peptide or its salt according to the above-mentioned (7).

(26) A pharmaceutical comprising the compound or its salt according to the above-mentioned (25).

(26a) A pharmaceutical comprising the compound or its salt according to the above-mentioned (25a).

(27) A method of screening a compound or its salt that promotes or inhibits the expression of a gene for the protein according to the above-mentioned (1), which comprises using the polynucleotide according to the above-mentioned (8).

(28) A kit for screening a compound or its salt that promotes or inhibits the expression of a gene for the protein according to the above-mentioned (1), which comprises the polynucleotide according to the above-mentioned (8).

(29) A compound or its salt that promotes or inhibits the expression of a gene for the protein according to the above-mentioned (1), which is obtained by the screening method according to the above-mentioned (27) or the screening kit according to the above-mentioned (28).

(29a) A compound or its salt that promotes the expression of a gene for the protein according to the above-mentioned (1).

(30) A pharmaceutical comprising the compound or its salt according to the above-mentioned (29).

(30a) A pharmaceutical comprising the compound or its salt according to the above-mentioned (29a).

(31) A method of quantifying the protein according to the above-mentioned (1), which comprises using the antibody according to the above-mentioned (17).

(32) A method of diagnosing diseases associated with the function of the protein according to the above-mentioned (1), which comprises using the quantification method according to the above-mentioned (31).

(33) A method of screening a compound or its salt that promotes or inhibits the expression of the protein according to the above-mentioned (1), which comprises using the antibody according to the above-mentioned (17).

(34) A kit for screening a compound or its salt that promotes or inhibits the expression of the protein according to the above-mentioned (1), which comprises the antibody according to the above-mentioned (17).

(35) A compound or its salt that promotes or inhibits the expression of the protein according to the above-mentioned (1), which is obtained by using the screening method according to the above-mentioned (33) or the screening kit according to the above-mentioned (34).

(35a) A compound or its salt that promotes the expression of the protein according to the above-mentioned (1).

(36) A pharmaceutical comprising the compound according to the above-mentioned (35) or a salt thereof.

(36a) A pharmaceutical comprising the compound according to the above-mentioned (35a) or a salt thereof.

(37) The pharmaceutical according to the above-mentioned (14), (15), (19), (22), (26), (30) or (36), which is a prophylactic/therapeutic agent for renal diseases.

(37a) The pharmaceutical according to the above-mentioned (26a), (30a) or (36a), which is a prophylactic/therapeutic agent for renal diseases.

(37b) The pharmaceutical according to the above-mentioned (37) or (37a), wherein the renal disease is diabetic nephropathy.

(37c) The pharmaceutical according to the above-mentioned (14), (15), (19), (22), (26), (30) or (36), which is a prophylactic/therapeutic agent for thyroid hormone-related diseases.

(37d) The pharmaceutical according to the above-mentioned (26a), (30a) or (36a), which is a prophylactic/therapeutic agent for thyroid hormone-related diseases.

(37e) The pharmaceutical according to the above-mentioned (37c) or (37d), wherein the thyroid hormone-related disease is Refetoff syndrome.

(38) A method of preventing/treating renal diseases, which comprises administering an effective amount of the compound according to the above-mentioned (25), (29) or (35) or a salt thereof to a mammalian animal.

(39) Use of the compound according to the above-mentioned (25), (29) or (35) or a salt thereof in producing a prophylactic/therapeutic agent for renal diseases.

BRIEF DESCRIPTION OF THE DRAWING

FIG. 1 shows comparison in amino acid sequence among human TCH229, human SLC21A12 and human OATPRP4. In the figure, TCH229 shows an amino acid sequence of human TCH229 [SEQ ID NO: 1]; SLC21A12 shows an amino acid sequence of human SLC21A12 [SEQ ID NO: 85]; OATPRP4 shows an amino acid sequence of human OATPRP4 [SEQ ID NO: 86]; and TM1 to TM12 show a transmembrane domain, respectively. □ shows amino acids coincident with those of human TCH229 (continued to FIG. 2).

FIG. 2 shows comparison in amino acid sequence among human TCH229, human SLC21A12 and human OATPRP4. In the figure, TCH229 shows an amino acid sequence of human TCH229 [SEQ ID NO: 1]; SLC21A12 shows an amino acid sequence of human SLC21A12 [SEQ ID NO: 85]; OATPRP4 shows an amino acid sequence of human OATPRP4 [SEQ ID NO: 86]; and TM1 to TM12 show a transmembrane domain, respectively. □ shows amino acids coincident with those of human TCH229 (continued from FIG. 1).

FIG. 5 shows comparison in amino acid sequence between human TCH229 and mouse TCH229. In the figure, TCH229 shows an amino acid sequence of human TCH229 [SEQ ID NO: 1]; mTCH229 shows an amino acid sequence of mouse TCH229 [SEQ ID NO: 26]; TM1 to TM12 show a transmembrane domain respectively; and highly stored amino acids in the family are shown by *. □ shows coincident amino acids between the two.

FIG. 7 shows comparison in amino acid sequence among human TCH229 and rat TCH229 Nos. 1 and 2. In the figure, TCH229 shows an amino acid sequence of human TCH229 [SEQ ID NO: 1]; rTCH229 No. 1 shows an amino acid sequence of rat TCH229 No. 1 [SEQ ID NO: 52]; and rTCH229 No. 2 shows an amino acid sequence of rat TCH229 No. 2 [SEQ ID NO: 54]. TM1 to TM12 show a transmembrane domain respectively. □ shows coincident amino acids among the three (continued to FIG. 8).

FIG. 8 shows comparison in amino acid sequence among human TCH229 and rat TCH229 Nos. 1 and 2. In the figure, TCH229 shows an amino acid sequence of human TCH229 [SEQ ID NO: 1]; rTCH229 No. 1 shows an amino acid sequence of rat TCH229 No. 1 [SEQ ID NO: 52]; and rTCH229 No. 2 shows an amino acid sequence of rat TCH229 No. 2 [SEQ ID NO: 54]. TM1 to TM12 show a transmembrane domain respectively. □ shows coincident amino acids among the three (continued from FIG. 7).

BEST MODE FOR CARRYING OUT THE INVENTION

Figure 3:
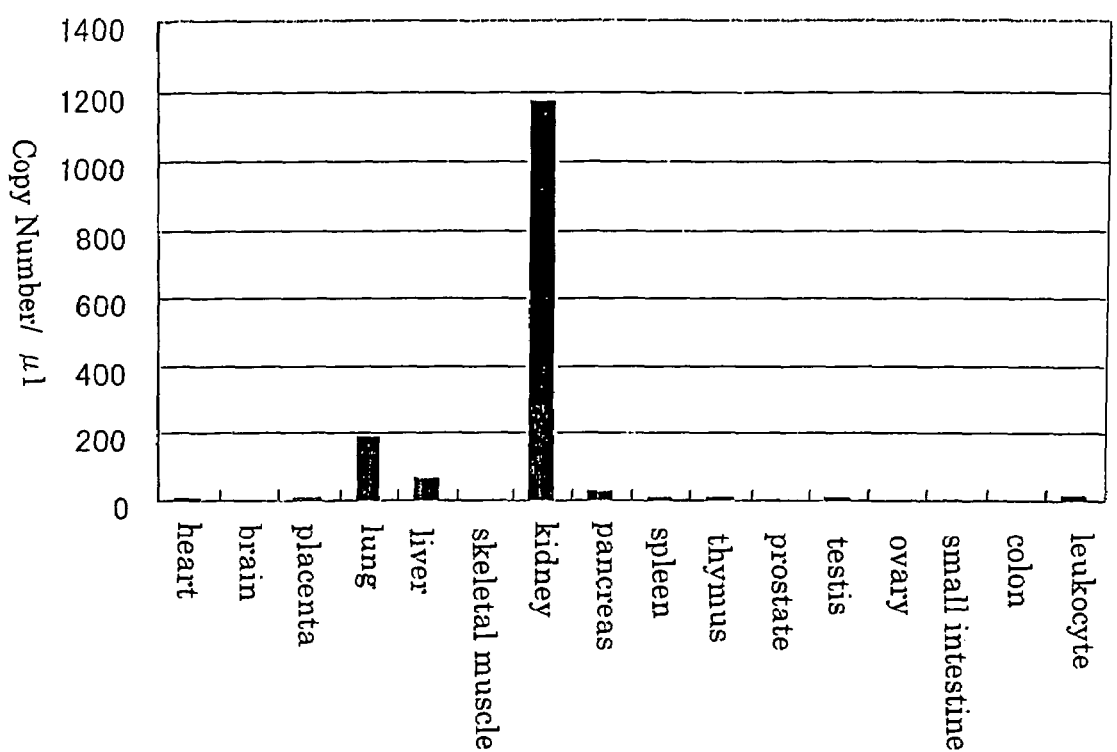
FIG. 3 shows the expression level of human TCH229 gene product in each tissue. The expression level is expressed in terms of the copy number per μl of cDNA solution.

A protein comprising the same or substantially the same amino acid sequence as an amino acid sequence represented by SEQ ID NO: 1, 26 or 52 (hereinafter, sometimes referred as to the protein of the present invention) may be any protein derived from any cells (e.g., liver cells, splenocytes, nerve cells, glial cells, β cells of pancreas, bone marrow cells, mesangial cells, Langerhans' cells, epidermic cells, epithelial cells, goblet cells, endothelial cells, smooth muscular cells, fibroblasts, fibrocytes, myocytes, fat cells, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells, cancer cells, etc.), or any tissues where such cells are present, e.g., brain or any region of the brain (e.g., olfactory bulb, amygdaloid nucleus, basal ganglia, hippocampus, thalamus, hypothalamus, cerebral cortex, medulla oblongata and cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc. from human and non-human mammals (e.g., guinea pigs, rats, mice, chickens, rabbits, swine, sheep, bovine, monkeys, etc.), or the protein may also be a synthetic protein.

Substantially the same amino acid sequence as the amino acid sequence represented by SEQ ID NO: 1 includes an amino acid sequence having at least about 50% homology, preferably at least about 60% homology, more preferably at least about 70% homology, still more preferably at least about 80% homology, further more preferably at least about 90% homology, further still more preferably at least about 95% homology and most preferably at least about 99% homology to the amino acid sequence represented by SEQ ID NO: 1.

Preferable examples of the protein comprising substantially the same amino acid sequence as that represented by SEQ ID NO: 1 include a protein comprising substantially the same amino acid sequence as that represented by SEQ ID NO: 1 and having an activity substantially equivalent to that of a protein having the amino acid sequence represented by SEQ ID NO: 1, etc.

Substantially the same amino acid sequence as that represented by SEQ ID NO: 26 includes an amino acid sequence having at least about 50% homology, preferably at least about 60% homology, more preferably at least about 70% homology, still more preferably at least about 80% homology, further more preferably at least about 90% homology, further still more preferably at least about 95% homology and most preferably about 99% homology to the amino acid sequence represented by SEQ ID NO: 26.

Preferable examples of the protein comprising substantially the same amino acid sequence as that represented by SEQ ID NO: 26 include a protein comprising substantially the same amino acid sequence as that represented by SEQ ID NO: 26 and having an activity substantially equivalent to a protein having the amino acid sequence represented by SEQ ID NO: 26, etc.

Substantially the same amino acid sequence as the amino acid sequence represented by SEQ ID NO: 52 includes an amino acid sequence having at least about 50% homology, preferably at least about 60% homology, more preferably at least about 70% homology, still more preferably at least about 80% homology, further more preferably at least about 90% homology, further still more preferably at least about 95% homology and most preferably at least about 99% homology to the amino acid sequence represented by SEQ ID NO: 52.

Preferable examples of the protein comprising substantially the same amino acid sequence as that represented by SEQ ID NO: 52 include a protein comprising substantially the same amino acid sequence as that represented by SEQ ID NO: 52 and having an activity substantially equivalent to that of a protein having the amino acid sequence represented by SEQ ID NO: 52, etc. The protein comprising substantially the same amino acid sequence as that represented by SEQ ID NO: 52 includes a protein comprising an amino acid sequence represented by SEQ ID NO: 54, etc.

As the substantially equivalent activity, there is for example organic anion transport activity and the like. The terms "substantially equivalent" mean that the property is inherently (e.g. physiologically or pharmacologically) equivalent. Therefore, although it is preferred that the above-mentioned organic anion transport activity be equivalent (e.g., about 0.01- to 100-fold, preferably about 0.1- to 10-fold, more preferably about 0.5- to 2-fold), quantitative factors such as a level of the activity, a molecular weight of the protein, etc. may differ.

The organic anion includes, for example, glucuronic acid, glutathione, bile acid such as cholic acid, and thyroid hormone.

The activities such as organic anion transport activity can be determined according to a publicly known method, for example, by a method described in Biochemical and Biophysical Research Communications, 273, 251, 2000, or its modified method.

The protein of the present invention includes, for example, (1) (i) an amino acid sequence represented by SEQ ID NO: 1, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10, and most preferably several (1 to 5) amino acids) are deleted, (ii) an amino acid sequence represented by SEQ ID NO: 1, to which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10, and most preferably several (1 to 5) amino acids) are added, (iii) an amino acid sequence represented by SEQ ID NO: 1, into which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10, and most preferably several (1 to 5) amino acids) are inserted, (iv) an amino acid sequence represented by SEQ ID NO: 1, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10, and most preferably several (1 to 5) amino acids) are substituted by other amino acids or (v) muteins comprising a combination of the amino acid sequences described above, (2) (i) an amino acid sequence represented by SEQ ID NO: 26, from which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably approximately 1 to 10 amino acids and more preferably several (1 to 5) amino acids) are deleted, (ii) an amino acid sequence represented by SEQ ID NO: 26, to which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are added, (iii) an amino acid sequence represented by SEQ ID NO: 26, into which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are inserted, (iv) an amino acid sequence represented by SEQ ID NO: 26, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are substituted by other amino acids or (v) muteins comprising a combination of the amino acid sequences described above, and (3) (i) an amino acid sequence represented by SEQ ID NO: 52, from which at least 1 or 2 amino acids (for example approximately 1 to 200 amino acids, preferably approximately 1 to 150 amino acids, more preferably approximately 1 to 100 amino acids, still more preferably approximately 1 to 50 amino acids, still further more preferably approximately 1 to 30 amino acids, even still more preferably approximately 1 to 10 amino acids and most preferably several (1 to 5) amino acids) are deleted, (ii) an amino acid sequence represented by SEQ ID NO: 52, to which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are added, (iii) an amino acid sequence represented by SEQ ID NO: 52, into which at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are inserted, (iv) an amino acid sequence represented by SEQ ID NO: 52, wherein at least 1 or 2 amino acids (for example approximately 1 to 200 amino acids, preferably approximately 1 to 150 amino acids, more preferably approximately 1 to 100 amino acids, still more preferably approximately 1 to 50 amino acids, further more preferably approximately 1 to 30 amino acids, further still more preferably 1 to 10 amino acids and most preferably several (1 to 5) amino acids) are substituted by other amino acids or (v) muteins comprising a combination of the amino acid sequences described above.

When the amino acid sequence has undergone insertion, deletion or substitution as described above, the position of the insertion, deletion or substitution is not particularly limited.

The proteins in the present specification are represented in accordance with the conventional way of describing peptides, that is, the N-terminus (amino terminus) at the left hand and the C-terminus (carboxyl terminus) at the right hand. In the proteins of the present invention including the protein comprising the amino acid sequence represented by SEQ ID NO: 1, the C-terminus is usually in the form of a carboxyl group (—COOH) or a carboxylate (—COO⁻) but may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, alpha-naphthyl, etc.; a $C_{7-14}$ aralkyl group such as a phenyl-$C_{1-2}$-alkyl group, e.g., benzyl, phenethyl, etc., or an alpha-naphthyl-$C_{1-2}$-alkyl group such as alpha-naphthylmethyl, etc.; and a pivaloyloxymethyl group or the like.

Where the protein of the present invention has a carboxyl group (or a carboxylate) at a position other than the C-terminus, it may be amidated or esterified and such an amide or ester is also included within the protein of the present invention. As the ester group herein, the same esters as those described with respect to the above C-terminal are used.

Furthermore, examples of the protein of the present invention include variants of the above proteins, wherein the N-terminal amino group residue (e.g. methionine residue) of the protein supra is protected with a protecting group (for example, a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins having sugar chains bound thereto.

Specific examples of the protein of the present invention include proteins comprising amino acid sequences represented by SEQ ID NO: 1, SEQ ID NO: 26, SEQ ID NO: 52 and SEQ ID NO: 54, respectively.

Partial peptides of the protein of the present invention may be any peptides insofar as they are partial peptides of the protein of the present invention and preferably have properties identical with those of the protein of the present invention.

For example, peptides having at least 10 amino acids, preferably at least 20 amino acids, more preferably at least 50 amino acids, still more preferably at least 70 amino acids, further more preferably at least 100 amino acids, further still more preferably at least 200 amino acids in the amino acid sequence which constitutes the protein of the present invention are used.

The partial peptide used in the present invention may be peptides containing an amino acid sequence, from which at least 1 or 2 amino acids (preferably approximately 1 to 20 amino acids, more preferably approximately 1 to 10 amino acids, still more preferably several (1 to 5) amino acids) are deleted, to which at least 1 or 2 amino acids (preferably approximately 1 to 20 amino acids, more preferably approximately 1 to 10 amino acids, still more preferably several (1 to 5) amino acids) are added, into which at least 1 or 2 amino acids (preferably approximately 1 to 20 amino acids, more preferably approximately 1 to 10 amino acids, still more preferably approximately several (1 to 5) amino acids) are inserted, or in which at least 1 or 2 amino acids (preferably approximately 1 to 20 amino acids, more preferably approximately 1 to 10 amino acids, still more preferably approximately several (1 to 5) amino acids) are substituted by other amino acids.

The partial peptide of the present invention comprises, for example, a peptide comprising an amino acid sequence in e.g. positions 340 to 370 or 490 to 520 in the amino acid sequence represented by SEQ ID NO: 1, a peptide comprising an amino acid sequence in e.g. positions 335 to 365 or 490 to 520 in the amino acid sequence represented by SEQ ID NO: 26, a peptide comprising an amino acid sequence in e.g. positions 335 to 365 or 490 to 520 in the amino acid sequence represented by SEQ ID NO: 52, and a peptide comprising an amino acid sequence in e.g. positions 335 to 365 or 490 to 520 in the amino acid sequence represented by SEQ ID NO: 54.

In the partial peptide used in the present invention, the C-terminus may be in any form of a carboxyl group (—COOH), a carboxylate (—COO—), an amide (—CONH$_2$) or an ester (—COOR).

Furthermore, the partial peptide used in the present invention includes variants having a carboxyl group (or a carboxylate) at a position other than the C-terminus, those wherein the amino group at the N-terminal amino acid residues (e.g., methionine residue) is protected with a protecting group; those wherein the N-terminal region is cleaved in vivo and the glutamyl group thus formed is pyroglutaminated; those wherein a substituent on the side chain of an amino acid in the molecule is protected with a suitable protecting group, or conjugated proteins such as so-called glycoproteins having sugar chains; etc., as in the protein used in the present invention described above.

The partial peptide used in the present invention can also be used as an antigen for preparing an antibody. For the purpose of preparing the antibody of the present invention, the following peptides are preferable: for example, a peptide comprising an amino acid sequence in e.g. positions 340 to 370 or 490 to 520 in the amino acid sequence represented by SEQ ID NO: 1, a peptide comprising an amino acid sequence in e.g. positions 335 to 365 or 490 to 520 in the amino acid sequence represented by SEQ ID NO: 26, a peptide comprising an amino acid sequence in e.g. positions 335 to 365 or 490 to 520 in the amino acid sequence represented by SEQ ID NO: 52, and a peptide comprising an amino acid sequence in e.g. positions 335 to 365 or 490 to 520 in the amino acid sequence represented by SEQ ID NO: 54.

As salts of the protein or partial peptide of the present invention, salts with physiologically acceptable acids (e.g., inorganic acids or organic acids) or bases (e.g., alkali metal salts) may be employed, preferably in the form of physiologically acceptable acid addition salts among others. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The protein or partial peptide of the present invention or salts thereof may be manufactured by a publicly known method used to purify a protein from human or other warm-blooded animal cells or tissues described above. Alternatively, they may also be manufactured by culturing transformants containing DNAs encoding the protein. Furthermore, they may also be manufactured by a modification of the methods for peptide synthesis, which will be described hereinafter.

Where these proteins are manufactured from human or other mammalian tissues or cells, human or other mammalian tissues or cells are homogenized, extracted with an acid or the like, and the extract is isolated and purified by a combination of chromatography techniques such as reverse phase chromatography, ion exchange chromatography, and the like.

To synthesize the protein or partial peptide used in the present invention or its salts, or amides thereof, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids, in which α-amino groups and functional groups on the side chains are appropriately protected, are condensed on the resin in the order of the sequence of the objective protein according to various condensation methods publicly known in the art. At the end of the reaction, the protein or partial peptide is excised from the resin and at the same time, the protecting groups are removed. Then, intramolecular disulfide bond-forming reaction is performed in a highly diluted solution to obtain the objective protein or partial peptide, or amides thereof.

For condensation of the protected amino acids described above, a variety of activation reagents for protein synthesis may be used, and carbodiimides are particularly employed. Examples of such carbodiimides include DCC, N,N'-diisopropylcarbodiimide, N-ethyl-N'-(3-dimethylaminopropyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; pyridine, ethers such as dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (linear, branched or cyclic alkyl esterification of, e.g., methyl, ethyl, propyl, butyl, t-butyl, cyclopentyl, cyclohexyl, cycloheptyl, cyclooctyl, 2-adamantyl, etc.), aralkyl esterification (e.g., benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, or a mixture solution of these acids; a treatment with a base such as diisopropylethylamine, triethylamine, piperidine or piperazine; reduction with sodium in liquid ammonia, etc. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the desired protein or partial peptide, for example, the alpha-carboxyl group of the carboxy terminal amino acid is first protected by amidation; the peptide (protein) chain is then extended from the amino group side to a desired length. Thereafter, a protein or partial peptide, in which only the protecting group of the N-terminal alpha-amino group of the peptide chain has been eliminated, and a protein or partial peptide, in which only the protecting group of the C-terminal carboxyl group has been eliminated are manufactured. The two proteins or peptides are condensed in a mixture of the solvents described above. The details of the condensation reaction are the same as described above. After the protected protein or peptide obtained by the condensation is purified, all the protecting groups are eliminated by the method described above to give the desired crude protein or peptide. This crude protein or peptide is purified by various known purification means. Lyophilization of the major fraction gives the amide of the desired protein or peptide.

To obtain the esterified protein or peptide, for example, the α-carboxyl group of the carboxy terminal amino acid is condensed with a desired alcohol to prepare the amino acid ester, which is followed by procedures similar to the preparation of the amidated protein or peptide above to give the desired esterified protein or peptide.

The partial peptide used in the present invention or salts thereof can be manufactured by publicly known methods for peptide synthesis, or by cleaving the protein used in the present invention with an appropriate peptidase. For the methods for peptide synthesis, for example, either solid phase synthesis or liquid phase synthesis may be used. That is, the partial peptide or amino acids that can construct the partial peptide of the present invention are condensed with the remaining part. Where the product contains protecting groups, these protecting groups are removed to give the desired peptide. Publicly known methods for condensation and elimination of the protecting groups are described in (a) to (e) below.

(a) M. Bodanszky & M. A. Ondetti: Peptide Synthesis, Interscience Publishers, New York (1966)
(b) Schroeder & Luebke: The Peptide, Academic Press, New York (1965)
(c) Nobuo Izumiya, et al.: Peptide Gosei-no-Kiso to Jikken (Basics and experiments of peptide synthesis), published by Maruzen Co. (1975)
(d) Haruaki Yajima & Shunpei Sakakibara: Seikagaku Jikken Koza (Biochemical Experiment) 1, Tanpakushitsu no Kagaku (Chemistry of Proteins) IV, 205 (1977)
(e) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide used in the present invention. When the partial peptide obtained by the above methods is in a free form, the partial peptide can be converted into an appropriate salt by a publicly known method; when the partial peptide is obtained in a salt form, it can be converted into a free form or other different salt form by a publicly known method.

The polynucleotide encoding the protein used in the present invention may be any polynucleotide so long as it contains the base sequence encoding the protein used in the present invention described above. Preferably, the polynucleotide is a DNA. The DNA may also be any one of genomic DNA, genomic DNA library, cDNA derived from the cells or tissues described above, cDNA library derived from the cells or tissues described above and synthetic DNA.

The vector to be used for the library may be any of bacteriophage, plasmid, cosmid, phagemid, ane the like. The DNA may also be directly amplified by reverse transcriptase polymerase chain reaction (hereinafter abbreviated as RT-PCR) using the total RNA or mRNA fraction prepared from the cells/tissues described above.

The DNA encoding the protein of the present invention may be for example (i) DNA comprising the nucleotide sequence represented by SEQ ID NO: 2, or DNA hybridizing under high stringent conditions with the nucleotide sequence represented by SEQ ID NO: 2 and encoding a protein having properties substantially equivalent to those of a protein comprising the amino acid sequence represented by SEQ ID NO: 1, (ii) DNA comprising the nucleotide sequence represented by SEQ ID NO: 25, or DNA hybridizing under high stringent conditions with the nucleotide sequence represented by SEQ ID NO: 25 and encoding a protein having properties substantially equivalent to those of a protein comprising the amino acid sequence represented by SEQ ID NO: 1, (iii) DNA comprising the nucleotide sequence represented by SEQ ID NO: 27, or DNA hybridizing under high stringent conditions with the nucleotide sequence represented by SEQ ID NO: 27 and encoding a protein having properties substantially equivalent to those of a protein comprising the amino acid sequence represented by SEQ ID NO: 26, (iv) DNA comprising the nucleotide sequence represented by SEQ ID NO: 51, or DNA hybridizing under high stringent conditions with the nucleotide sequence represented by SEQ ID NO: 51 and encoding a protein having properties substantially equivalent to those of a protein comprising the amino acid sequence represented by SEQ ID NO: 26, (v) DNA comprising the nucleotide sequence represented by SEQ ID NO: 53, or DNA hybridizing under high stringent conditions with the nucleotide sequence represented by SEQ ID NO: 53 and encoding a protein having properties substantially equivalent to those of a protein comprising the amino acid sequence represented by SEQ ID NO: 52, (vi) DNA comprising the nucleotide sequence represented by SEQ ID NO: 80, or DNA hybridizing under high stringent conditions with the nucleotide sequence represented by SEQ ID NO: 80 and encoding a protein having properties substantially equivalent to those of a protein comprising the amino acid sequence represented by SEQ ID NO: 52, (vii) DNA comprising the nucleotide sequence represented by SEQ ID NO: 55, or DNA hybridizing under high stringent conditions with the nucleotide sequence represented by SEQ ID NO: 55 and encoding a protein having properties substantially equivalent to those of a protein comprising the amino acid sequence represented by SEQ ID NO: 54, and (viii) DNA comprising the nucleotide sequence represented by SEQ ID NO: 81, or DNA hybridizing under high stringent conditions with the nucleotide sequence represented by SEQ ID NO: 81 and encoding a protein having properties substantially equivalent to those of a protein comprising the amino acid sequence represented by SEQ ID NO: 54.

As the DNA hybridizing under high stringent conditions with the nucleotide sequence represented by SEQ ID NO: 2 or SEQ ID NO: 25, there may be employed e.g. DNA comprising a nucleotide sequence having at least about 50% homology, preferably at least about 60% homology, more preferably at least about 70% homology, still more preferably at least about 80% homology, further more preferably at least about 90% homology, even more preferably at least about 95% homology and most preferably at least about 99% homology to the nucleotide sequence represented by SEQ ID NO: 2 or SEQ ID NO: 25.

As the DNA hybridizing under high stringent conditions with the nucleotide sequence represented by SEQ ID NO: 27 or SEQ ID NO: 51, there may be employed e.g. DNA comprising a nucleotide sequence having at least about 50% homology, preferably at least about 60% homology, more preferably at least about 70% homology, still more preferably at least about 80% homology, further more preferably at least about 90% homology, even more preferably at least about 95% homology and most preferably at least about 99% homology to the nucleotide sequence represented by SEQ ID NO: 27 or SEQ ID NO: 51.

As the DNA hybridizing under high stringent conditions with the nucleotide sequence represented by SEQ ID NO: 53 or SEQ ID NO: 80, there may be employed e.g. DNA comprising a nucleotide sequence having at least about 50% homology, preferably at least about 60% homology, more preferably at least about 70% homology, still more preferably at least about 80% homology, further more preferably at least about 90% homology, even more preferably at least about 95% homology and most preferably at least about 99% homology to the nucleotide sequence represented by SEQ ID NO: 53 or SEQ ID NO: 80.

As the DNA hybridizing under high stringent conditions with the nucleotide sequence represented by SEQ ID NO: 55 or SEQ ID NO: 81, there may be employed e.g. DNA comprising a nucleotide sequence having at least about 50% homology, preferably at least about 60% homology, more preferably at least about 70% homology, still more preferably at least about 80% homology, further more preferably at least about 90% homology, even more preferably at least about 95% homology and most preferably at least about 99% homology to the nucleotide sequence represented by SEQ ID NO: 55 or SEQ ID NO: 81.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

More specifically, as the DNA encoding a protein comprising the amino acid sequence represented by SEQ ID NO: 1, there may be employed e.g. DNA comprising the nucleotide sequence represented by SEQ ID NO: 2 or SEQ ID NO: 25; as the DNA encoding a protein comprising the amino acid sequence represented by SEQ ID NO: 26, there may be employed e.g. DNA comprising the nucleotide sequence represented by SEQ ID NO: 27 or SEQ ID NO: 51; as the DNA encoding a protein comprising the amino acid sequence represented by SEQ ID NO: 52, there may be employed e.g. DNA comprising the nucleotide sequence represented by SEQ ID NO: 53 or SEQ ID NO: 80; and as the DNA encoding a protein comprising the amino acid sequence represented by SEQ ID NO: 54, there may be employed e.g. DNA comprising the nucleotide sequence represented by SEQ ID NO: 55 or SEQ ID NO: 81.

The polynucleotide (e.g., DNA) encoding the partial peptide used in the present invention may be any polynucleotide so long as it comprises a nucleotide sequence encoding the above-described partial peptide used in the present invention. The DNA may also be any of genomic DNA, genomic DNA library, cDNA derived from the cells and tissues described above, cDNA library derived from the cells and tissues described above, and synthetic DNA.

As the DNA encoding the partial peptide used in the present invention, there may be employed for example (1) DNA having a part of the nucleotide sequence represented by SEQ ID NO: 2 or SEQ ID NO: 25, or DNA comprising a nucleotide sequence hybridizing under high stringent conditions with the nucleotide sequence represented by SEQ ID NO: 2 or SEQ ID NO: 25 and comprising a part of DNA encoding a protein having a substantially equivalent activity to the protein of the present invention, (2) DNA having a part of the nucleotide sequence represented by SEQ ID NO: 27, or DNA comprising a nucleotide sequence hybridizing under high stringent conditions with the nucleotide sequence represented by SEQ ID NO: 27 and comprising a part of DNA encoding a protein having a substantially equivalent activity to the protein of the present invention, (3) DNA having a part of the nucleotide sequence represented by SEQ ID NO: 53, or DNA comprising a nucleotide sequence hybridizing under high stringent conditions with the nucleotide sequence represented by SEQ ID NO: 53 and comprising a part of DNA encoding a protein having a substantially equivalent activity to the protein of the present invention, and (4) DNA having a part of the nucleotide sequence represented by SEQ ID NO: 55, or DNA comprising a nucleotide sequence hybridizing under high stringent conditions with the nucleotide sequence represented by SEQ ID 55 and comprising a part of DNA encoding a protein having a substantially equivalent activity to the protein of the present invention.

The DNA which can hybridize with the nucleotide sequence represented by SEQ ID NO: 2, SEQ ID NO: 25, SEQ ID NO: 27, SEQ ID NO: 53 or SEQ ID NO: 55 has the same meaning as described above.

As the hybridization method and high stringent conditions, those described above are used.

For cloning of DNAs that completely encode the protein or partial peptide of the present invention (hereinafter sometimes merely referred to as the protein of the present invention in the description of cloning of DNAs encoding the protein and partial peptide and their expression), the DNA can be either amplified by PCR using synthetic DNA primers containing a part of the base sequence encoding the protein of the present invention, or the DNA inserted into an appropriate vector can be screened by hybridization with a labeled DNA fragment or synthetic DNA that encodes a part or entire region of the protein of the present invention. The hybridization can be carried out, for example, according to the method described in Molecular Cloning, 2nd (J. Sambrook et al., Cold Spring Harbor Lab. Press, 1989). Where the hybridization is carried out using commercially available library, the procedures may be conducted in accordance with the protocol described in the attached instructions.

Conversion of the base sequence of DNA can be effected by publicly known methods such as the ODA-LA PCR method, the Gapped duplex method, the Kunkel method, etc., or its modification, using PCR or a publicly known kit available as Mutan™-super Express Km or Mutan™-K (both manufactured by Takara Shuzo Co., Ltd.), etc.

The cloned DNA encoding the protein can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adaptor.

The expression vector for the protein of the present invention can be manufactured, for example, by (a) excising the desired DNA fragment from the DNA encoding the protein of the present invention, and then (b) ligating the DNA fragment with an appropriate expression vector downstream a promoter in the vector.

Examples of the vector include plasmids derived form $E.$ $coli$ (e.g., pBR322, pBR325, pUC12, pUC13), plasmids derived from $Bacillus$ $subtilis$ (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNA I/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, it is preferred to use CMV (cytomegalovirus) promoter, SRα promoter, etc. Where the host is bacteria of the genus $Escherichia$, preferred examples of the promoter include trp promoter, lac promoter, recA promoter, $\lambda P_L$ promoter, lpp promoter, T7 promoter, etc. In the case of using bacteria of the genus $Bacillus$ as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the protein of the present invention. Examples of the signal sequence that can be used are PhoA signal sequence, OmpA signal sequence, etc. when bacteria of the genus $Escherichia$ is used as the host; alpha-amylase signal sequence, subtilisin signal sequence, etc. when bacteria of the genus $Bacillus$ is used as the host; MFα signal sequence, SUC2 signal sequence, etc. when yeast is used as the host; and insulin signal sequence, alpha-interferon signal sequence, antibody molecule signal sequence, etc. when animal cells are used as the host, respectively.

Using the vector containing the DNA encoding the protein of the present invention thus constructed, transformants can be manufactured.

Examples of the host, which may be employed, are bacteria belonging to the genus $Escherichia,$ bacteria belonging to the genus $Bacillus,$ yeast, insect cells, insects, animal cells, etc.

Specific examples of the bacteria belonging to the genus $Escherichia$ include $Escherichia$ $coli$ K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus $Bacillus$ include $Bacillus$ $subtilis$ MI114 [Gene, 24, 255 (1983)], 207-21 [Journal of Biochemistry, 95, 87 (1984)], etc.

Examples of yeast include $Saccharomyces$ $cereviseae$ AH22, AH22R$^-$, NA87-11A, DKD-5D, 20B-12, $Schizosaccharomyces$ $pombe$ NCYC1913, NCYC2036, $Pichia$ $pastoris$ KM71, etc.

Examples of insect cells include, for the virus AcNPV, $Spodoptera$ $frugiperda$ cell (Sf cell), MG1 cell derived from mid-intestine of $Trichoplusia$ $ni,$ High Five™ cell derived from egg of $Trichoplusia$ $ni,$ cells derived from $Mamestra$ $brassicae,$ cells derived from $Estigmena$ $acrea,$ etc.; and for the virus BmNPV, $Bombyx$ $mori$ N cell (BmN cell), etc. is used. Examples of the Sf cell which can be used are Sf9 cell (ATCC CRL1711), Sf21 cell (both cells are described in Vaughn, J. L. et al., In Vivo, 13, 213-217 (1977)), etc.

As the insect, for example, a larva of $Bombyx$ $mori$ can be used [Maeda et al., Nature, 315, 592 (1985)].

As the insect, for example, a larva of $Bombyx$ $mori$ can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr$^-$) cell), mouse L cell, mouse AtT-20, mouse myeloma cell, rat GH 3, human FL cell, etc.

Bacteria belonging to the genus $Escherichia$ can be transformed, for example, by the method described in Proc. Natl. Acad. Sci. U.S.A., 69, 2110 (1972), Gene, 17, 107(1982), etc.

Bacteria belonging to the genus $Bacillus$ can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995) (published by Shujunsha), or Virology, 52, 456 (1973).

Thus, the transformants transformed with the expression vectors containing the DNAs encoding the protein can be obtained.

Where the host is bacteria belonging to the genus *Escherichia* or the genus *Bacillus,* the transformant can be appropriately cultured in a liquid medium which contains materials required for growth of the transformant such as carbon sources, nitrogen sources, inorganic materials, and the like. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultured generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to 8. In general, the transformant is cultivated at about 20° C. to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultured in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 to 60 hours and, if necessary, the culture can be aerated or agitated.

As described above, the protein of the present invention can be produced in the transformant, in the cell membrane of the transformant, or outside of the transformant.

The protein of the present invention can be separated and purified from the culture described above by the following procedures.

When the protein of the present invention is extracted from the bacteria or cells, the bacteria or cell is collected after culturing by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc. Thus, the crude extract of the protein can be obtained. The buffer used for the procedures may contain a protein modifier such as urea or guanidine hydrochloride, or a surfactant such as Triton X-100™, etc. When the protein of the present invention is secreted in the culture broth, the supernatant can be separated, after completion of the cultivation, from the bacteria or cell to collect the supernatant by a publicly known method.

The protein contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the protein thus obtained is in a free form, the protein can be converted into the salt by publicly known methods or modifications thereof. On the other hand, when the protein is obtained in the form of a salt, it can be converted into the free form or in the form of a different salt by publicly known methods or modifications thereof.

The protein produced by the recombinant can be treated, prior to or after the purification, with an appropriate protein-modifying enzyme so that the protein can be appropriately modified to partially remove the polypeptide. Examples of the protein-modifying enzyme include trypsin, chymotrypsin, arginyl endopeptidase, protein kinase, glycosidase and the like.

The presence of the thus produced protein of the present invention can be determined by an enzyme immunoassay or western blotting using a specific antibody.

The antibodies to the protein or partial peptide of the present invention, or its salts may be any of polyclonal and monoclonal antibodies, as long as they are capable of recognizing the protein or partial peptide used in the present invention, or its salts.

The antibodies to the protein or partial peptide of the present invention, or its salts, (hereinafter they are sometimes collectively referred to as the protein of the present invention in the description of the antibodies) can be produced by a publicly known method of producing an antibody or antiserum, using the protein of the present invention as an antigen.

[Preparation of Monoclonal Antibody]

(a) Preparation of Monoclonal Antibody-Producing Cells

The protein of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every about 2 to about 6 weeks and about 2 to about 10 times in total. Examples of the applicable warm-blooded animals are monkeys, rabbits, dogs, guinea pigs, mice, rats, sheep, goats and chickens, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled protein, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the protein as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase, or the like.

The monoclonal antibody can be screened according to publicly known methods or their modifications. In general, the screening can be performed in a medium for animal cells supplemented with HAT (hypoxanthine, aminopterin and thymidine). Any screening and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like, can be used for the screening and growth medium. The culture is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (protein antigen) per se, or a complex of immunogen and a carrier protein is formed and a warm-blooded animal is immunized with the complex in a manner similar to the method described above for the manufacture of monoclonal antibodies. The product containing the antibody to the protein of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks and about 3 to 10 times in total.

The polyclonal antibody can be collected from the blood, ascites, etc., preferably from the blood of warm-blooded animal inmunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense polynucleotide having a complementary or substantial complementary base sequence to the DNA encoding the protein or partial peptide of the present invention (hereinafter these DNAs are sometimes collectively referred to as the DNA of the present invention in the description of antisense polynucleotide) can be any antisense polynucleotide, so long as it possesses a base sequence complementary or substantially complementary base sequence to that of the DNA of the present invention and capable of suppressing expression of the DNA, but antisense DNA is preferred.

The base sequence substantially complementary to the DNA of the present invention may include, for example, a base sequence having at least about 70% homology, preferably at least about 80% homology, more preferably at least about 90% homology and most preferably at least about 95% homology, to the full-length base sequence or to the partial base sequence (i.e., complementary strand to the DNA of the present invention), and the like. Especially in the full-length base sequence of the complementary strand to the DNA of the present invention, preferred is an antisense polynucleotide having at least about 70% homology, preferably at least about 80% homology, more preferably at least about 90% homology and most preferably at least about 95% homology, to the complementary strand of the base sequence which encodes the N-terminal region of the protein of the present invention (e.g., the base sequence around the initiation codon).

Specific examples include an antisense polynucleotide containing the entire or part of a base sequence complementary or substantially complementary to a base sequence of DNA containing the base sequence represented by SEQ ID NO: 2, SEQ ID NO: 27, SEQ ID NO: 53 or SEQ ID NO: 55, preferably an antisense polynucleotide containing the entire or part of a base sequence complementary to a base sequence of DNA containing the base sequence represented by SEQ ID NO: 2, SEQ ID NO: 27, SEQ ID NO: 53 or SEQ ID NO: 55.

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. These antisense nucleotides may be synthesized using a publicly known DNA synthesizer, etc.

According to the present invention, the antisense polynucleotide (nucleic acid) that can inhibit replication or expression of a gene for the protein of the present invention can be designed and synthesized based on the base sequence information of the cloned or determined DNA encoding the protein. Such a polynucleotide (nucleic acid) is hybridizable to RNA of a gene for the protein of the present invention to inhibit the synthesis or function of the RNA or is capable of modulating/controlling the expression of a gene for the protein of the present invention via interaction with RNA associated with the protein of the present invention. Polynucleotides complementary to the selected sequences of RNA associated with the protein of the present invention and polynucleotides specifically hybridizable to RNA associated with the protein of the present invention are useful in modulating/controlling the in vivo and in vitro expression of a gene for the protein of the present invention, and are useful for the treatment or diagnosis of diseases, etc. The term "corresponding" is used to mean homologous to or complementary to a particular sequence of the nucleotide including the gene, base sequence or nucleic acid. The term "corresponding" between nucleotides, base sequences or nucleic acids and peptides (proteins) usually refer to amino acids of a peptide (protein) under the order derived from the sequence of nucleotides (nucleic acids) or their complements. In the gene for the protein, the 5' end hairpin loop, 5' end 6-base-pair repeats, 5' end untranslated region, polypeptide translation initiation codon, protein coding region, ORF translation termination codon, 3' end untranslated region, 3' end palindrome region, and 3' end hairpin loop, may be selected as preferred target regions, though any other region may be selected as a target in the gene for the protein.

The relationship between the targeted nucleic acids and the polynucleotides complementary to at least a part of the target region, specifically the relationship between the target nucleic acids and the polynucleotides hybridizable to the target region, can be denoted to be "antisense" to the polynucleotides in the said target region. Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., alpha-anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cell permeability of the antisense nucleic acid, increasing the affinity of the nucleic acid to the targeted sense strand to a higher level, or minimizing the toxicity, if any, of the antisense nucleic acid. Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense polynucleotide of the present invention may contain altered or modified sugars, bases or linkages. The antisense polynucleotide may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the polynucleotide at the 3' or 5' ends thereof and may also be attached thereto through a base, sugar, or intramolecular nucleoside linkage. Other moieties may be capping groups specifically placed at the 3' or 5' ends of the polynucleotide to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense polypeptide can be examined using the transformant of the present invention, the gene expression system of the present invention in vivo and in vitro, or the translation system of the protein of the present invention in vivo and in vitro.

Hereinafter, the protein or partial peptide of the present invention, or salts thereof (hereinafter sometimes merely referred to as the protein of the present invention), the polynucleotide encoding the protein or partial peptide of the present invention, for example DNA (hereinafter sometimes merely referred to as the DNA of the present invention), the antibodies to the protein of the present invention, its partial peptides, or salts thereof (hereinafter sometimes referred to as the antibodies of the present invention) and the antisense polynucleotides to the DNA of the present invention (hereinafter sometimes merely referred to as the antisense polynucleotides of the present invention) are specifically described for their applications.

A pharmaceutical comprising the compound or its salt that inhibits the activity of the protein of the present invention can inhibit for example organic anion transport activity and can thus be used as a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.) etc. The pharmaceutical can be used preferably as a prophylactic/therapeutic agent for renal diseases and thyroid hormone-related diseases, more preferably as a prophylactic/therapeutic agent for diabetic nephropathy. On the other hand, a pharmaceutical comprising the compound or its salt that promotes the activity of the protein of the present invention (e.g., an organic anion transport activity) can be used preferably as a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The pharmaceutical can be used preferably as a prophylactic/therapeutic agent for renal diseases and thyroid hormone-related diseases, more preferably as a prophylactic/therapeutic agent for diabetic nephropathy.

[1] Agents for the Prevention/Treatment of Various Diseases with which the Protein of the Invention is Associated The protein of the present invention has an organic anion transport activity etc., and plays an important role in homeostasis of the living body, such as incorporation of thyroid hormones via the blood-brain barrier into the central nerve system in the living body, transfer of bile acid or chemicals from blood to the liver, removal of inflammatory mediators such as pristanglandine or leukotriene, and excretion of foreign matters into bile or urine.

Therefore, where the DNA encoding the protein of the present invention is abnormal or deficient, or where the expression level of the protein of the present invention is reduced, there occur various diseases such as renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc.

Accordingly, the protein of the present invention and the DNA of the present invention can be used as pharmaceuticals such as prophylactic/therapeutic agents for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The protein of the present invention and the DNA of the present invention can be used preferably as a prophylactic/therapeutic agent for renal diseases and thyroid hormone-related diseases, more preferably as a prophylactic/therapeutic agent for diabetic nephropathy.

For example, when there is a patient who cannot sufficiently or normally exhibit an activity of transporting organic anions because of a decrease or deficiency in the protein of the present invention in the living body, the role of the protein of the present invention in the patient can be exhibited sufficiently or normally: (a) by administering the DNA of the present invention directly to the patient thereby expressing the protein of the present invention in the living body; (b) by inserting the DNA of the present invention into cells to express the protein of the present invention and then transplanting the cells to the patient; or (c) by administering the protein of the present invention to the patient.

Where the DNA of the present invention is used as the prophylactic/therapeutic agents described above, the DNA itself is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the present invention may also be administered as an intact DNA, or prepared into medicines together with physiologically acceptable carriers such as adjuvants to assist its uptake, which are administered by gene gun or through a catheter such as a hydrogel catheter.

Where the protein of the present invention is used as the aforesaid prophylactic/therapeutic agents, the protein is advantageously used on a purified level of at least 90%, preferably at least 95%, more preferably at least 98% and most preferably at least 99%.

The protein of the present invention can be used orally, for example, in the form of tablets which may be sugar coated if necessary, capsules, elixirs, microcapsules, etc., or parenterally in the form of injectable preparations such as a sterile solution, a suspension, etc. in water or with other pharmaceutically acceptable liquid. These preparations can be prepared, for example, by mixing the protein, etc. of the present invention with a physiologically acceptable carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, a flavoring agent such as peppermint, akamono oil or cherry, and the like. When the unit dosage is in the form of capsules, liquid carriers such as oils and fats may further be used together with the additives described above. A sterile composition for injection may be formulated by conventional procedures used to make pharmaceutical preparations, e.g., by dissolving or suspending the active ingredients in a vehicle such as water for injection with a naturally occurring vegetable oil such as sesame oil, coconut oil, etc. to prepare the pharmaceutical preparations.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol, polyethylene glycol, etc.), a nonionic surfactant (e.g., polysorbate 80™, HCO-50, etc.), and the like. Examples of the oily medium include sesame oil and soybean oil, which may also be used in combination with a dissolution aid such as benzyl benzoate, benzyl alcohol, etc. The agent may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector inserted with the DNA of the present invention is prepared into pharmaceutical preparations as described above and normally provided for use parenterally.

Since the thus obtained pharmaceutical preparation is safe and low toxic, the preparation can be administered to warm-blooded animals (e.g., human, rats, mice, guinea pigs, rabbits, fowl, sheep, swine, bovine, horses, cats, dogs, monkeys, chimpanzees, etc.).

The dose of the protein of the present invention may vary depending upon target disease, subject to be administered, route of administration, etc. In oral administration of the protein of the present invention for the treatment of, e.g., renal insufficiency, generally the protein is administered to an adult (as 60 kg) in a dose of about 0.1 mg to 100 mg, preferably about 1.0 to 50 mg and more preferably about 1.0 to 20 mg per day. In parenteral administration, the single dose of the protein may vary depending on subject to be administered, target disease, etc. When the protein of the present invention is administered to an adult (as 60 kg body weight) in the form of injectable preparations for the treatment of, e.g., renal insufficiency, it is advantageous to inject the protein at the affected area in a daily dose of about 0.01 to about 30 mg, preferably about 0.1 to about 20 mg and more preferably about 0.1 to about 10 mg. For other animal species, the corresponding dose as converted per 60 kg can be administered.

[2] Screening of Drug Candidate Compounds for Disease

The protein of the present invention is useful as a reagent for screening compounds or salts thereof that promote or inhibit the activities of the protein of the present invention.

The present invention provides (1) a method of screening a compound or its salt (hereinafter, sometimes referred as to the promoter or inhibitor) that promotes or inhibits the activity (e.g., an activity of transporting organic anions, etc.) of the protein of the invention, which comprises using the protein of the present invention. More specifically, the present invention provides, for example: (2) a method of screening a promoter or an inhibitor, which comprises comparing (i) the organic anion transport activity of a cell having an ability to produce the protein of the present invention with (ii) the organic anion transport activity of a mixture of a test compound and a cell having an ability to produce the protein of the present invention.

Specifically, the screening method described above is characterized by measuring the organic anion transport activity in the cases of (i) and (ii) with a fluorescent coloring matter and comparing them in terms of organic anion transport activity as an indicator.

Examples of the test compound include peptides, proteins, non-peptide compounds, synthetic compounds, fermentation products, cell extracts, plant extracts, animal tissue extracts, etc. These compounds may be novel compounds or publicly known compounds.

To perform the screening methods described above, the cells capable of producing the protein of the present invention are suspended in a buffer suitable for the screening to prepare the cell suspension. Any buffer is usable as far as it is a buffer such as a phosphate buffer, borate buffer, etc. having pH of approximately 4 to 10 (preferably pH of about 6 to about 8) that does not interfere the organic anion transport activity of the protein of the present invention.

As the cells capable of producing the protein of the present invention, there is employed, e.g., the aforesaid host (transformant) transformed with a vector containing the DNA encoding the protein of the present invention. Preferably, animal cells such as CHO cells, etc. are used as the host. For the screening, the transformant, in which the protein of the present invention has been expressed on the cell membrane, for example, by culturing through the procedure described above, is preferably employed.

The organic anion transport activity of the protein of the present invention can be assayed by publicly known methods, e.g., by the method described in Biochemical and Biophysical Research Communications, 273, 251, 2000, or its modifications.

For example, when a test compound promotes the organic anion transport activity in the case (ii) described above by at least about 20%, preferably at least 30%, more preferably at least about 50%, as compared to the case (i) described above, the test compound can be selected as a compound capable of promoting the activity of the protein of the present invention, or as a salt of the compound.

Further, for example, when a test compound inhibits (or supressing) the organic anion transport activity in the case (ii) described above by at least about 20%, preferably at least 30%, more preferably at least about 50%, as compared to the case (i) described above, the test compound can be selected to be a compound capable of inhibiting the activity of the protein of the present invention, or a salt of the compound.

Furthermore, the compound or its salt that promotes or inhibits the expression of the protein of the present invention (i.e., promotes or inhibits the activity of the protein of the present invention) can also be screened by inserting a gene for secreted alkaline phosphatase, luciferase, etc. at the downstream of a promoter for a gene of the protein of the present invention, expressing the gene in the various cells described above, and investigating such a compound or its salt that activates or inhibits the enzyme activity when the test compound described above is brought in contact with the cells.

The polynucleotide encoding the protein of the present invention is useful as a reagent for screening the compound or its salt that promotes or inhibits a gene for the protein of the present invention.

The present invention provides (3) a method of screening a compound or its salt that promotes or inhibits the expression of a gene for the protein of the present invention (hereinafter sometimes merely referred to as the promoter or the inhibitor, respectively), which comprises using the polynucleotide encoding the protein of the present invention. More specifically, the present invention provides, for example: (4) a method of screening the promoter or the inhibitor, which comprises comparing (iii) the case where cells capable of producing the protein of the present invention are cultured and (iv) the case where a mixture of cells capable of producing the protein of the present invention and a test compound is cultured.

In the screening method described above, for example, the expression level of the gene for the protein of the present invention (specifically, the level of the protein of the present invention or the level of mRNA encoding the aforesaid protein) is measured in the cases (iii) and (iv) and comparison is made therebetween.

Examples of the test compound include peptides, proteins, non-peptide compounds, synthetic compounds, fermentation products, cell extracts, plant extracts, animal tissue extracts, etc. These compounds may be novel compounds or publicly known compounds.

To perform the screening methods described above, the cells capable of producing the protein of the present invention are suspended in a buffer suitable for the screening to prepare the cell suspension. Any buffer is usable as far as it is a buffer such as a phosphate buffer, borate buffer, etc. having pH of approximately 4 to 10 (preferably pH of about 6 to about 8) that does not inhibit the organic anion transport activity of the protein of the present invention.

As the cells capable of producing the protein of the present invention, there is employed, e.g., the aforesaid host (transformant) transformed with a vector containing the DNA encoding the protein of the present invention. Preferably, animal cells such as CHO cells, etc. are used as the host. For the screening, the transformant, in which the protein of the present invention has been expressed on the membrane such as endoplasmic reticulum membrane, Golgi membrane, cell membrane, etc., for example, by culturing through the procedure described above, is preferably employed.

The level of the protein of the present invention can be determined by publicly known methods, e.g., by measuring the aforesaid protein present in the cell extract, etc., using an antibody capable of recognizing the protein of the present invention, in accordance with methods like western blot analysis, ELISA, etc., or their modifications.

The expression level of the gene for the protein of the present invention can be determined by publicly known methods, e.g., in accordance with methods including Northern blotting, reverse transcription-polymerase chain reaction (RT-PCR), real time PCR monitoring system (manufactured by ABI, TaqMan polymerase chain reaction), etc., or their modifications.

For example, when a test compound promotes the expression level of the gene for the protein of the present invention in the case (iv) described above by at least about 20%, preferably at least 30%, more preferably at least about 50%, as compared to the case (iii) described above, the test compound can be selected to be a compound capable of promoting the expression of the gene for the protein of the present invention, or a salt of the compound.

For example, when a test compound inhibits the expression level of the gene for the protein of the present invention in the case (iv) described above by at least about 20%, preferably at least 30%, more preferably at least about 50%, as compared to the case (iii) described above, the test compound can be selected to be a compound capable of inhibiting the expression of the gene for the protein of the present invention, or a salt of the compound.

In addition, the antibody of the present invention is useful as a reagent for screening the compound or its salt that promotes or inhibits expression of the protein of the present invention.

The present invention provides (5) a method of screening a compound or its salt that promotes or inhibits expression of the protein of the present invention (hereinafter sometimes merely referred to as the promoter or the inhibitor, respectively), which comprises using the antibody of the present invention. More specifically, the present invention provides, for example:

(6) a method of screening the promoter or the inhibitor, which comprises comparing (v) the case where cells capable of producing the protein of the present invention are cultured and (vi) the case where a mixture of cells capable of producing the protein of the present invention and a test compound is cultured.

In the screening method described above, for example, the expression level of the protein of the present invention (specifically, the level of the protein of the present invention) is determined (e.g., detection of expression of the protein of the present invention, quantification of the expression level of the protein of the present invention, etc.) in the cases (v) and (vi) using the antibody of the present invention, and comparison is made therebetween.

For the test compound, for example, peptides, proteins, non-peptide compounds, synthetic compounds, fermentation products, cell extracts, plant extracts, animal tissue extracts, and the like are used. These compounds may be novel or known compounds.

To perform the screening method described above, cells capable of producing the protein of the present invention are suspended in a buffer suitable for the screening to prepare the cell suspension. Any buffer is usable so long as it is a buffer such as a phosphate buffer, borate buffer, etc. having pH of approximately 4 to 10 (preferably pH of about 6 to about 8), which does not interfere the expression of the protein of the present invention.

As the cells capable of producing the protein of the present invention, there is used, e.g., the aforesaid host (transformant) transformed with a vector containing the DNA encoding the protein of the present invention. Preferably, animal cells such as CHO cells, etc. are used as the host. For the screening, the transformant, in which the protein of the present invention has been expressed on the membrane such as endoplasmic reticulum membrane, Golgi membrane, cell membrane, etc., for example, by culturing through the procedure described above, is preferably employed.

The level of the protein of the present invention can be determined by publicly known methods, e.g., by measuring the aforesaid protein present in the cell extract, etc., using an antibody capable of recognizing the protein of the present invention, in accordance with methods like western blot analysis, ELISA, etc., or their modifications.

For example, when a test compound promotes the expression level of the protein of the present invention in the case (vi) described above by at least about 20%, preferably at least 30%, more preferably at least about 50%, as compared to the case (v) described above, the test compound can be selected to be a compound capable of promoting the expression of the protein of the present invention, or a salt of the compound.

For example, when a test compound inhibits the expression level of the protein of the present invention in the case (vi) described above by at least about 20%, preferably at least 30%, more preferably at least about 50%, as compared to the case (v) described above, the test compound can be selected to be a compound capable of inhibiting the expression of the protein of the present invention, or a salt of the compound.

The screening kit of the present invention comprises the protein or partial peptide used in the present invention or a salt thereof, or the cell capable of producing the protein used in the present invention or its partial peptide.

The compound or its salt obtained using the screening method or screening kit of the present invention is the test compound described above, the compound selected from, for example, peptides, proteins, non-peptide compounds, synthetic compounds, fermentation products, cell extracts, plant extracts, animal tissue extracts, plasma, etc., which is a compound or its salt that promotes or inhibits the activity of the protein (e.g., organic anion transport activity) of the present invention.

The salts of these compounds used are those given above as the salts of the protein of the present invention.

The compound or its salt that promotes the activity of the protein of the present invention is useful as a pharmaceutical for example a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound or its salt is used preferably as a prophylactic/therapeutic agent for renal diseases and thyroid hormone-related diseases, more preferably as a prophylactic/therapeutic agent for diabetic nephropathy.

The compound or its salt that inhibits the activity of the protein of the present invention is useful as a pharmaceutical for example a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound or its salt is used preferably as a prophylactic/therapeutic agent for renal diseases and thyroid hormone-related diseases, more preferably as a prophylactic/therapeutic agent for diabetic nephropathy.

The compound or its salt that promotes the expression of a gene for the protein of the present invention is useful as a pharmaceutical for example a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound or its salt is used preferably as a prophylactic/therapeutic agent for renal diseases and thyroid hormone-related diseases, more preferably as a prophylactic/therapeutic agent for diabetic nephropathy.

The compound or its salt that inhibits the expression of a gene for the protein of the present invention is useful as a pharmaceutical for example a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound or its salt is used preferably as a prophylactic/therapeutic agent for renal diseases and thyroid hormone-related diseases, more preferably as a prophylactic/therapeutic agent for diabetic nephropathy.

The compound or its salt that promotes the expression of the protein of the present invention is useful as a pharmaceutical for example a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound or its salt is used preferably as a prophylactic/therapeutic agent for renal diseases and thyroid hormone-related diseases, more preferably as a prophylactic/therapeutic agent for diabetic nephropathy.

The compound or its salt that inhibits the expression of the protein of the present invention is useful as a pharmaceutical for example a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound or its salt is used preferably as a prophylactic/therapeutic agent for renal diseases and thyroid hormone-related diseases, more preferably as a prophylactic/therapeutic agent for diabetic nephropathy.

As the compounds or salt thereof obtained by the screening methods or screening kits of the present invention, preferred are compounds or salts thereof that promote the activity of the protein of the present invention, compound or salts thereof that promote the expression of a gene for the protein of the present invention, and compounds or salts thereof that promote the expression of the protein of the present invention.

When the compounds or their salt forms obtained by the screening methods or screening kits of the present invention are used as agents for the prevention/treatment described above, pharmaceutical preparations can be prepared following the conventional methods. For example, the compounds can be prepared into tablets, capsules, elixir, microcapsules, aseptic solution, suspension, etc.

Since the thus obtained pharmaceutical preparation is safe and low toxic, the preparation can be administered orally or parenterally to human or warm-blooded animals (e.g., mice, rats, rabbits, sheep, swine, bovine, horses, fowl, cats, dogs, monkeys, chimpanzees, etc.).

The dose of the compound or its salt may vary depending upon target disease, subject to be administered, route of administration, etc. In oral administration of the compound or its salt that promotes the activity of the protein of the present invention for the treatment of, e.g., renal insufficiency, generally the compound or its salt is administered to an adult (as 60 kg body weight) in a dose of about 0.1 mg to 100 mg, preferably about 1.0 to 50 mg and more preferably about 1.0 to 20 mg per day. In parenteral administration, the single dose of the compound or its salt may vary depending on subject to be administered, target disease, etc. When the compound or its salt that promotes the activity of the protein of the present invention is administered to an adult (as 60 kg body weight) in the form of injectable preparations for the treatment of, e.g., renal insufficiency, it is advantageous to inject the compound or its salt intravenously in a daily dose of about 0.01 to about 30 mg, preferably about 0.1 to about 20 mg and more preferably about 0.1 to about 10 mg. For other animal species, the corresponding dose as converted per 60 kg can be administered.

[3] Quantification for the Protein of the Present Invention, it Partial Peptide or Salts Thereof The antibody of the present invention is capable of specifically recognizing the protein of the present invention, and thus can be used for quantification of the protein of the present invention in a test sample fluid, in particular, for quantification by sandwich immunoassay; etc.

That is, the present invention provides:
(i) a method for quantification of the protein of the present invention in a test sample fluid, which comprises competitively reacting the antibody of the present invention, a test sample fluid and a labeled form of the protein of the present invention, and measuring the ratio of the labeled form of the protein of the present invention bound to the antibody; and,
(ii) a method for quantification of the protein of the present invention in a test sample fluid, which comprises reacting a test sample fluid simultaneously or continuously with the antibody of the present invention immobilized on a carrier and another labeled antibody of the present invention, and then measuring the activity of the labeling agent on the insoluble carrier.

In the quantification method (ii) described above, it is preferred that one antibody is capable of recognizing the N-terminal region of the protein of the present invention, while another antibody is capable of reacting with the C-terminal region of the protein of the present invention.

The monoclonal antibody to the protein of the present invention (hereinafter sometimes referred to as the monoclonal antibody of the present invention) can be used to quantify the protein of the present invention. In addition, the protein can be detected by means of a tissue staining as well. For these purposes, the antibody molecule per se may be used or $F(ab')_2$, Fab' or Fab fractions of the antibody molecule may also be used.

The method for quantification of the protein of the present invention using the antibody of the present invention is not particularly limited. Any quantification method can be used, so long as the amount of antibody, antigen or antibody-antigen complex corresponding to the amount of antigen (e.g., the amount of the protein) in a test sample fluid can be detected by chemical or physical means and the amount of the antigen can be calculated from a standard curve prepared from standard solutions containing known amounts of the antigen. For such an assay method, for example, nephrometry, the competitive method, the immunometric method, the sandwich method, etc. are suitably used and in terms of sensitivity and specificity, it is particularly preferred to use the sandwich method described hereinafter.

Examples of the labeling agent used in the assay method using the labeling substance are radioisotopes, enzymes, fluorescent substances, luminescent substances, and the like. As the radioisotopes, there are used, e.g., $[^{125}I]$, $[^{131}I]$, $[^{3}H]$, $[^{14}C]$, etc. The enzymes described above are preferably enzymes, which are stable and have a high specific activity, and include, e.g., beta-galactosidase, beta-glucosidase, an alkaline phosphatase, a peroxidase, malate dehydrogenase, etc. As the fluorescent substances, there are used, e.g., fluorescamine, fluorescein isothiocyanate, etc. As the luminescent substances described above there are used, e.g., luminol, a luminol derivative, luciferin, lucigenin, etc. Furthermore, the biotin-avidin system may be used as well for binding of an antibody or antigen to a labeling agent.

For immobilization of the antigen or antibody, physical adsorption may be used. Chemical binding techniques conventionally used for insolubilization or immobilization of proteins, enzymes, etc. may also be used. For carriers, there are used, e.g., insoluble polysaccharides such as agarose, dextran, cellulose, etc.; synthetic resin such as polystyrene, polyacrylamide, silicon, etc., and glass or the like.

In the sandwich method, the immobilized monoclonal antibody of the present invention is reacted with a test fluid (primary reaction), then with a labeled form of another monoclonal antibody of the present invention (secondary reaction), and the activity of the label on the immobilizing carrier is measured, whereby the amount of the protein of the present invention in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of assaying the protein of the present invention by the sandwich method, antibodies that bind to different sites of the protein of the present invention are preferably used as the monoclonal antibodies of the present invention used for the primary and secondary reactions. That is, in the antibodies used for the primary and secondary reactions are, for example, when the antibody used in the secondary reaction recognizes the C-terminal region of the protein of the present invention, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, the competitive method, the immunometric method, nephrometry, etc.

In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these immunological methods to the measurement methods of the present invention, any particular conditions or procedures are not required. Systems for measuring the protein of the present invention or its salts are constructed by adding the usual technical consideration in the art to the conventional conditions and procedures. For the details of these general technical means, reference can be made to the following reviews and texts.

For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing).

As described above, the protein of the present invention can be quantified with high sensitivity, using the antibody of the present invention.

Furthermore, when a decreased level of the protein of the present invention is detected by quantifying the level of the protein of the present invention using the antibody of the present invention, it can be diagnosed that it is highly likely to suffer from diseases, for example, renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. On the other hand, when an increased level of the protein of the present invention is detected, it can be diagnosed that it is highly likely to suffer from diseases, for example, renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc.

Moreover, the antibody of the present invention can be used to detect the protein of the present invention, which is present in a test sample fluid such as a body fluid, a tissue, etc. The antibody can also be used to prepare an antibody column for purification of the protein of the present invention, detect the protein of the present invention in each fraction upon purification, analyze the behavior of the protein of the present invention in the cells under investigation; etc.

[4] Gene Diagnostic Agent

By using the DNA of the present invention, e.g., as a probe, an abnormality (gene abnormality) of the DNA or mRNA encoding the protein of the present invention or its partial peptide in human or warm-blooded animal (e.g., rat, mouse, guinea pig, rabbit, fowl, sheep, swine, bovine, horse, cat, dog, monkey, chimpanzee, etc.) can be detected. Therefore, the DNA of the present invention is useful as a gene diagnostic agent for detecting damages to the DNA or mRNA, its mutation, or decreased expression, increased expression, overexpression, etc. of the DNA or mRNA, and so on.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)), etc.

When increased expression of the gene for the protein of the present invention is detected, e.g., by the Northern hybridization, it can be diagnosed that it is highly likely to suffer from diseases, for example, renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.) etc. On the other hand, when decreased expression of the gene is detected or DNA mutation is detected by the PCR-SSCP assay, it can be diagnosed that it is highly likely to suffer from diseases, for example, renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc.

[5] A Pharmaceutical (Medicine, Drug or Pharmaceutical Preparation) and a Diagnostic Agent Comprising the Antisense Polynucleotide The antisense polynucleotide of the present invention that can bind complementarily to the DNA of the present invention to inhibit expression of the DNA is low toxic and can suppress the functions (e.g., the transport of organic anions) of the protein of the present invention or the DNA of the present invention, and thus the antisense polynucleotide can be used as agents for the prevention/treatment of diseases, for example, renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The antisense polynucleotide is used preferably as a prophylactic/therapeutic agent for renal diseases and thyroid hormone-related diseases, more preferably as a prophylactic/therapeutic agent for diabetic nephropathy. The antisense polynucleotide of the present invention is also used for diagnosis of the diseases described above.

When the antisense polynucleotide is used as the aforesaid prophylactic/therapeutic agent, it can be formed into a medicine and administered in publicly known methods.

For example, when the antisense polynucleotide is used, the antisense polynucleotide itself, or the antisense polynucleotide inserted into an appropriate vector such as retrovirus vector, adenovirus vector, adenovirus-associated virus vector, etc., is administered orally or parenterally to human or other warm-blooded animal (e.g., rat, rabbit, sheep, swine, bovine, cat, dog, monkey, etc.) in a conventional manner. The antisense polynucleotide may also be administered as it is, or prepared into medicines together with physiologically acceptable carriers such as adjuvants to assist its uptake, and such preparations are administered by gene gun or through a catheter like a hydrogel catheter.

The dose of the antisense polynucleotide may vary depending upon target disease, subject to be administered, route for administration, etc. When the antisense polynucleotide is administered topically to the kidney, the antisense polynucleotide is administered to adult (60 kg body weight) usually in a daily dose of approximately 0.1 to 100 mg.

In addition, the antisense polynucleotide may also be employed as an oligonucleotide probe for diagnosis to examine the presence of the DNA of the present invention in tissues or cells, or the states of its expression.

Further, the present invention provides:

(i) double-stranded RNA comprising a part of RNA encoding the protein of the present invention and RNA complementary thereto, (ii) a medicine comprising the double-stranded RNA, (iii) ribozyme comprising a part of RNA encoding the protein of the present invention, (iv) a medicine comprising the ribozyme, and (v) an expression vector comprising a gene (DNA) encoding the ribozyme.

Similar to the antisense polynucleotide, the double-stranded RNA and ribozyme can also disrupt RNA transcribed from the DNA of the present invention or can suppress its functions to suppress the in vivo function of the protein of the present invention or the DNA used in the present invention, and can thus be used as agents for the prevention/treatment of, for example, renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The double-stranded RNA and ribozyme are used preferably as a prophylactic/therapeutic agent for renal diseases and thyroid hormone-related diseases, more preferably as a prophylactic/therapeutic agent for diabetic nephropathy.

The double-stranded RNA can be designed based on a sequence of the polynucleotide of the present invention and manufactured by modifications of publicly known methods (e.g., Nature, 411, 494, 2001).

The ribozyme can be designed based on a sequence of the polynucleotide of the present invention and manufactured by modifications of publicly known methods (e.g., TRENDS in Molecular Medicine, 7, 221, 2001). For example, the ribozyme can be manufactured by replacing a part of the RNA encoding the protein of the present invention for a part of publicly known ribozyme. A part of the RNA encoding the protein of the present invention includes sequences near the consensus sequence NUX (wherein N represents all bases and X represents bases other than G), etc., which can be cleaved by a publicly known ribozyme.

Where the double-stranded RNA or ribozyme described above is used as the prophylactic/therapeutic agent described above, it can be prepared into a pharmaceutical preparation and administered in the same manner as for the antisense polynucleotide. Also, the expression vector described in (v) above is used in a similar way to publicly known gene therapy, etc. and used as the prophylactic/therapeutic agent described above.

[6] Pharmaceutical Comprising the Antibody of the Present Invention

The antibody of the present invention having an activity of neutralizing the activity of the protein of the present invention can be used as a prophylactic/therapeutic agent for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The antibody of the present invention is used preferably as a prophylactic/therapeutic agent for renal diseases and thyroid hormone-related diseases, more preferably as a prophylactic/therapeutic agent for diabetic nephropathy.

Since the prophylactic/therapeutic agent comprising the antibody of the present invention is safe and low toxic, it can be administered orally or parenterally (for example, administration into joint) to humans or other mammals (e.g., rat, rabbit, sheep, swine, bovine, cat, dog, monkey, etc.). The dose may vary depending on subject to be administered, target disease, symptom, route of administration, etc. When the prophylactic/therapeutic agent is used for therapy/prevention of diabetic nephropathy, it is convenient to administer the antibody of the present invention via an intravenous injection to adult usually in a single dose of approximately 0.01 to 20 mg/kg weight, preferably approximately 0.1 to 10 mg/kg weight, preferably approximately 0.1 to 5 mg/kg weight, once to 5 times every day, preferably once to thrice every day. When the antibody is administered by other parenteral administration or oral administration, the corresponding dose can be administered. When the symptom is particularly severe, the dose may be increased depending on the symptom.

The antibody of the present invention can be administered as it is or as a suitable pharmaceutical composition. The pharmaceutical composition used in the above administration comprises the above antibody or its salts, a pharmacologically acceptable carrier, diluent or excipient. The composition is provided in a preparation form adapted to oral or parenteral administration (for example, injection into veins or joints). Preferably, it is provided as an inhalation.

Each of the compositions described above may comprise other active ingredients insofar as the ingredients, upon blending with the antibody, do not generate undesirable interaction.

[7] Preparation of Animal Bearing the DNA of the Present Invention

The present invention provides a non-human mammal bearing DNA encoding the protein of the present invention, which is exogenous (hereinafter abbreviated as the exogenous DNA of the present invention) or its variant DNA (sometimes simply referred to as the exogenous variant DNA of the present invention).

That is, the present invention provides:
(1) A non-human mammal bearing the exogenous DNA of the present invention or its variant DNA;
(2) The mammal according to (1), wherein the non-human mammal is a rodent;
(3) The mammal according to (2), wherein the rodent is mouse or rat; and,
(4) A recombinant vector containing the exogenous DNA of the present invention or its variant DNA and capable of expressing in a mammal; etc.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57BL/6 strain, DBA2 strain, etc. for a pure line and for a cross line, B6C3F$_1$ strain, BDF$_1$ strain B6D2F$_1$ strain, BALB/c strain, ICR strain, etc.), rats (Wistar, SD, etc.) or the like, since they are relatively short in ontogeny and life cycle from a standpoint of creating model animals for human disease.

"Mammals" in a recombinant vector that can be expressed in the mammals include the aforesaid non-human mammals and human.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean DNA that expresses the abnormal protein of the present invention and exemplified by the DNA that expresses a protein for suppressing the function of the normal protein of the present invention, etc.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the protein of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating expression of the DNA described above include (1) promoters for DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human protein elongation factor 1α (EF-1α) promoters, human and chicken β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of increasing expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal protein of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal polypeptide obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by crossing.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygotic animals having the transfected DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the protein of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the protein of the present invention and the pathological mechanism of the disease associated with the protein of the present invention and to investigate how to treat these diseases.

Furthermore, since a mammal transfected with the exogenous normal DNA of the present invention exhibits an increasing symptom of the protein of the present invention liberated, the animal is usable for screening of an agent for the treatment of diseases associated with the protein of the present invention.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the target mammal. The fact that the abnormal DNA of the present invention is present in the germinal cells of the animal after DNA transfection means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the protein of the present invention by inhibiting the functions of endogenous normal DNA. Therefore, the animal can be utilized as a pathologic model animal for such a disease. For example, using the abnormal DNA transgenic animal of the present invention, it is possible to elucidate the mechanism of the function inactive type inadaptability to the protein of the present invention and the pathological mechanism of the disease associated with the protein of the present invention and to investigate how to treat the disease.

More specifically, the transgenic animal of the present invention expressing the abnormal DNA of the present invention at a high level is expected to serve as an experimental model to elucidate the mechanism of the functional inhibition (dominant negative effect) of a normal protein by the abnormal protein of the present invention in the function inactive type inadaptability of the protein of the present invention.

A mammal bearing the abnormal exogenous DNA of the present invention is also expected to serve in screening a candidate drug for the treatment of the function inactive type inadaptability of the protein of the present invention, since a free form of the protein of the present invention is increased in such an animal.

Other potential applications of two kinds of the DNA transgenic animals of the present invention described above further include:

(i) Use as a cell source for tissue culture;
(ii) Elucidation of the relation to a protein that is specifically expressed or activated by the protein of the present invention, by direct analysis of DNA or RNA in tissues of the DNA transgenic animal of the present invention or by analysis of the polypeptide tissues expressed by the DNA;
(iii) Research on the function of cells derived from tissues that are usually cultured only with difficulty, using cells in tissues bearing the DNA cultured by a standard tissue culture technique;
(iv) Screening a drug that enhances the functions of cells using the cells described in (iii) above; and,
(v) Isolation and purification of the variant protein of the present invention and preparation of an antibody thereto; etc.

Furthermore, clinical conditions of a disease associated with the protein of the present invention, including the function inactive type inadaptability to the protein of the present invention can be determined by using the DNA transgenic animal of the present invention. Also, pathological findings on each organ in a disease model associated with the protein of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the protein of the present invention, and to study in association with apoptosis, differentiation or propagation or on the mechanism of signal transduction in these properties to inspect any abnormality therein. Thus, the DNA transgenic animal can provide an effective research material for the protein of the present invention and for investigation of the function and effect thereof.

To develop a drug for the treatment of diseases associated with the protein of the present invention, including the function inactive type inadaptability to the protein of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the protein of the present invention, using the DNA transgenic animal of the present invention or a vector capable of expressing the exogenous DNA of the present invention.

[8] Knockout Animal

The present invention provides a non-human mammal embryonic stem cell bearing the DNA of the present invention inactivated and a non-human mammal deficient in expressing the DNA of the present invention.

Thus, the present invention provides:

(1) A non-human mammal embryonic stem cell in which the DNA of the present invention is inactivated;
(2) The embryonic stem cell according to (1), wherein the DNA is inactivated by introducing a reporter gene (e.g., β-galactosidase gene derived from *Escherichia coli*);
(3) The embryonic stem cell according to (1), which is resistant to neomycin;
(4) The embryonic stem cell according to (1), wherein the non-human mammal is a rodent;
(5) The embryonic stem cell according to (4), wherein the rodent is mouse;
(6) A non-human mammal deficient in expressing the DNA of the present invention, wherein the DNA is inactivated;
(7) The non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;
(8) The non-human mammal according to (6), which is a rodent;
(9) The non-human mammal according to (8), wherein the rodent is mouse; and,
(10) A method of screening a compound that promotes or inhibits the promoter activity to the DNA of the present invention, which comprises administering a test compound to the mammal of (7) and detecting expression of the reporter gene.

The non-human mammal embryonic stem cell in which the DNA of the present invention is inactivated refers to a non-human mammal embryonic stem cell that suppresses the capability of the non-human mammal to express the DNA by artificially mutating the DNA of the present invention, or the DNA has no substantial capability to express the protein of the present invention (hereinafter sometimes referred to as the knockout DNA of the present invention) by substantially inactivating the activities of the protein of the present invention encoded by the DNA (hereinafter merely referred to as ES cell).

As the non-human mammal used, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually disrupting the gene (hereinafter simply referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, a first selection of ES cells at the early stage of culture can be based on sex identification, and male cells can be selected early, which saves a significant amount of time at the early stage of culture.

Also, a second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for studying the function of the protein of the present invention cytologically.

The non-human mammal deficient in expression of the DNA of the present invention can be identified from a normal animal by measuring the mRNA level in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transfecting a targeting vector, prepared as described above, to mouse embryonic stem cells or mouse oocytes, and conducting homologous recombination in which a targeting vector DNA sequence, wherein the DNA of the present invention is inactivated by the transfection, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyte, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the protein of the present invention. The individuals deficient in homozygous expression of the protein of the present invention can be obtained from offspring of the intercross between those deficient in heterozygous expression of the protein of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is rendered knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygote animals having the inactivated DNA in both loci can be obtained. The homozygotes thus obtained may be reared so that one normal animal and a plurality of homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the protein of the present invention, such an animal can be a disease model suspected of inactivated biological activities of the protein of the present invention and thus, offers an effective study to investigate the causes for and therapy for these diseases.

[8a] Method of Screening a Compound having a Therapeutic/Preventive Effect on Diseases Caused by Deficiency, Damages, etc. of the DNA of the Present Invention The non-human mammal deficient in expression of the DNA of the present invention can be employed for screening of a compound having a therapeutic/preventive effect on diseases caused by deficiency, damages, etc. of the DNA of the present invention.

That is, the present invention provides a method of screening a compound having a therapeutic/preventive effect on diseases caused by deficiency, damages, etc. of the DNA of the present invention, which comprises administering a test compound to a non-human mammal deficient in expression of the DNA of the present invention and, observing and measuring a change occurred in the animal.

As the non-human mammal deficient in expression of the DNA of the present invention, which can be employed in the screening method, the same examples as given hereinabove apply.

Examples of the test compound include peptides, proteins, non-peptide compounds, synthetic compounds, fermentation products, cell extracts, plant extracts, animal tissue extracts, blood plasma, etc. These compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/preventive effects of the test compound.

For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately selected depending on the administration route, nature of the test compound, etc.

For screening of the compound having a therapeutic effect on, e.g., renal insufficiency, a test compound is given to the non-human mammal deficient in expression of the DNA encoding the protein of the present invention, and the amount of creatinine in blood and protein in urine are measured with passage of time.

The compound obtained using the above screening method is a compound selected from the test compounds described above and exhibits a preventive/therapeutic effect on diseases caused by deficiencies, damages, etc. of the protein of the present invention. Therefore, the compound can be employed as a safe and low toxic drug for the prevention/treatment of the diseases. Furthermore, compounds derived from the compound obtained by the screening described above may also be used as well.

The compound obtained by the screening method above may form salts, and may be used in the form of salts with physiologically acceptable acids (e.g., inorganic acids, organic acids, etc.) or bases (e.g., alkali metal salts), particularly preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical comprising the compound obtained by the above screening method or salts thereof can be manufactured in a manner similar to the method for preparing the pharmaceutical comprising the protein of the present invention described hereinabove.

Since the pharmaceutical preparation thus obtained is safe and low toxic, it can be administered to human or mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound is orally administered to an adult (as 60 kg body weight), generally the compound is administered to the patient with, e.g., renal insufficiency in a daily dose of about 0.1 to about 100 mg, preferably about 1.0 to about 50 mg and, more preferably about 1.0 to about 20 mg. In parenteral administration, a single dose of the compound may vary depending upon target subject, target disease, etc. When the compound is administered to an adult (as 60 kg) patient with renal insufficiency in the form of an injectable preparation, it is advantageous to administer the compound intravenously to the patient in a daily dose of about 0.01 to about 30 mg, preferably about 0.1 to about 20 mg, and more preferably about 0.1 to about 10 mg. For other animal species, the corresponding dose as converted per 60 kg can be administered.

[8b] Method of Screening a Compound that Promotes or Inhibits the Activity of a Promoter to the DNA of the Present Invention The present invention provides a method of screening a compound or its salts that promote or inhibit the activity of a promoter to the DNA of the present invention, which comprises administering a test compound to a non-human mammal deficient in expression of the DNA of the present invention and detecting expression of the reporter gene.

In the screening method described above, an animal in which the DNA of the present invention is inactivated by introducing a reporter gene and the reporter gene is expressed under control of a promoter to the DNA of the present invention is used as the non-human mammal deficient in expression of the DNA of the present invention, which is selected from the aforesaid non-human mammals deficient in expression of the DNA of the present invention.

The same examples of the test compound apply to specific compounds used for the screening.

As the reporter gene, the same specific examples apply to this screening method. Preferably, there are used β-galactosidase (lacZ), soluble alkaline phosphatase gene, luciferase gene and the like.

Since the reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the protein of the present invention is substituted with, e.g., β-galactosidase gene (lacZ) derived from *Escherichia coli*, β-galactosidase is expressed in a tissue where the protein of the present invention should originally be expressed, instead of the protein of the present invention. Thus, the state of expression of the protein of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the protein of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method described above are compounds that are screened from the test compounds described above and that promote or inhibit the promoter activity to the DNA of the present invention.

The compound obtained by the screening method above may form salts, and may be used in the form of salts with physiologically acceptable acids (e.g., inorganic acids, etc.) or bases (e.g., organic acids, etc.) or the like, especially in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salt that promotes the promoter activity to the DNA of the present invention can promote expression of the protein of the present invention to promote the function of the protein, and thus the compound or its salt is useful as pharmaceuticals such as agents for the prevention/treatment of diseases, for example, renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound or its salt is used preferably as a prophylactic/therapeutic agent for renal diseases and thyroid hormone-related diseases, more preferably as a prophylactic/therapeutic agent for diabetic nephropathy.

Further, the compound or its salt that inhibits the promoter activity to the DNA of the present invention can inhibit expression of the protein of the present invention to inhibit the function of the protein, and thus the compound or its salt is useful as pharmaceuticals such as agents for the prevention/treatment of diseases, for example, renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound or its salt is used preferably as a prophylactic/therapeutic agent for renal diseases and thyroid hormone-related diseases, more preferably as a prophylactic/therapeutic agent for diabetic nephropathy.

In the above compounds, preferred are compounds or salts thereof that promote the promoter activity with respect to the DNA of the present invention.

In addition, compounds derived from the compound obtained by the screening described above may also be used as well.

A pharmaceutical comprising the compound obtained by the above screening method or salts thereof can be manufactured in a maimer similar to the method for preparing the pharmaceutical comprising the protein of the present invention or its salts described hereinabove.

Since the pharmaceutical preparation thus obtained is safe and low toxic, it can be administered to human or mammal (e.g., rat, mouse, guinea pig, rabbit, sheep, swine, bovine, horse, cat, dog, monkey, etc.).

A dose of the compound or salts thereof may vary depending on target disease, subject to be administered, route for administration, etc.; when the compound that promotes the promoter activity to the DNA of the present invention is orally administered to an adult (as 60 kg body weight), the compound is administered to the patient with renal insufficiency normally in a daily dose of about 0.1 to 100 mg, preferably about 1.0 to 50 mg and more preferably about 1.0 to 20 mg. In parenteral administration, a single dose of the compound varies depending on subject to be administered, target disease, etc. but when the compound of promoting the promoter activity to the DNA of the present invention is administered to an adult (as 60 kg) in the form of injectable preparation, it is advantageous to administer the compound intravenously to the patient with renal insufficiency in a daily dose of about 0.01 to about 30 mg, preferably about 0.1 to about 20 mg and more preferably about 0.1 to about 10 mg. For other animal species, the corresponding dose as converted per 60 kg can be administered.

On the other hand, when the compound that inhibits the promoter activity to the DNA of the present invention is orally administered an adult (as 60 kg body weight), the compound is administered to the patient with renal insufficiency normally in a daily dose of about 0.1 to 100 mg, preferably about 1.0 to 50 mg and more preferably about 1.0 to 20 mg. In parenteral administration, a single dose of the compound varies depending on subject to be administered, target disease, etc. but when the compound of inhibiting the promoter activity to the DNA of the present invention is administered to an adult (as 60 kg) in the form of injectable preparation, it is advantageous to administer the compound intravenously to the patient with renal insufficiency in a daily dose of about 0.01 to about 30 mg, preferably about 0.1 to about 20 mg and more preferably about 0.1 to about 10 mg. For other animal species, the corresponding dose as converted per 60 kg can be administered.

As stated above, the non-human mammal deficient in expression of the DNA of the present invention is extremely useful for screening the compound or its salt that promotes or inhibits the promoter activity to the DNA of the present invention and, can greatly contribute to elucidation of causes for various diseases suspected of deficiency in expression of the DNA of the present invention and for the development of preventive/therapeutic agent for these diseases.

Also, a so-called transgenic animal (gene transferred animal) can be prepared by using a DNA containing the promoter region of the DNA of the present invention, ligating genes encoding various proteins at the downstream and injecting the same into oocyte of an animal. It is thus possible to synthesize the polypeptide therein specifically and study its activity in vivo. When an appropriate reporter gene is ligated to the promoter site described above and a cell line that expresses the gene is established, the resulting system can be utilized as the search system for a low molecular compound having the action of specifically promoting or inhibiting the in vivo productivity of the protein of the present invention itself.

In the specification and drawings, the codes of bases, amino acids, etc. are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| lie | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gin | glutamine |
| pGlu | pyroglutamic acid |

Substituents, protecting groups and reagents generally used in this specification are presented as the codes below.

| | |
|---|---|
| Me | methyl group |
| Et | ethyl group |
| Bu | butyl group |
| Ph | phenyl group |
| TC | thiazolidine-4(R)-carboxamido group |
| Tos | p-toluenesulfonyl |
| CHO | formyl |
| Bzl | benzyl |
| Cl$_2$-Bzl | 2,6-dichlorobenzyl |
| Bom | benzyloxymethyl |
| Z | benzyloxycarbonyl |
| Cl-Z | 2-chlorobenzyloxycarbonyl |
| Br-Z | 2-bromobenzyl oxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyirnide |
| DCC | N,N'-dicyclohexylcarbodiimide |

The sequence identification numbers in the sequence listing of the specification indicates the following sequence, respectively.

[SEQ ID NO. 1]
This shows the amino acid sequence of human TCH229 protein obtained in Example 3.

[SEQ ID NO: 2]
This shows the nucleotide sequence of DNA encoding human TCH229 protein having the amino acid sequence represented by SEQ ID NO. 1.

[SEQ ID NO: 3]
This shows the nucleotide sequence of primer AP1 used in Examples 1, 2, 5, 6, 9 and 10.

[SEQ ID NO: 4]
This shows the nucleotide sequence of primer rr1 used in Examples 1, 3 and 15.

[SEQ ID NO: 5]
This shows the nucleotide sequence of primer AP2 used in Examples 1, 2, 5, 6, 9 and 10.

[SEQ ID NO: 6]
This shows the nucleotide sequence of primer rr2 used in Examples 1, 3 and 15.

[SEQ ID NO: 7]
This shows the nucleotide sequence of primer rr3 used in Example 1.

[SEQ ID NO: 8]
This shows the nucleotide sequence of primer rr4 used in Example 1.

[SEQ ID NO: 9]
This shows the nucleotide sequence of primer ff1 used in Examples 2, 3 and 15.

[SEQ ID NO: 10]
This shows the nucleotide sequence of primer ff2 used in Examples 2, 3 and 15.

[SEQ ID NO: 11]
This shows the nucleotide sequence of primer ORFF1 used in Example 3.

[SEQ ID NO: 12]
This shows the nucleotide sequence of primer ORFR1 used in Example 3.

[SEQ ID NO: 13]
This shows the nucleotide sequence of primer ORFF2 used in Example 3.

[SEQ ID NO: 14]
This shows the nucleotide sequence of primer ORFR2 used in Example 3.

[SEQ ID NO: 15]
This shows the nucleotide sequence of primer M13F used in Examples 3 and 7.

[SEQ ID NO: 16]
This shows the nucleotide sequence of primer M13R used in Examples 3 and 7.

[SEQ ID NO: 17]
This shows the nucleotide sequence of primer A1 used in Examples 3 and 15.

[SEQ ID NO: 18]
This shows the nucleotide sequence of primer B2 used in Examples 3 and 15.

[SEQ ID NO: 19]
This shows the nucleotide sequence of primer TMF used in Examples 4, 16 and 17.

[SEQ ID NO: 20]
This shows the nucleotide sequence of primer TMR used in Examples 4, 16 and 17.

[SEQ ID NO: 21]
This shows the nucleotide sequence of TaqMan probe P1 used in Examples 4, 16 and 17.

[SEQ ID NO: 22]
This shows a nucleotide sequence obtained in Example 1.

[SEQ ID NO: 23]
This shows a nucleotide sequence obtained in Example 1.

[SEQ ID NO: 24]
This shows a nucleotide sequence obtained in Example 2.

[SEQ ID NO: 25]
This shows a nucleotide sequence obtained in Example 3.

[SEQ ID NO: 26]
This shows the amino acid sequence of mouse TCH229 protein obtained in Example 7.

[SEQ ID NO: 27]
This shows the nucleotide sequence of DNA encoding mouse TCH229 protein having the amino acid sequence presented by SEQ ID NO: 26.

[SEQ ID NO: 28]
This shows the nucleotide sequence of a primer used in Examples 5 and 7.

[SEQ ID NO: 29]
This shows the nucleotide sequence of a primer used in Examples 5 and 7.

[SEQ ID NO: 30]
This shows the nucleotide sequence of a primer used in Example 5.

[SEQ ID NO: 31]
This shows the nucleotide sequence of a primer used in Examples 5 and 7.

[SEQ ID NO: 32]
This shows the nucleotide sequence of a primer used in Examples 6 and 7.

[SEQ ID NO: 33]
This shows the nucleotide sequence of a primer used in Examples 6 and 7.

[SEQ ID NO: 34]
This shows the nucleotide sequence of a primer used in Example 7.

[SEQ ID NO: 35]
This shows the nucleotide sequence of a primer used in Example 7.

[SEQ ID NO: 36]
This shows the nucleotide sequence of a primer used in Example 7.

[SEQ ID NO: 37]
This shows the nucleotide sequence of a primer used in Example 7.

[SEQ ID NO: 38]
This shows the nucleotide sequence of a primer used in Example 7.

[SEQ ID NO: 39]
This shows the nucleotide sequence of a primer used in Example 7.

[SEQ ID NO: 40]
This shows the nucleotide sequence of a primer used in Example 7.

[SEQ ID NO: 41]
This shows the nucleotide sequence of a primer used in Example 7.

[SEQ ID NO: 42]
This shows the nucleotide sequence of a primer used in Example 7.

[SEQ ID NO: 43]
This shows the nucleotide sequence of a primer used in Example 7.

[SEQ ID NO: 44]
This shows the nucleotide sequence of a primer used in Example 7.

[SEQ ID NO: 45]
This shows the nucleotide sequence of a primer used in Examples 8 and 13.

[SEQ ID NO: 46]
This shows the nucleotide sequence of a primer used in Examples 8 and 13.

[SEQ ID NO: 47]
This shows the nucleotide sequence of a probe used in Examples 8 and 13.

[SEQ ID NO: 48]
This shows a nucleotide sequence obtained in Example 5.

[SEQ ID NO: 49]
This shows a nucleotide sequence obtained in Example 5.

[SEQ ID NO: 50]
This shows a nucleotide sequence obtained in Example 6.

[SEQ ID NO: 51]
This shows a nucleotide sequence obtained in Example 7.

[SEQ ID NO: 52]
This shows the amino acid sequence of rat TCH229 protein No. 1 obtained in Example 11.

[SEQ ID NO: 53]
This shows the nucleotide sequence of DNA encoding rat TCH229 protein No. 1 having the amino acid sequence presented by SEQ ID NO: 52.

[SEQ ID NO: 54]
This shows the amino acid sequence of rat TCH229 protein No. 2 obtained in Example 11.

[SEQ ID NO: 55]
This shows the nucleotide sequence of DNA encoding rat TCH229 protein No. 2 having the amino acid sequence presented by SEQ ID NO: 54.

[SEQ ID NO: 56]
This shows the nucleotide sequence of a primer used in Example 9.

[SEQ ID NO: 57]
This shows the nucleotide sequence of a primer used in Example 9.

[SEQ ID NO: 58]
This shows the nucleotide sequence of a primer used in Example 9.

[SEQ ID NO: 59]
This shows the nucleotide sequence of a primer used in Example 9.

[SEQ ID NO: 60]
This shows the nucleotide sequence of a primer used in Example 10.

[SEQ ID NO: 61]
This shows the nucleotide sequence of a primer used in Examples 10 and 11.

[SEQ ID NO: 62]
This shows the nucleotide sequence of a primer used in Example 11.

[SEQ ID NO: 63]
This shows the nucleotide sequence of a primer used in Example 11.

[SEQ ID NO: 64]
This shows the nucleotide sequence of a primer used in Example 11.

[SEQ ID NO: 65]
This shows the nucleotide sequence of a primer used in Example 11.

[SEQ ID NO: 66]
This shows the nucleotide sequence of a primer used in Examples 11 and 15.

[SEQ ID NO: 67]
This shows the nucleotide sequence of a primer used in Example 11.

[SEQ ID NO: 68]
This shows the nucleotide sequence of a primer used in Example 11.

[SEQ ID NO: 69]
This shows the nucleotide sequence of a primer used in Examples 11, 12, 14 and 18.

[SEQ ID NO: 70]
This shows the nucleotide sequence of a primer used in Examples 11, 12, 14 and 18.

[SEQ ID NO: 71]
This shows the nucleotide sequence of a primer used in Example 11.

[SEQ ID NO: 72]
This shows the nucleotide sequence of a primer used in Example 11.

[SEQ ID NO: 73]
This shows the nucleotide sequence of a primer used in Example 11.

[SEQ ID NO: 74]
This shows the nucleotide sequence of a primer used in Example 11.

[SEQ ID NO: 75]
This shows the nucleotide sequence of a primer used in Example 11.

[SEQ ID NO: 76]
This shows the nucleotide sequence of a probe used in Examples 12, 14 and 18.

[SEQ ID NO: 77]
This shows a nucleotide sequence obtained in Example 9.

[SEQ ID NO: 78]
This shows a nucleotide sequence obtained in Example 9.

[SEQ ID NO: 79]
This shows a nucleotide sequence obtained in Example 10.

[SEQ ID NO: 80]
This shows a nucleotide sequence obtained in Example 11.

[SEQ ID NO: 81]
This shows a nucleotide sequence obtained in Example 11.

[SEQ ID NO: 82]
This shows the nucleotide sequence of a primer used in Example 15.

[SEQ ID NO: 83]
This shows the nucleotide sequence of a primer used in Example 15.

[SEQ ID NO: 84]
This shows the nucleotide sequence of a primer used in Example 15.

*Escherichia coli* TOP10/pCR-BluntII-TCH229 obtained in Example 3 later described has been deposited with International Patent Organism Depositary (IPOD), National Institute of Advanced Industrial Science and Technology (AIST) at Central 6, 1-1-1, Higashi, Tsukuba, Ibaraki, Japan (zip code: 305-8566), under the Accession Number FERM BP-7983 since Mar. 27, 2002, and with Institute for Fermentation, Osaka (IFO) at 17-85, Juso-honmachi 2-chome, Yodogawa-ku, Osaka, Japan (zip code: 532-8686), under the Accession Number IFO 16767 since Mar. 12, 2002.

*Escherichia coli* TOP10/pCR2.1-mTCH229 obtained in Example 7 later described has been deposited with International Patent Organism Depositary (IPOD), National Institute of Advanced Industrial Science and Technology (AIST) at Central 6, 1-1-1, Higashi, Tsukuba, Ibaraki, Japan (zip code: 305-8566), under the Accession Number FERM BP-8076 since Jun. 13, 2002, and with Institute for Fermentation, Osaka (IFO) at 17-85, Juso-honmachi 2-chome, Yodogawa-ku, Osaka, Japan (zip code: 532-8686), under the Accession Number IFO 16800 since Jun. 4, 2002.

Hereinafter, the present invention will be specifically described by reference to the Examples, but is not limited thereto. The gene manipulation procedures using *Escherichia coli* were performed in accordance with the methods described in the Molecular Cloning.

EXAMPLE 1

Cloning of the 5'-Upstream Terminus of cDNA Encoding Human TCH229 Protein

The 5'-upstream nucleotide sequence of cDNA encoding human TCH229 protein was revealed by 5'RACE PCR cloning.

Using two primer DNAs, i.e. primer AP1 (SEQ ID NO: 3) and primer rr1 (SEQ ID NO: 4), human kidney Marathon-Ready cDNA (Clontech) was subjected to primary PCR with Advantage 2 DNA Polymerase (Clontech) under the following conditions:

(1) reaction at 94° C. for 30 seconds, and
(2) 35 cycles each consisting of reaction at 94° C. for 10 seconds and at 63° C. for 3 minutes.

Using the primary PCR product as a template, nested PCR was conducted with primer AP2 (SEQ ID NO: 5), primer rr2 (SEQ ID NO: 6) and Advantage 2 DNA Polymerase (Clontech) under the following conditions:

(3) reaction at 94° C. for 30 seconds, and
(4) 30 cycles each consisting of reaction at 94° C. for 10 seconds and at 63° C. for 3 minutes.

One (1) μl each of exonuclease I and shrimp alkaline phosphatase in PCR Product Pre-Sequencing Kit (USB) were added to 5 μl of the nested PCR reaction solution and reacted at 37° C. for 15 minutes and at 85° C. for 15 minutes. The solution was reacted by using primer AP2 (SEQ ID NO: 5), primer rr2 (SEQ ID NO: 6) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 22 was obtained.

On the basis of the nucleotide sequence represented by SEQ ID NO: 22, primer rr3 (SEQ ID NO: 7) and primer rr4 (SEQ ID NO: 8) were designed. Using primer AP1 (SEQ ID NO: 3) and primer rr3 (SEQ ID NO: 7), human kidney Marathon-Ready cDNA (Clontech) was subjected to primary PCR with Advantage 2 DNA Polymerase (Clontech) under the following conditions:

(5) reaction at 94° C. for 30 seconds, and
(6) 35 cycles each consisting of reaction at 94° C. for 10 seconds and at 63° C. for 2 minutes.

Using the primary PCR product as a template, nested PCR was conducted with primer AP2 (SEQ ID NO: 5), primer rr4 (SEQ ID NO: 8) and Advantage 2 DNA Polymerase (Clontech) under the following conditions:

(7) reaction at 94° C. for 30 seconds, and
(8) 30 cycles each consisting of reaction at 94° C. for 10 seconds and at 63° C. for 2 minutes.

One (1) μl each of exonuclease I and shrimp alkaline phosphatase in PCR Product Pre-Sequencing Kit (USB) were added to 5 μl of the nested PCR reaction solution and reacted at 37° C. for 15 minutes and at 85° C. for 15 minutes. The solution was reacted by using primer AP2 (SEQ ID NO: 5), primer rr4 (SEQ ID NO: 8) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 23 was obtained.

EXAMPLE 2

Cloning of the 3'-Downstream Terminus of cDNA Encoding Human TCH229 Protein

The 3'-downstream nucleotide sequence of cDNA encoding human TCH229 protein was revealed by 3'RACE PCR cloning.

Using two primer DNAs, i.e. primer AP1 (SEQ ID NO: 3) and primer ff1 (SEQ ID NO: 9), human kidney Marathon-Ready cDNA (Clontech) was subjected to primary PCR with Advantage 2 DNA Polymerase (Clontech) under the following conditions:

(1) reaction at 94° C. for 30 seconds, and
(2) 35 cycles each consisting of reaction at 94° C. for 10 seconds and at 63° C. for 3 minutes.

Using the primary PCR product as a template, nested PCR was conducted with primer AP2 (SEQ ID NO: 5), primer ff2 (SEQ ID NO: 10) and Advantage 2 DNA Polymerase (Clontech) under the following conditions:

(3) reaction at 94° C. for 30 seconds, and
(4) 30 cycles each consisting of reaction at 94° C. for 10 seconds and at 63° C. for 3 minutes.

One (1) µl each of exonuclease I and shrimp alkaline phosphatase in PCR Product Pre-Sequencing Kit (USB) were added to 5 µl of the nested PCR reaction solution and reacted at 37° C. for 15 minutes and at 85° C. for 15 minutes. The solution was reacted by using primer AP2 (SEQ ID NO: 5), primer ff2 (SEQ ID NO: 10) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 24 was obtained.

EXAMPLE 3

Cloning of cDNA Encoding Human TCH229 Protein

Using two primer DNAs, i.e. primer ORFF1 (SEQ ID NO: 11) and primer ORFR1 (SEQ ID NO: 12), human kidney Marathon-Ready cDNA (Clontech) was subjected to primary PCR with pfu turbo DNA Polymerase (Stratagene) under the following conditions (1) to (3):

(1) reaction at 94° C. for 30 seconds,
(2) 35 cycles each consisting of reaction at 94° C. for 10 seconds, at 57° C. for 10 seconds, and at 72° C. for 2.5 minutes, and
(3) reaction at 72° C. for 5 minutes.

Using the primary PCR product as a template, nested PCR was conducted with primer ORFF2 (SEQ ID NO: 13), primer ORFR2 (SEQ ID NO: 14) and pfu turbo DNA Polymerase (Stratagene) under the following conditions (4) to (6):

(4) reaction at 94° C. for 30 seconds,
(5) 30 cycles each consisting of reaction at 94° C. for 10 seconds, at 56° C. for 10 seconds and at 72° C. for 2.5 minutes, and
(6) reaction at 72° C. for 5 minutes.

The nested PCR reaction solution was purified by Min Elute Gel Extraction Kit (Qiagen). This DNA was cloned into pCR-Blunt II-TOPO vector according to a protocol of the Zero Blunt TOPO PCR Cloning Kit (Invitrogen, Inc.). The resulting product was transformed into *Escherichia coli* TOP 10 competent cell (Invitrogen, Inc.), and clones having the cDNA insert fragment were selected in a kanamycin-containing LB agar medium to give transformants. The respective clones were cultured overnight in a kanamycin-containing LB medium, and plasmid DNAs were prepared by QIAwell 8 Plasmid Kit (Qiagen) to give pCR-BluntII-TCH229 plasmid clones #1, #2 and #3. These were reacted with primer DNAs [primer M13F (SEQ ID NO: 15), primer M13R (SEQ ID NO: 16), primer ORFF2 (SEQ ID NO: 13), primer ORFR2 (SEQ ID NO: 14), primer rr2 (SEQ ID NO: 6), primer A1 (SEQ ID NO: 17), primer B2 (SEQ ID NO: 18), primer ff2 (SEQ ID NO: 10), primer rr1 (SEQ ID NO: 4), primer ff1 (SEQ ID NO: 9)] and BigDye Terminator Cycle Sequencing Kit (Applied Biosystems), and the nucleotide sequences of the inserted cDNA fragments were determined by a DNA sequencer ABI PRISM 3100 DNA analyzer (Applied Biosystems). As a result, the acquired 3 clones contained the same DNA fragment and had a 2251-nucleotide sequence (SEQ ID NO: 25). The fragment (SEQ ID NO. 2) encoded a 724-amino acid sequence (SEQ ID NO. 1), and the protein comprising the amino acid sequence represented by SEQ ID NO. 1 was designated human TCH229 protein.

The transformant bearing the plasmid containing the cDNA fragment was designated *Escherichia coli* TOP10/pCR-BluntII-TCH229.

Figure 1:
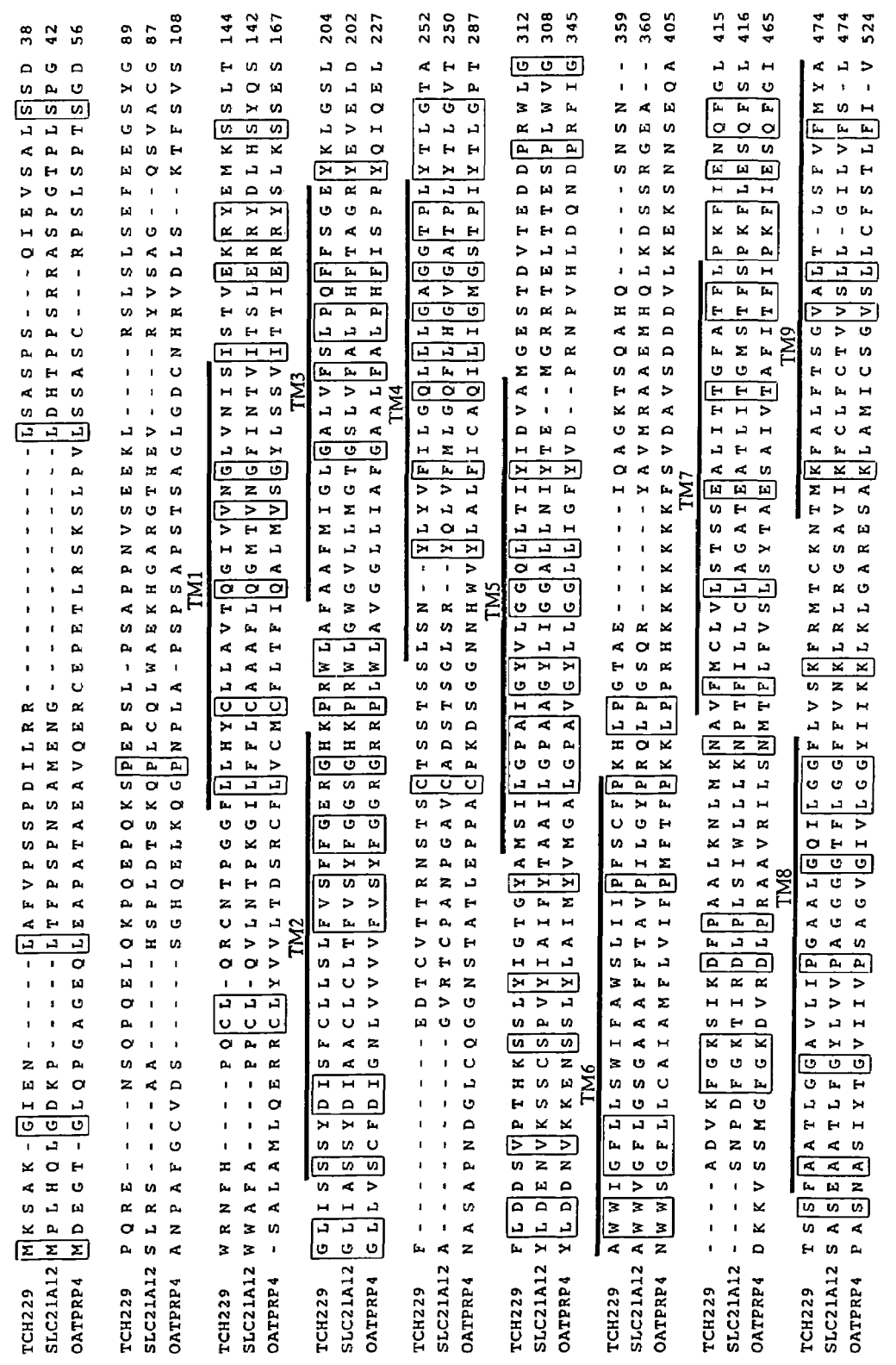
Figure 2:
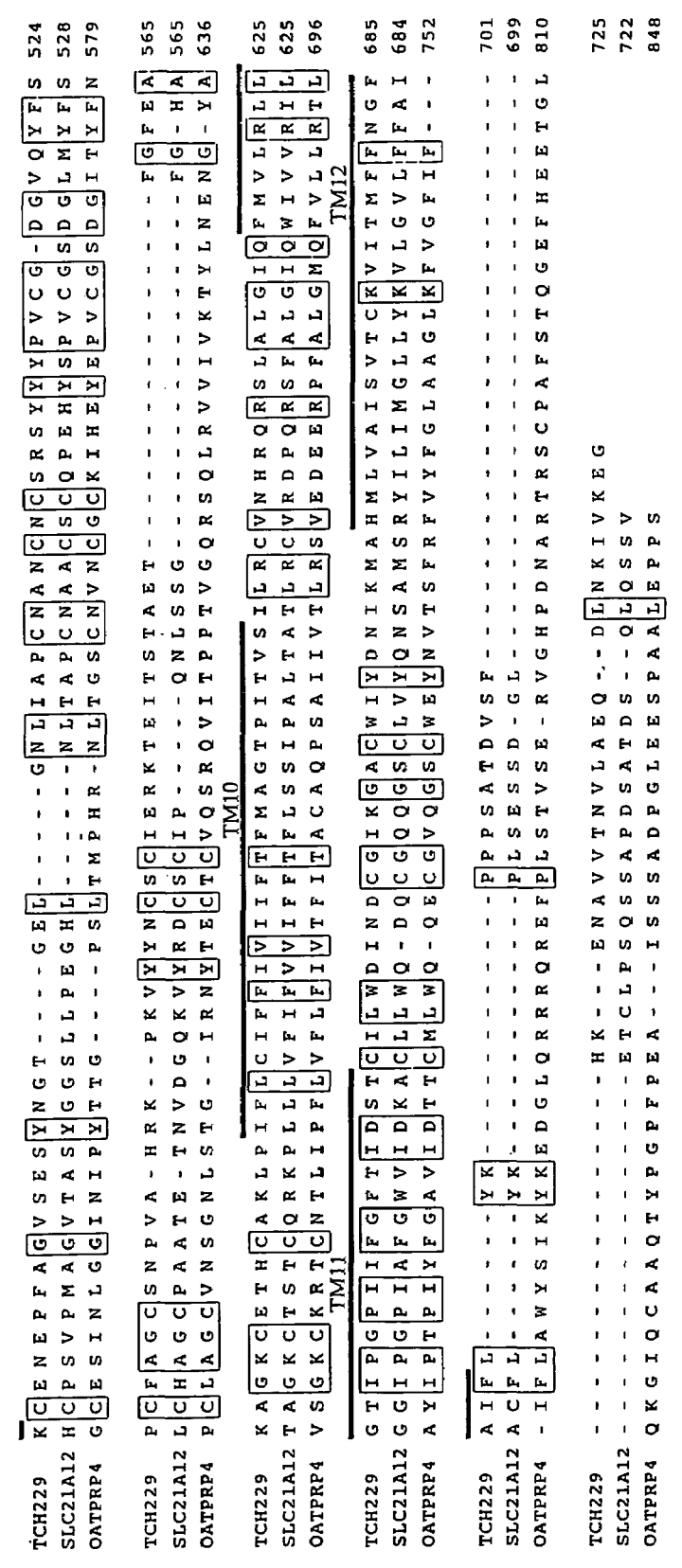

Using Blast P (Nucleic Acids Res., 25, 3389, 1997), homology search was conducted on a known data base, and the cDNA was revealed to be a novel gene belonging to organic anion transporter (FIGS. 1 and 2). In the figures, TM1 to TM12 show a transmembrane domain, respectively. The cDNA showed 41% homology on an amino acid level to SLC21A12 that is an organic anion transporter reported in humans (Biochemical and Biophysical Research Communications, 273, 251, 2000) and 36% homology on an amino acid level to OATPRP4 (GenBank Accession No. NM 030958), and the protein was estimated to have a 12-times transmembrane structure.

EXAMPLE 4

Analysis of Distribution of Human TCH229 Gene Product in Tissues

Using two primer DNAs, i.e. primer TMF (SEQ ID NO. 19) and primer TMR (SEQ ID NO. 20), designed from the sequence of human TCH229, and TaqMan probe P1 (SEQ ID NO. 21), the expression level of human TCH229 by cDNA in each human tissue was measured by TaqMan PCR.

Using TaqMan Universal PCR Master Mix (manufactured by Applied Biosystems, Inc.), the reaction was carried out by initially reacting at 50° C. for 2 minutes and at 95° C. for 10 minutes, followed by 40 cycles each consisting of a reaction at 95° C. for 15 seconds and at 60° C. for 1 minute, while detection was simultaneously made on the ABI PRISM 7900 sequence detection system (manufactured by Applied Biosystems, Inc.).

The cDNAs from the respective tissues in human, which were used for the assay, are shown in Table 1.

Figure 4:
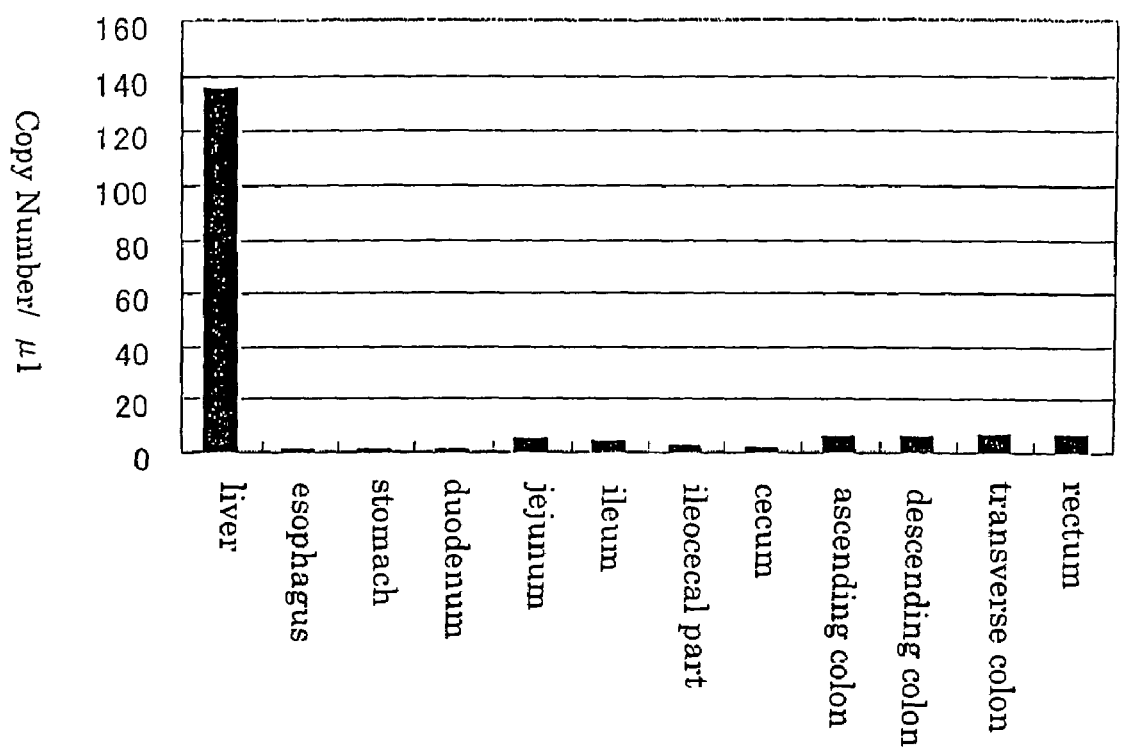
FIG. 4 shows the expression level of human TCH229 gene product in each tissue. The expression level is expressed in terms of the copy number per μl of cDNA solution.

The results are shown in FIGS. 3 and 4.

In the human MTC panel I and the MTC panel II, the human TCH299 gene product (mRNA) was expressed strongly in the kidney and slightly expressed in the lung, liver and pancreas.

In the human digestive system MTC panel, relatively strong expression was observed in the liver, but slight expression was observed in all of the sites from the stomach to the rectum.

TABLE 1

| CDNA (all manufactured by Clontech) | Tissue |
|---|---|
| Human MTC panel I | heart, brain, placenta, lung, liver, skeletal muscle, kidney, pancreas |
| Human MTC panel II | spleen, thymus, prostate, testis, ovary, small intestine, colon, peripheral leukocyte |
| Human digestive system MTC Panel | liver, esophagus, stomach, duodenum, jejunum, ileum, ileocecal part, cecum, ascending colon, transverse colon, descending colon, rectum |

EXAMPLE 5

Cloning of the 5'-Upstream Terminus of cDNA Encoding Mouse TCH229 Protein

The 5'-upstream nucleotide sequence of cDNA encoding mouse TCH229 protein was revealed by PCR cloning and 5'RACE PCR cloning.

Using two primer DNAs [primer h243F (SEQ ID NO: 28) and primer mR1 (SEQ ID NO: 29)], human kidney Marathon-Ready cDNA (Clontech) was subjected to PCR with Advantage 2 DNA Polymerase (Clontech) under the following conditions:

(1) reaction at 94° C. for 30 seconds, (2) 35 cycles each consisting of reaction at 94° C. for 10 seconds, at 63° C. for 10 seconds and at 68° C. for 2 minutes, and (3) reaction at 68° C. for 3 minutes.

One (1) µl each of exonuclease I and shrimp alkaline phosphatase in PCR Product Pre-Sequencing Kit (USB) were added to 5 µl of the PCR reaction solution and reacted at 37° C. for 15 minutes and at 85° C. for 15 minutes. The solution was reacted by using primer h243F (SEQ ID NO: 28), primer mR1 (SEQ ID NO: 29) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 48 was obtained.

On the basis of SEQ ID NO: 48, primer mrr5 (SEQ ID NO: 30) and primer mrr6 (SEQ ID NO: 31) were designed. Using two kinds of primer DNA [primer AP1 (SEQ ID NO: 3) and primer mrr6 (SEQ ID NO: 31)], mouse kidney Marathon-Ready cDNA (Clontech) was subjected to primary PCR with Advantage 2 DNA Polymerase (Clontech) under the following conditions:

(1) reaction at 94° C. for 30 seconds, and (2) 40 cycles each consisting of reaction at 94° C. for 10 seconds and at 64° C. for 4 minutes.

Using the primary PCR product as a template, nested PCR was conducted with primer AP2 (SEQ ID NO: 5), primer mrr5 (SEQ ID NO: 30) and Advantage 2 DNA Polymerase (Clontech) under the following conditions:

(3) reaction at 94° C. for 30 seconds, and (4) 35 cycles each consisting of reaction at 94° C. for 10 seconds and at 64° C. for 3 minutes.

One (1) µl each of exonuclease I and shrimp alkaline phosphatase in PCR Product Pre-Sequencing Kit (USB) were added to 5 µl of the nested PCR reaction solution and reacted at 37° C. for 15 minutes and at 85° C. for 15 minutes. The solution was reacted by using primer mrr5 (SEQ ID NO: 30) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 49 was obtained.

EXAMPLE 6

Cloning of the 3'-Downstream Terminus of cDNA Encoding Mouse TCH229 Protein

The 3'-upstream nucleotide sequence of cDNA encoding mouse TCH229 protein was revealed by 3'RACE PCR cloning.

Using two primer DNAs [primer AP1 (SEQ ID NO: 3) and primer mF1 (SEQ ID NO: 32)], mouse kidney Marathon-Ready cDNA (Clontech) was subjected to primary PCR with Advantage 2 DNA Polymerase (Clontech) under the following conditions:

(1) reaction at 94° C. for 30 seconds, and (2) 40 cycles each consisting of reaction at 94° C. for 10 seconds and at 61° C. for 4 minutes.

Using the primary PCR product as a template, nested PCR was conducted with primer AP2 (SEQ ID NO: 5), primer mff2 (SEQ ID NO: 33) and Advantage 2 DNA Polymerase (Clontech) under the following conditions:

(3) reaction at 94° C. for 30 seconds, and (4) 35 cycles each consisting of reaction at 94° C. for 10 seconds and at 61° C. for 3 minutes.

One (1) µl each of exonuclease I and shrimp alkaline phosphatase in PCR Product Pre-Sequencing Kit (USB) were added to 5 µl of the nested PCR reaction solution and reacted at 37° C. for 15 minutes and at 85° C. for 15 minutes. The solution was reacted by using primer mff2 (SEQ ID NO: 33) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 50 was obtained.

EXAMPLE 7

Cloning of cDNA Encoding Mouse TCH229 Protein

Using two primer DNAs [primer mORFF(4) (SEQ ID NO: 34) and primer mORFR(2195) (SEQ ID NO: 35)], mouse kidney Marathon-Ready cDNA (Clontech) was subjected to primary PCR with pfu turbo DNA Polymerase (Stratagene) under the following conditions (1) to (3):

(1) reaction at 94° C. for 30 seconds, (2) 35 cycles each consisting of reaction at 94° C. for 10 seconds, at 56° C. for 10 seconds and at 72° C. for 2 minutes, and (3) reaction at 72° C. for 5 minutes.

Using the primary PCR product as a template, nested PCR was conducted with primer mORFF(atg) (SEQ ID NO: 36), primer mORFR(tga) (SEQ ID NO: 37) and pfu turbo DNA Polymerase (Stratagene) under the following conditions (4) to (6):

(4) reaction at 94° C. for 30 seconds,
(5) 30 cycles each consisting of reaction at 94° C. for 10 seconds, at 56° C. for 10 seconds and at 72° C. for 2 minutes, and
(6) reaction at 72° C. for 5 minutes.

1.5 µl of Advantage 2 DNA Polymerase (Clontech) was added to 10 µl of the nested PCR reaction solution, then reacted at 72° C. for 10 minutes, and purified by Min Elute Gel Extraction Kit (Qiagen). This DNA was cloned into pCR2.1-TOPO vector according to a protocol of the TOPO TA Cloning Kit (Invitrogen, Inc.). The resulting product was transformed into Escherichia coli TOP10 competent cell (Invitrogen, Inc.), and clones having the cDNA insert fragment were selected in a kanamycin-containing LB agar medium to give transformants. The respective clones were cultured overnight in a kanamycin-containing LB medium, and plasmid DNAs were prepared by QIAwell 8 Plasmid Kit (Qiagen) to give pCR2.1-mTCH229 plasmid clones #1, #2 and #3. These were reacted with primer DNAs [primer M13F (SEQ ID NO: 15), primer M13R (SEQ ID NO: 16), primer h243F (SEQ ID NO: 28), primer mR1 (SEQ ID NO: 29), primer h650F (SEQ ID NO: 38), primer h910F (SEQ ID NO: 39), primer mrr1 (SEQ ID NO: 40), primer mrr2 (SEQ ID NO: 41), primer mrr3 (SEQ ID NO: 42), primer F(45) (SEQ ID NO: 43), primer m521R (SEQ ID NO: 44), primer mF1 (SEQ ID NO: 32), primer mff2 (SEQ ID NO: 33), primer mrr6 (SEQ ID NO: 31)] and BigDye Terminator Cycle Sequencing Kit (Applied Biosystems), and the nucleotide sequences of the inserted cDNA fragments were determined by a DNA sequencer ABI PRISM 3100 DNA analyzer (Applied Biosystems). As a result, the acquired 3 clones contained the same DNA fragment and had a 2169-nucleotide sequence (SEQ ID NO: 51). The fragment (SEQ ID NO. 27) encoded a 722-amino acid sequence (SEQ ID NO. 26), and the protein comprising the amino acid sequence represented by SEQ ID NO. 26 was designated mouse TCH229 protein.

The transformant bearing the plasmid containing the cDNA fragment was named Escherichia coli TOP 10/pCR2.1-mTCH229.

Using Blast P (Nucleic Acids Res., 25, 3389, 1997), homology search was conducted on a known data base, and the cDNA showed 43.2% homology on a base level and 37% homology on an amino acid level to mouse SLC21A11 (Genbank: NP_076397) which is an organic anion transporter reported in mouse. Mouse TCH229 showed 83% homology on a base level and 81% homology on an amino acid level to a novel gene belonging to the organic anion transporter family, and was revealed to be a mouse homologue to human TCH229 (FIG. 5). In the figure, TM1 to TM12 show a transmembrane domain, respectively, and * is given to highly stored amino acids in the family.

EXAMPLE 8

Analysis of Distribution of Mouse TCH229 Gene Product in Tissues

Using two primer DNAs, i.e. primer mTMF (SEQ ID NO: 45) and primer mTMR (SEQ ID NO: 46), designed from the sequence of mouse TCH229, and TaqMan probe mP1 (SEQ ID NO. 47), the expression level of mouse TCH229 by cDNA in each mouse tissue was measured by TaqMan PCR.

Using TaqMan Universal PCR Master Mix (manufactured by Applied Biosystems, Inc.), the reaction was carried out by initially reacting at 50° C. for 2 minutes and at 95° C. for 10 minutes, followed by 40 cycles each consisting of a reaction at 95° C. for 15 seconds and at 60° C. for 1 minute, while detection was simultaneously made on the ABI PRISM 7900 sequence detection system (manufactured by Applied Biosystems, Inc.).

Figure 6:
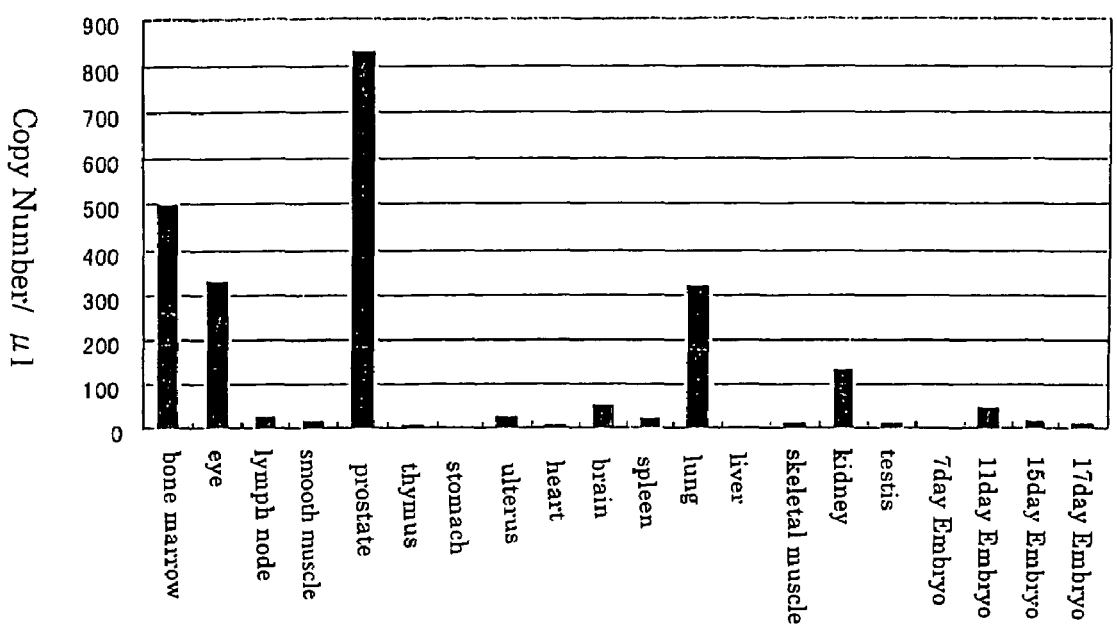
FIG. 6 shows the expression level of mouse TCH229 gene product in each tissue. The expression level is expressed in terms of the copy number per μl of cDNA solution.

The results are shown in FIG. 6.

In the mouse MTC panel I and MTC panel II, the mouse TCH229 gene product (mRNA) was expressed strongly in the prostate and expressed relatively strongly in the bone marrow, eye, lung and kidney.

EXAMPLE 9

Cloning of the 5'-Upstream of cDNA Encoding Rat TCH229 Protein

The 5'-upstream nucleotide sequence of cDNA encoding rat TCH229 protein was revealed by PCR cloning and 5'RACE PCR cloning.

Using two primer DNAs [primer m163F (SEQ ID NO: 56) and primer m2087R (SEQ ID NO: 57) designed on the basis of the sequence of mouse TCH229 (SEQ ID NO: 51)], rat kidney Marathon-Ready cDNA (Clontech) was subjected to PCR with Advantage 2 DNA Polymerase (Clontech) under the following conditions:
(1) reaction at 94° C. for 30 seconds,
(2) 35 cycles each consisting of reaction at 94° C. for 10 seconds, at 60° C. for 10 seconds and at 68° C. for 2.5 minutes, and
(3) reaction at 68° C. for 5 minutes.

One (1) µl each of exonuclease I and shrimp alkaline phosphatase in PCR Product Pre-Sequencing Kit (USB) were added to 5 µl of the PCR reaction solution and reacted at 37° C. for 15 minutes and at 85° C. for 15 minutes. The solution was reacted by using primer m163F (SEQ ID NO: 56), primer m2087R (SEQ ID NO: 57) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 77 was obtained.

On the basis of SEQ ID NO: 77, primer r229-rr1 (SEQ ID NO: 58) and primer r229-rr2 (SEQ ID NO: 59) were designed. Using two kinds of primer DNA [primer AP1 (SEQ ID NO: 3) and primer r229-rr1 (SEQ ID NO: 58)], rat kidney Marathon-Ready cDNA (Clontech) was subjected to primary PCR with Advantage 2 DNA Polymerase (Clontech) under the following conditions:
(1) reaction at 94° C. for 30 seconds, and
(2) 35 cycles each consisting of reaction at 94° C. for 10 seconds and at 64° C. for 2 minutes.

Using the primary PCR product as a template, nested PCR was conducted with primer AP2 (SEQ ID NO: 5), primer r229-rr2 (SEQ ID NO: 59) and Advantage 2 DNA Polymerase (Clontech) under the following conditions:
(3) reaction at 94° C. for 30 seconds, and
(4) 35 cycles each consisting of reaction at 94° C. for 10 seconds and at 64° C. for 2 minutes.

One (1) µl each of exonuclease I and shrimp alkaline phosphatase in PCR Product Pre-Sequencing Kit (USB) were added to 5 µl of the nested PCR reaction solution and reacted at 37° C. for 15 minutes and at 85° C. for 15 minutes. The solution was reacted by using primer r229-rr2 (SEQ ID NO: 59) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 78 was obtained.

EXAMPLE 10

Cloning of the 3'-Downstream Terminus of cDNA Encoding Rat TCH229 Protein

The 3'-downstream terminus of cDNA encoding rat TCH229 protein was revealed by 3'RACE PCR cloning.

Using two primer DNAs [primer AP1 (SEQ ID NO: 3) and primer rff1 (SEQ ID NO: 60)], rat kidney Marathon-Ready cDNA (Clontech) was subjected to primary PCR with Advantage 2 DNA Polymerase (Clontech) under the following conditions:

(1) reaction at 94° C. for 30 seconds, and
(2) 35 cycles each consisting of reaction at 94° C. for 10 seconds and at 64° C. for 2 minutes.

Using the primary PCR product as a template, nested PCR was conducted with primer AP2 (SEQ ID NO: 5), primer rff3 (SEQ ID NO: 61) and Advantage 2 DNA Polymerase (Clontech) under the following conditions:

(3) reaction at 94° C. for 30 seconds, and
(4) 30 cycles each consisting of reaction at 94° C. for 10 seconds and at 64° C. for 2 minutes.

One (1) µl each of exonuclease I and shrimp alkaline phosphatase in PCR Product Pre-Sequencing Kit (USB) were added to 5 µl of the nested PCR reaction solution and reacted at 37° C. for 15 minutes and at 85° C. for 15 minutes. The solution was reacted by using primer rff3 (SEQ ID NO: 61) and BigDye Terminator Cycle Sequencing Kit (Applied Biosystems), and the nucleotide sequence of the amplified DNA fragment was determined by DNA sequencer ABI PRISM 3100 DNA analyzer (Applied Biosystems). As a result, the nucleotide sequence represented by SEQ ID NO: 79 was obtained.

EXAMPLE 11

Cloning of cDNA Encoding Rat TCH229 Protein

Using two primer DNAs i.e. primer rORFF1 (SEQ ID NO: 62) and primer rORFR12 (SEQ ID NO: 63), rat kidney Marathon-Ready cDNA (Clontech) was subjected to primary PCR with pfu turbo DNA Polymerase (Stratagene) under the following conditions (1) to (3):

(1) reaction at 94° C. for 30 seconds,
(2) 35 cycles each consisting of reaction at 94° C. for 10 seconds, at 56° C. for 10 seconds and at 72° C. for 2.5 minutes, and
(3) reaction at 72° C. for 5 minutes.

Using the primary PCR product as a template, nested PCR was conducted with primer rORFF(atg) (SEQ ID NO: 64), primer rORFR(tga2) (SEQ ID NO: 65) and pfu turbo DNA Polymerase (Stratagene) under the following conditions (4) to (6):

(4) reaction at 94° C. for 30 seconds,
(5) 30 cycles each consisting of reaction at 94° C. for 10 seconds, at 56° C. for 10 seconds and at 72° C. for 2.5 minutes, and
(6) reaction at 72° C. for 5 minutes. 1.5 µl of Advantage 2 DNA Polymerase (Clontech) was added to 10 µl of the nested PCR reaction solution, then reacted at 72° C. for 10 minutes, and purified by Min Elute Gel Extraction Kit (Qiagen). This DNA was cloned into pCRII-TOPO vector according to a protocol of the TOPO TA Cloning Kit (Invitrogen, Inc.). The resulting product was transformed into Escherichia coli TOP10 competent cell (Invitrogen, Inc.), and clones having the cDNA insert fragment were selected in a kanamycin-containing LB agar medium to give transformants. The respective clones were cultured overnight in a kanamycin-containing LB medium, and plasmid DNAs were prepared by QIAwell 8 Plasmid Kit (Qiagen) to give pCRII-rTCH229 plasmid clones #1, #2, #3 and #4. These were reacted with primer DNAs [primer T7 (SEQ ID NO: 66), primer SP6 (SEQ ID NO: 67), primer rORFF(atg) (SEQ ID NO: 64), primer rORFR(tga2) (SEQ ID NO: 65), primer rF1 (SEQ ID NO: 68), primer rTMR (SEQ ID NO: 69), primer rTMF (SEQ ID NO: 70), primer rff3 (SEQ ID NO: 61), primer rff2 (SEQ ID NO: 71), primer rR1 (SEQ ID NO: 72), primer r972F (SEQ ID NO: 73), primer r1123F (SEQ ID NO: 74), primer r1746R (SEQ ID NO: 75)] and BigDye Terminator Cycle Sequencing Kit (Applied Biosystems), and the nucleotide sequences of the inserted cDNA fragments were determined by a DNA sequencer ABI PRISM 3100 DNA analyzer (Applied Biosystems). As a result, the acquired 4 clones contained 2 kinds of DNA fragments (Nos. 1 and 2). No. 1 had a 2175-nucleotide sequence (SEQ ID NO: 80), and the fragment (SEQ ID NO. 53) encoded a 724-amino acid sequence (SEQ ID NO. 52), and contained an amino acid sequence represented by SEQ ID NO: 52. No. 2 had a 2175-nucleotide sequence (SEQ ID NO: 81), and the fragment (SEQ ID NO. 55) encoded a 724-amino acid sequence (SEQ ID NO. 54), and contained an amino acid sequence represented by SEQ ID NO: 55. The respective proteins were designated rat TCH229 protein No. 1 and rat TCH229 protein No. 2, respectively.

Transformants bearing the plasmids containing the cDNA fragments were designated Escherichia coli TOP10/pCRII-rTCH229 No. 1 and Escherichia coli TOP10/pCRII-rTCH229 No. 2, respectively.

In the rat TCH229 protein No. 1 and rat TCH229 protein No. 2, base substitution was recognized in 4 sites (positions 144, 231, 1252 and 1539 in the nucleotide sequence represented by SEQ ID NO. 53). Among the 4 sites, 3 sites i.e. A144T (Glu→Asp), C231A (Ser→Arg) and A1252T (Ile→Phe) were accompanied by amino acid substitution as shown in the parentheses, but A1539G was not accompanied by amino acid substitution. There is a possibility that these base substitutions are derived from single nucleotide polymorphisms (SNPs).

Using Blast P (Nucleic Acids Res., 25, 3389, 1997), homology search was conducted on a known data base, and the rat TCH229 Nos. 1 and 2 showed about 50% homology on a base level and about 41% homology on an amino acid level to rat oatp-E that is an organic anion transporter reported in rat (Endocrinology, 142(5), 2005, 2001). The rat TCH229 Nos. 1 and 2 showed about 81.4% homology on a base level and about 81.6% homology on an amino acid level to a novel gene belonging to the organic anion transporter family, and were revealed to be mouse horologes to human TCH229 (FIGS. 7 and 8). In the figures, TM1 to TM12 show a transmembrane domain, respectively.

EXAMPLE 12

Analysis of Distribution of Rat TCH229 Gene Product in Tissues

Using two primer DNAs, i.e., primer rTMF (SEQ ID NO: 70) and primer rTMR (SEQ ID NO: 69), which were designed based on the sequence of rat TCH229, and TaqMan probe rP1 (SEQ ID NO: 76), the expression level of rat TCH229 in cDNAs from the respective tissues (spleen, thymus, testis, small intestine, stomach, skin, heart, brain, lung, muscle, kidney) in rat was assayed by TaqMan PCR.

Figure 9:
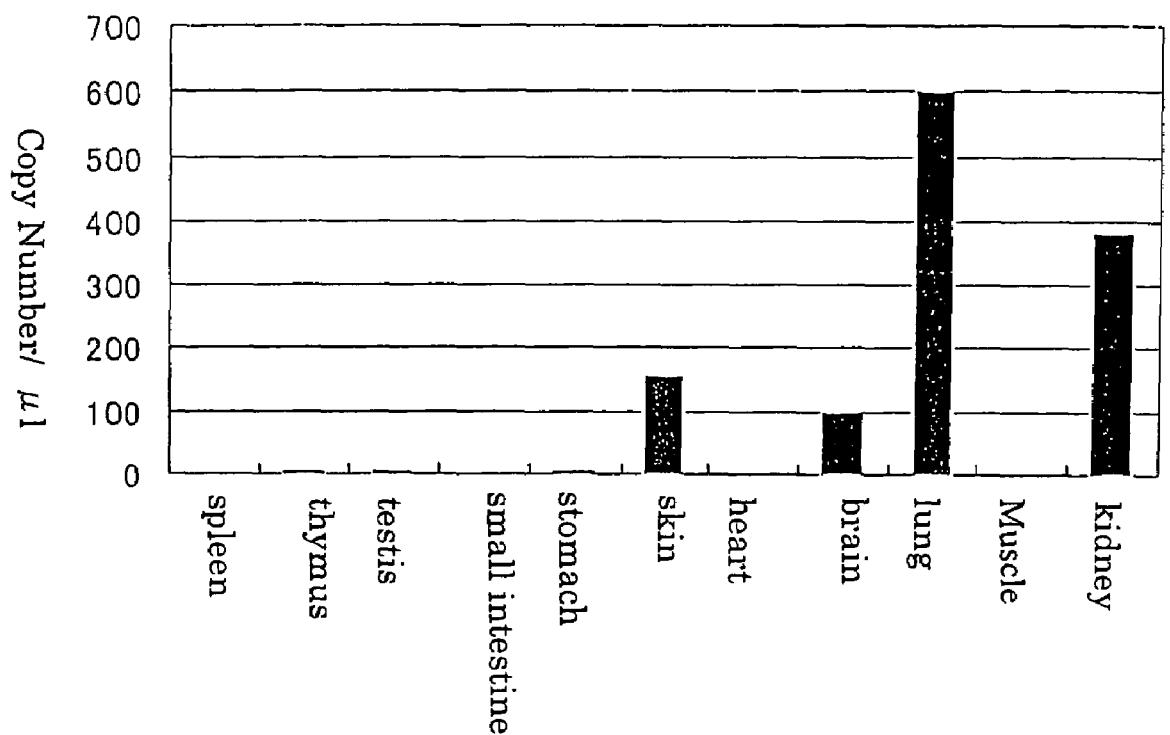
FIG. 9 shows the expression level of rat TCH229 gene product in each tissue. The expression level is expressed in terms of the copy number per μl of cDNA solution.

Using TaqMan Universal PCR Master Mix (manufactured by Applied Biosystems, Inc.), the reaction was carried out by initially reacting at 50° C. for 2 minutes and then at 95° C. for 10 minutes, followed by 40 cycles each consisting of a reaction at 95° C. for 15 seconds and at 60° C. for 1 minute, while detection was simultaneously made on the ABI PRISM 7900 sequence detection system (manufactured by Applied Biosystems, Inc.). The results are shown in FIG. 9.

In Multiple Choice cDNAs (Rat Kit I and Rat Kit II (manufactured by OriGene)), the rat TCH229 gene product (mRNA) was strongly expressed in the lung and kidney and also expressed in the skin and brain.

EXAMPLE 13

Analysis of Distribution of Mouse TCH229 Gene Product in Issues of 7-Week-Old BALB/c Mouse (1) Preparation of cDNAs from the Respective Tissues in Normal Mice The total RNA was prepared from the respective tissues in BALB/c mice of 7 weeks old [cerebrum, cerebellum, hippocampus, medulla oblongata, bone marrow, sciatic nerve, skin, skeletal muscle, eyeball, heart, lung, trachea, pancreas, kidney, liver, anterior stomach, posterior stomach, duodenum, jejunoileum, cecum, colon, rectum, spleen, thymus, bone marrow, ovary, uterus, prostate, testis (the ovary and uterus were collected from the female animal and the other tissues were from the male animal, respectively, each tissue in 1 to 10 mice)], using ISOGEN (manufactured by Nippon Gene) or RNeasy Mini Kit (manufactured by Qiagen). Using TaqMan Reverse Transcription Reagents (manufactured by Applied Biosystems, Inc.), reverse transcription was performed to prepare cDNA.

(2) Analysis of Distribution of Mouse TCH299 Gene Product in Tissues

Using the two primer DNAs in Example 8 (that is, primer mTMF (SEQ ID NO: 45) and primer mTMR (SEQ ID NO: 46)) and TaqMan probe mP1 (SEQ ID NO: 47), the expression level (copy number) of mouse TCH229 in cDNAs from the respective mouse tissues described above was assayed by TaqMan PCR. The expression level (copy number) of rodent glyceraldehyde-3-phosphate dehydrogenase (GAPDH) was also assayed for the same cDNAs, using TaqMan rodent GAPDH control reagents (manufactured by Applied Biosystems, Inc.). Using TaqMan Universal PCR Master Mix (manufactured by Applied Biosystems, Inc.), the reaction was carried out by initially reacting at 50° C. for 2 minutes and then at 95° C. for 10 minutes, followed by 40 cycles each consisting of a reaction at 95° C. for 15 seconds and at 60° C. for 1 minute, while detection was simultaneously made on the ABI PRISM 7900 sequence detection system (manufactured by Applied Biosystems, Inc.).

Figure 10:
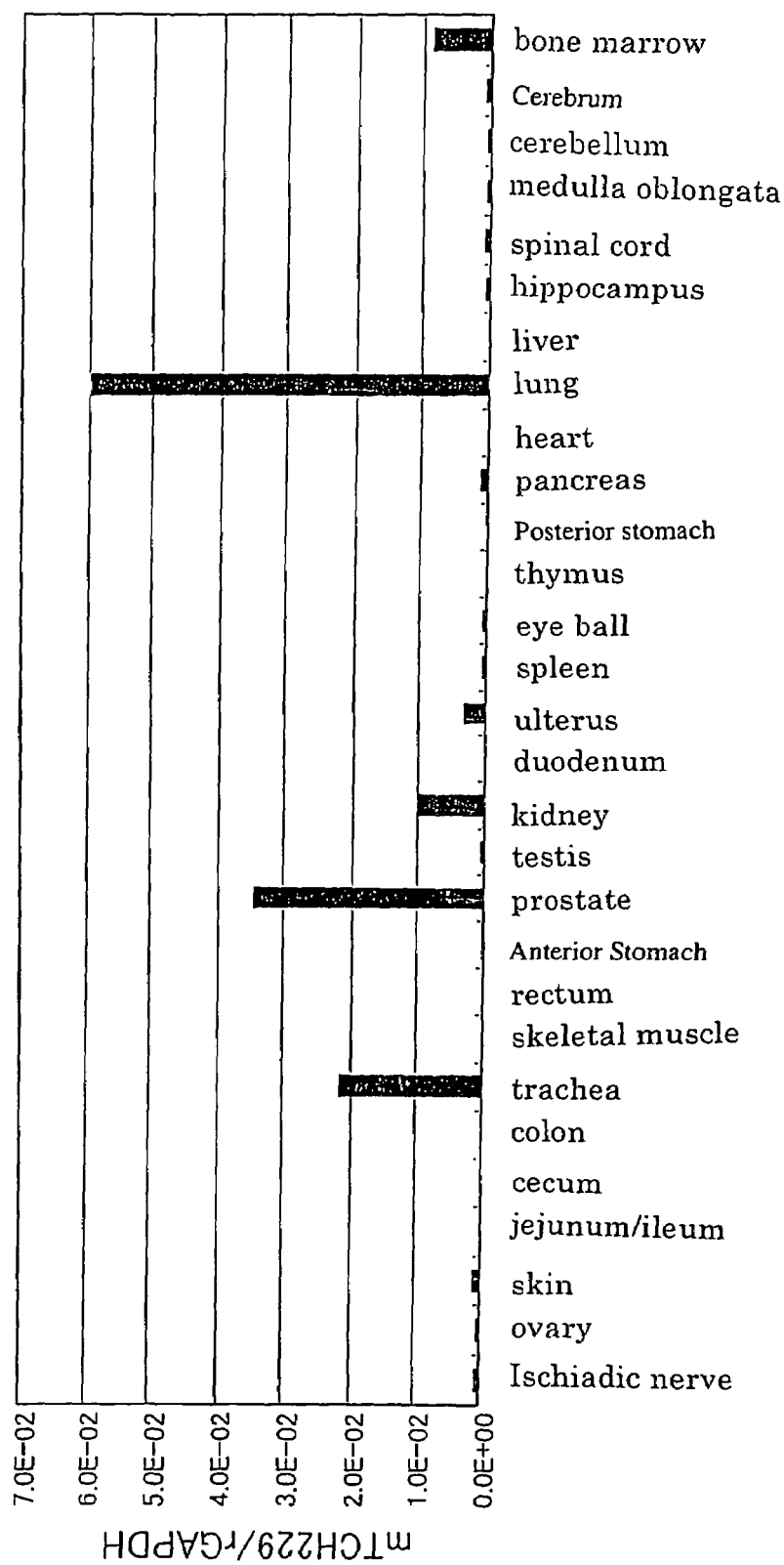
FIG. 10 shows the expression level of mouse TCH229 gene product in each tissue. The expression level is expressed in terms of the value obtained by dividing the copy number of mouse TCH229 per μl of cDNA solution by the copy number of rodent GAPDH in an equal amount of cDNA in each tissue.

The results are shown in FIG. 10.

In the respective tissues of BALB/c mice of 7 weeks old, the mouse TCH229 gene product (mRNA) was somewhat expressed in the prostate, trachea, kidney and bone marrow and highly expressed in the lung.

EXAMPLE 14

(1) Preparation of cDNAs from the Respective Tissues in Normal Rats

The total RNA was prepared from the respective tissues (cerebrum, cerebellum, liver, kidney, prostate, heart, lung, duodenum, jejunoileum, colon, skin, eyeball) in Wistar male rats of 12 weeks old, using RNeasy Mini Kit (manufactured by Qiagen). The total RNA thus prepared was subjected to reverse transcription using TaqMan Reverse Transcription Reagents (manufactured by Applied Biosystems, Inc.) to prepare cDNA.

(2) Analysis of Distribution of the Rat TCH299 Gene Product in Tissues

Using the two primer DNAs in Example 12 (that is, primer rTMF (SEQ ID NO: 70) and primer rTMR (SEQ ID NO: 69)) and TaqMan probe rP1 (SEQ ID NO: 76), the expression level (copy number) of rat TCH229 in cDNAs from the respective rat tissues described above was assayed by TaqMan PCR. The expression level (copy number) of rodent glyceraldehyde-3-phosphate dehydrogenase (GAPDH) was also assayed for the same cDNAs, using TaqMan rodent GAPDH control reagents (manufactured by Applied Biosystems, Inc.). Using TaqMan Universal PCR Master Mix (manufactured by Applied Biosystems, Inc.), the reaction was carried out by initially reacting at 50° C. for 2 minutes and then at 95° C. for 10 minutes, followed by 40 cycles each consisting of a reaction at 95° C. for 15 seconds and at 60° C. for 1 minute, while detection was simultaneously made on the ABI PRISM 7900 sequence detection system (manufactured by Applied Biosystems, Inc.).

Figure 11:
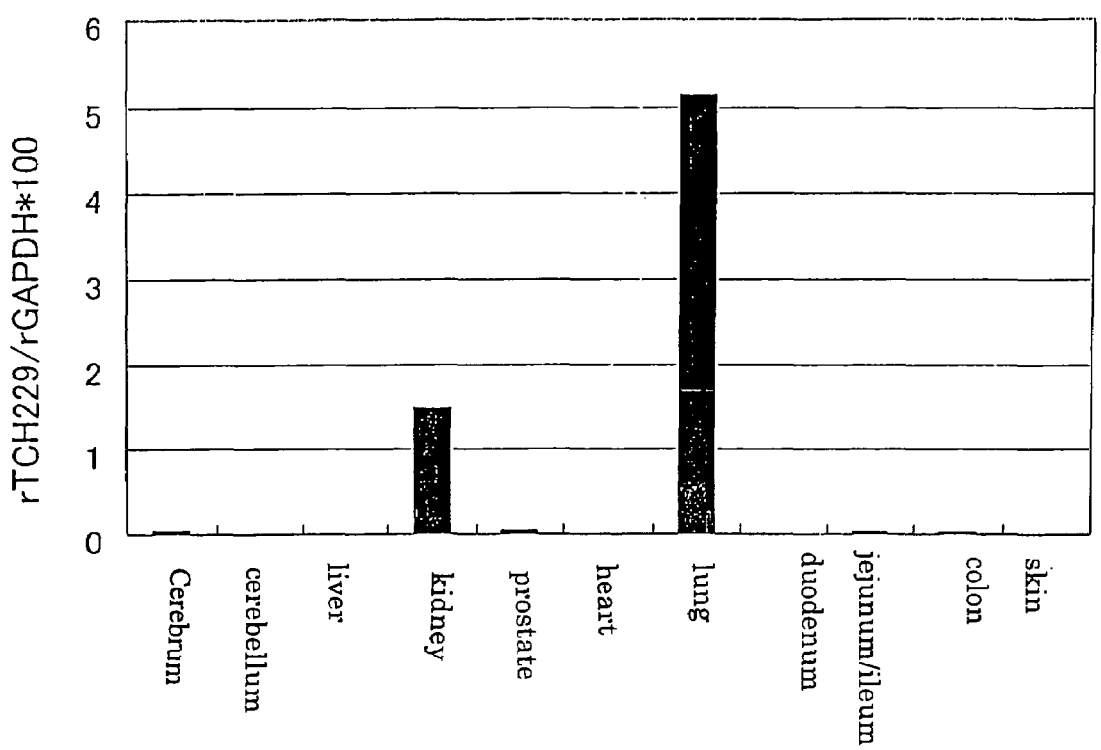
FIG. 11 shows the expression level of rat TCH229 gene product in each tissue. The expression level is expressed as (relative expression level×100).

The results are shown in FIG. 11.

In the respective tissues of Wistar rats of 12 weeks old, the rat TCH299 gene product (mRNA) was strongly expressed in the kidney and lung.

EXAMPLE 15

Construction of Human TCH229 Expression Vector

Human TCH229 (SEQ ID NO. 1) expression vector was constructed by the following method.

Using 10 ng of the plasmid obtained in Example 1 as a template, PCR was conducted with primer 2290F2 (SEQ ID NO. 82) and primer 2290R2 (SEQ ID NO. 83) and pfu turbo DNA Polymerase (Stratagene) under the following conditions (1) to (3). The 5'-terminal side primer 2290F2 and the 3'-terminal side primer 2290R2 were designed such that Eco RV site and Xho I site were added respectively to the 5'-terminal side for cloning into a vector.

(1) reaction at 94° C. for 30 seconds, (2) 35 cycles each consisting of reaction at 94° C. for 10 seconds, at 55° C. for 10 seconds and at 70° C. for 2.5 minutes, and (3) reaction at 70° C. for 5 minutes.

The PCR reaction solution was subjected to gel electrophoresis, and a major band was purified. The PCR fragment thus obtained was digested with restriction enzymes Eco RV and Xho I at 37° C. for 1 hour, and the reaction solution was subjected to gel electrophoresis and purified. The product was ligated to Eco RV site and Xho I site of an animal cell expression vector pcDNA3.1(+) (Invitrogen, Inc.) by Takara ligation kit ver. 2 (Takara Bio). This ligation reaction solution was precipitated with ethanol and used to transform a competent cell *Escherichia coli* TOP10 (Invitrogen, Inc.). From a plurality of colonies thus obtained, a plasmid was prepared, and this nucleotide sequence was reacted by using primer DNAs [primer BGH RV (SEQ ID NO. 84), primer T7 (SEQ ID NO: 66), primer 2290F2 (SEQ ID NO: 82), primer 2290R2 (SEQ ID NO. 83), primer rr2 (SEQ ID NO. 6), primer A1 (SEQ ID NO. 17), primer B2 (SEQ ID NO. 18), primer ff2 (SEQ ID NO. 10), primer rr1 (SEQ ID NO. 4), primer ff1 (SEQ ID NO. 9)] and BigDye Terminator Cycle Sequencing Kit (Applied Biosystems), and the nucleotide sequence was confirmed by DNA sequencer ABI PRISM 3100 DNA analyzer (Applied Biosystems). The transformant having this plasmid was designated *Escherichia coli* TOP 10/pCDNA3.1(+)-TCH229.

EXAMPLE 16

Preparation of Human TCH229-Expressing CHO Cell Strain and Measurement of the Expression Level of the Introduced Gene

*Escherichia coli* TOP10/pCDNA3.1(+)-TCH229 was cultured, and from this *Escherichia coli*, plasmid DNA was prepared by EndoFree Plasmid Maxi Kit (Qiagen). This plasmid DNA was introduced into CHO dhfr– cells by using FuGENE 6 Transfection Reagent (Roche) according to its attached protocol. A mixture of 2 µg plasmid DNA and transfection reagents was added to a 6 cm Petri dish on which $2 \times 10^5$ CHO dhfr– cells had been plated before 24 hours. The cells were cultured for 1 day in MEMα medium (Invitrogen, Inc.) containing 10% bovine fetal serum (JRH Bioscience), then 1.0 mg/ml geneticine (Invitrogen, Inc.) was added to the medium, and then the TCH229 expression cells were cultured. During culture, the medium was exchanged several times, and after about 10 days, the cells were peeled off by treatment with trypsin, and the recovered cells were plated on a 96-well plate at a density of 0.5-1 cell/well, and about 10 days thereafter, the TCH229 expression cells were selected in a medium containing 1.0 mg/ml geneticine. From the grown cells in wells wherein one colony had grown per well, total RNA was prepared by RNeasy Mini Kit or RNeasy 96 Kit (both available from Qiagen). The prepared total RNA was subjected to reverse transcription reaction by TaqMan Reverse Transcription Reagents (Applied Biosystems) to prepare cDNA. For the cDNA, the expression level of human TCH229 was measured by TaqMan PCR with the 2 primer DNAs used in Example 4 (that is, primer TMF (SEQ ID NO. 19) and primer TMR (SEQ ID NO. 20)) and TaqMan probe P1 (SEQ ID NO. 21). Using TaqMan Universal PCR Master Mix (manufactured by Applied Biosystems, Inc.), the reaction was carried out by initially reacting at 50° C. for 2 minutes and then at 95° C. for 10 minutes, followed by 40 cycles each consisting of a reaction at 95° C. for 15 seconds and at 60° C. for 1 minute, while detection was simultaneously made on the ABI PRISM 7900 sequence detection system (manufactured by Applied Biosystems, Inc.). As a (monoclonal) cell strain highly expressing human TCH229 gene, Clone No. 71 was selected.

EXAMPLE 17

Analysis of Expression of Human TCH299 Gene in Commercial Normal Human Cells (1) Preparation of Normal Human Cell cDNA Normal human cells were purchased from Cambrex BioScience Walkersvill and cultured in accordance with the instructions attached to the product. The cells used in the experiment are shown in Table 2.

TABLE 2

| Cell name (*is stimulated with TNF-α, IL-1β, IL-6) |
|---|
| 1. Umbilical cord vein endothelial cell |
| 2. Main artery endothelial cell |
| 3. Coronary artery endothelial cell |
| 4. Main artery smooth muscle cell |
| 5. Coronary artery smooth muscle cell |
| 6. Uterus smooth muscle cell |
| 7. Bronchial smooth muscle cell |
| 8. Skeletal muscle satellite cell |
| 9. Mammary gland epithelial cell |
| 10. Bronchial epithelial cell (with RA) |
| 11. Bronchial epithelial cell (without RA) |
| 12. Lung fibroblast |
| 13. Renal proximal urine tubule epithelial cell |
| 14. Mesangial cell |
| 15. Renal cortical epithelial cell |
| 16. Mesenchyme stem cell |
| 17. Knee joint cartilage cell |
| 18. Osteoblast |
| 19. Dermal microvascular endothelial cell* |
| 20. Pulmonary microvascular endothelial cell* |
| 21. Artery pulmonary microvascular endothelial cell* |
| 22. Bronchus epithelial cell* |
| 23. Renal epithelial cell* |
| 24. Prostate interstitial cell* |
| 25. Epidermal keratinocyte* |

Each of the cells was incubated in a 75 cm² culture flask to reach a sub-confluent state. TNF-α, IL-1β and IL-6 were added at a final concentration of 10 ng/ml respectively to the cells given symbol * in the table. The cells not given the symbol * were recovered by trypsin-EDTA treatment 16 hours after the culture was initiated, and the cells given the symbol * were recovered by trypsin-EDTA treatment 8 hours after a mixture of TNF-α, IL-1β and IL-6 was added. From the recovered cells, the total RNA was prepared using ISOGEN (manufactured by Nippon Gene Co., Ltd.) or RNeasy Mini Kit (manufactured by Qiagen) (in either case, contaminant DNA was removed by DNase treatment). The total RNA thus prepared was subjected to reverse transcription reaction using TaqMan Reverse Transcription Reagents (manufactured by Applied Biosystems, Inc.) to prepare the cDNA.

(2) Preparation of cDNA from Normal Human Cells Stimulated with Various Stimulants a) Renal proximal tubular epithelial cell (RPTEC) and human renal cortical epithelial cell (HRCE) (both available from Cambrex BioScience Walkersvill) were plated on a 24-well collagen-coated plate in $1 \times 10^5$ cells/well and then cultured overnight, and after the medium was replaced by triiodotyrosine (T3)-free Bullet Kit REGM (BIO WHITTAKER), the cells were cultured for additional 30 minutes.

b) As stimulants, TGF-β1 (Wako Pure Chemical Industries, Ltd.), TNF-α (Genzyme), IL-1β (Genzyme), IL-6 (Genzyme) and PMA (Wako Pure Chemical Industries, Ltd.) were used. A solution was prepared by diluting each of these 5 stimulants at the final concentration of 10 ng/ml with T3-free Bullet Kit REGM (BIO WHITTAKER).

c) Just after the culture supernatants of the RPTEC and HRCE in the above item a) were removed, the solution prepared in the above item b) was added in a volume of 500 µl/well, and the cells were cultured. As the control, a mixture of the 5 stimulants dissolved in a solvent was diluted at the same ratio as the stimulants with T3-free Bullet Kit REGM (BIO WHITTAKER) to prepare a solution, and 500 µl of the solution was added to each well of RPTEC and HRCE, and the cells were cultured.

d) 0.5, 1, 2, 4, 6 and 8 hours after addition of the stimulants, the cells were recovered respectively, and total RNA was prepared by using RNeasy Mini Kit (Quiagen). The total RNA thus prepared was subjected to reverse transcription reaction using TaqMan Reverse Transcription Reagents (manufactured by Applied Biosystems, Inc.) to prepare the cDNA.

(3) Analysis of Expression of Human TCH229 Gene in Commercially Available Normal Human Cells The expression level (copy number) of human TCH229 in the cDNAs prepared from the normal human cells and the PRTEC and HRCE stimulated with the stimulants was measured by TaqMan PCR with the 2 primer DNAs used in Example 4 (that is, primer TMF (SEQ ID NO: 19) and primer TMR (SEQ ID NO: 20)) and TaqMan probe P1 (SEQ ID NO: 21). For the cDNAs prepared respectively from the normal human cells and the PRTEC and HRCE stimulated with the stimulants, the expression level (copy number) of ribosomal RNA (18S) was assayed by using Eukaryotic 18S rRNA Pre-Developed TaqMan Assay Reagents (manufactured by Applied Biosystems, Inc.), and the expression level (copy number) of human glyceraldehyde-3-phosphate dehydrogenase (GAPDH) was also assayed by using human GAPD (GAPDH) (manufactured by Applied Biosystems, Inc.). Using TaqMan Universal PCR Master Mix (manufactured by Applied Biosystems, Inc.), the reaction was carried out by initially reacting at 50° C. for 2 minutes and then at 95° C. for 10 minutes, followed by 40 cycles each consisting of a reaction at 95° C. for 15 seconds and at 60° C. for 1 minute, while detection was simultaneously made on the ABI PRISM 7900 sequence detection system (manufactured by Applied Biosystems, Inc.).

Figure 12:
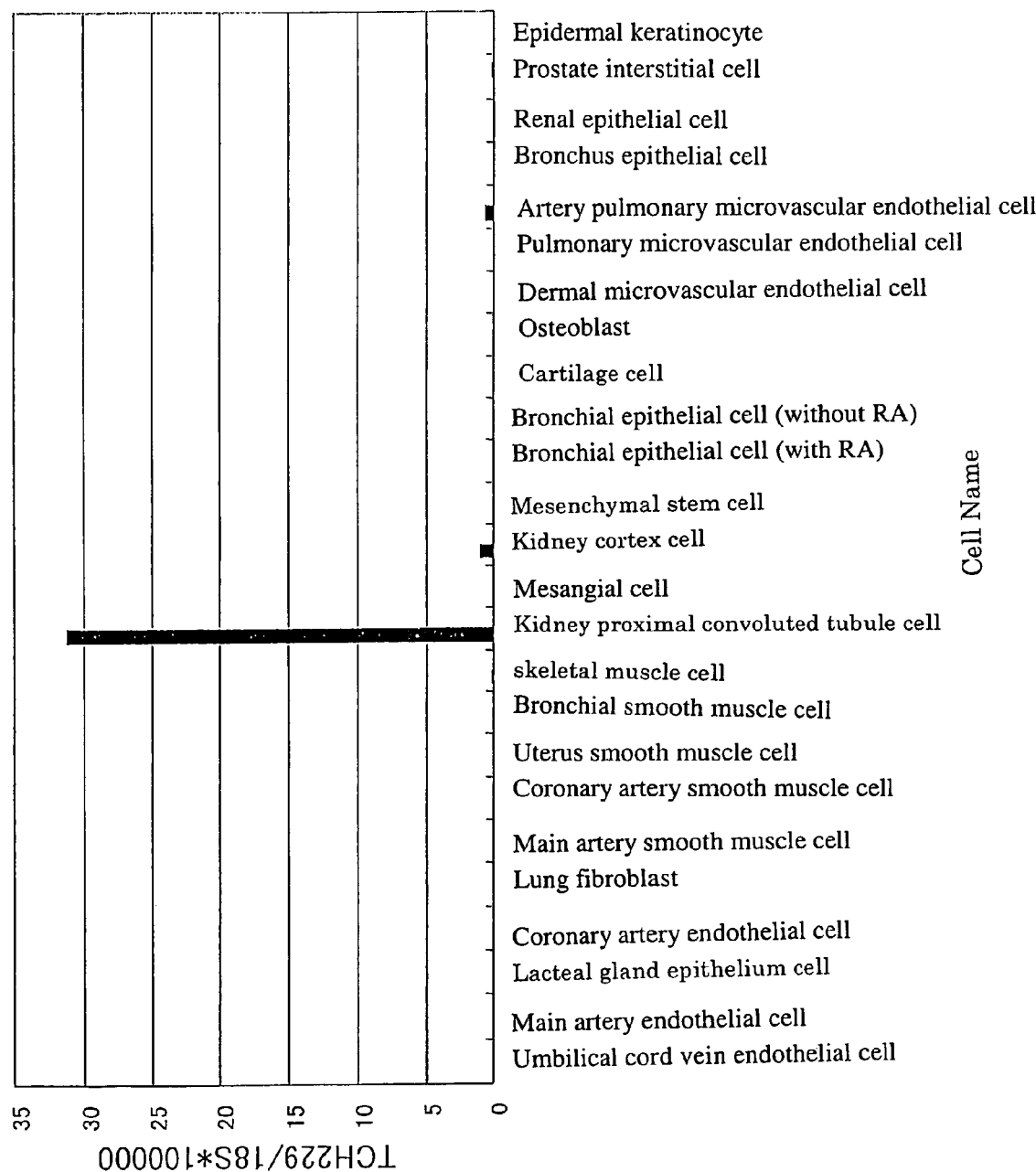
FIG. 12 shows the fluctuation of expression of human TCH229 in human normal cells. In the figure, ((expression level of human TCH229 gene relative to human 18S)×100,000)) is shown on the ordinate. Cell name is shown on the abscissa. ■ shows the absence of stimulation with TNF-α, IL-1β and IL-6 (each 10 ng/ml), and □ shows the presence of stimulation with TNF-α, IL-1β and IL-6 (each 10 ng/ml).

The fluctuation of expression of human TCH229 in the human normal cells is shown in FIG. 12. The cells given the symbol * in Table 2 were stimulated with TNF-α, IL-1β and IL-6 (each 10 ng/ml), but as compared with the non-stimulated cells, the fluctuation of expression was hardly recognized, and expression was hardly recognized.

Figure 13:
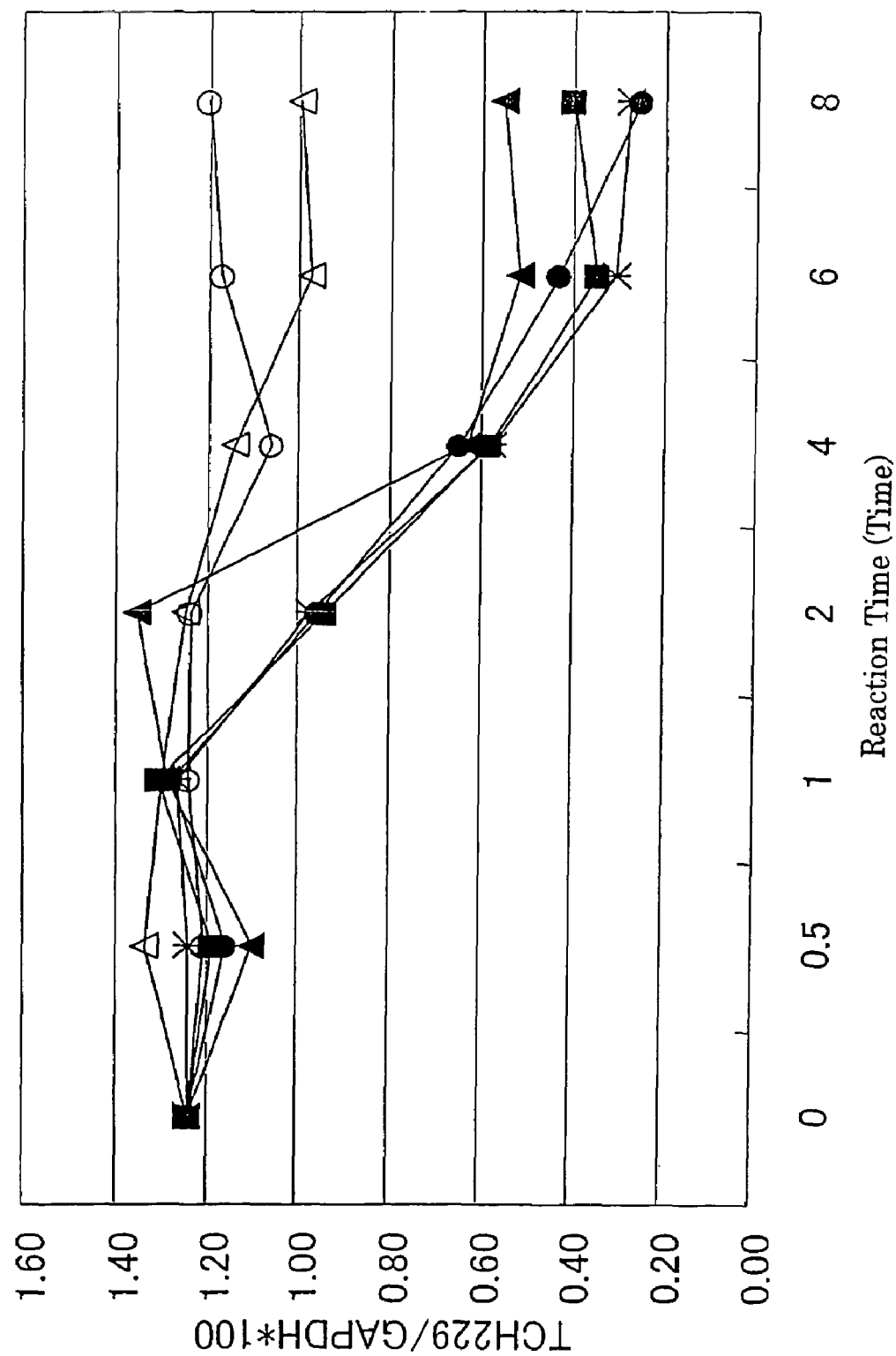
FIG. 13 shows the fluctuation of expression of human TCH229 in RPTEC stimulated with stimulants. In the figure, ((the expression level of human TCH229 gene relative to human GAPDH)×100)) is shown on the ordinate. The reaction time with stimulants is shown on the abscissa. -●- shows TGF-β1, -■- shows PMA, -▲- shows TNF-α, -*- shows IL-1β, -○- shows IL-6, and -Δ- shows control.
Figure 14:
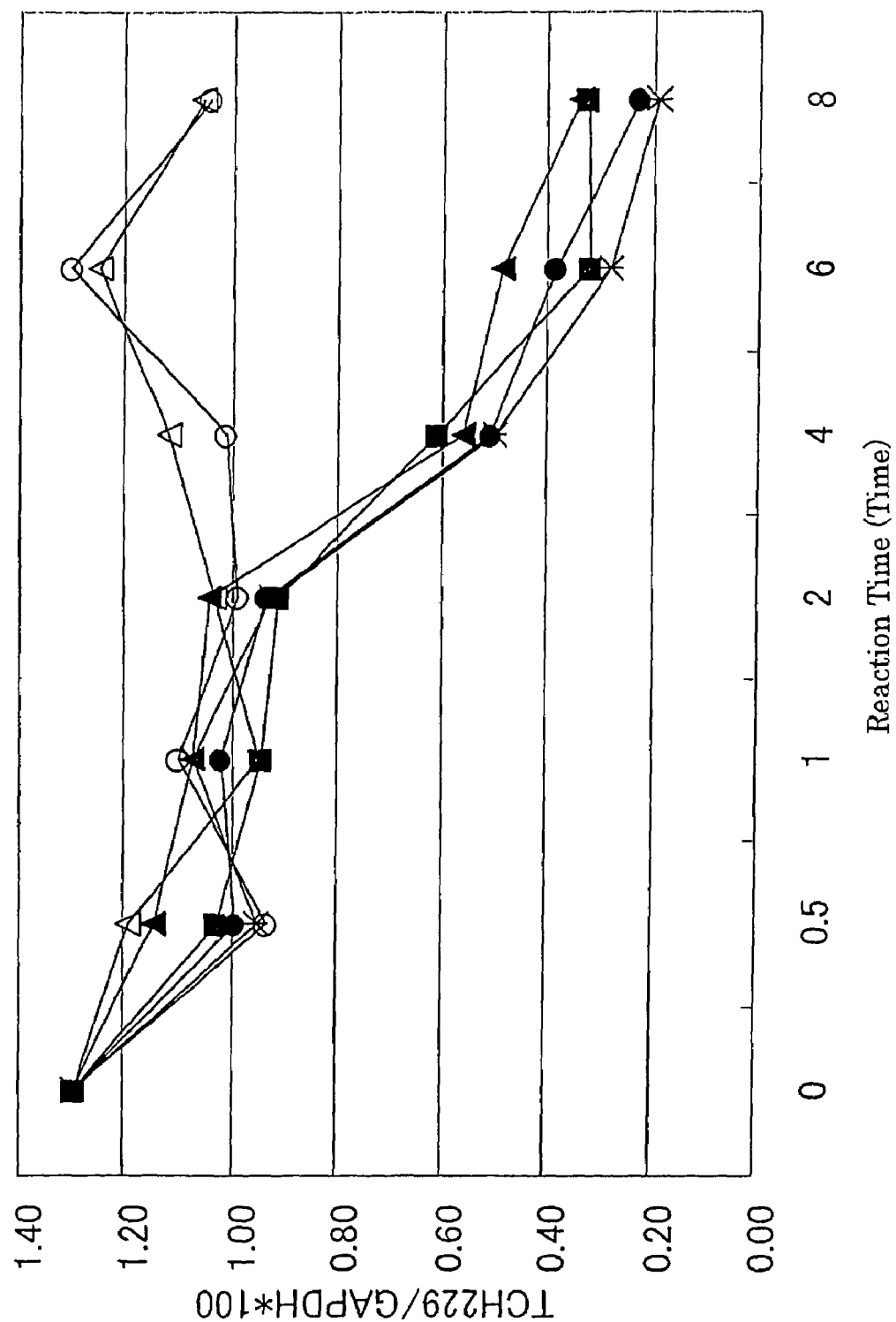
FIG. 14 shows the fluctuation of expression of human TCH229 in HRCE stimulated with stimulants. In the figure, ((the expression level of human TCH229 gene relative to human GAPDH)×100)) is shown on the ordinate. The reaction time with stimulants is shown on the abscissa. -●- shows TGF-β1, -■- shows PMA, -▲- shows TNF-α, -*- shows IL-1β, -○- shows IL-6, and -Δ- shows control.

The fluctuation of expression of human TCH229 in RPTEC stimulated with the stimulants is shown in FIG. 13, and the fluctuation of expression of human TCH229 in HRCE stimulated with the stimulants is shown in FIG. 14.

Specific expression of the human TCH229 gene product (mRNA) was observed in the renal proximal urine tubule epithelial cell, and slight expression was observed in the renal cortical epithelial cells. When RPTEC and HRCE were stimulated with TGF-β1, TNF-α, IL-1β or PMA, the expression of human TCH229 could be confirmed to be decreased depending on culture time as compared with the control.

EXAMPLE 18

Analysis of Expression of Rat TCH229 Gene Product in the Rat Kidney in Renal Disease Models (Wistar Fatty, SHC, Zucker Fatty)

As disease model animals, 3 kinds of rats i.e. Wistar Fatty rat (WF rat), Zucker Fatty rat (ZF rat) and spontaneous hypercholesterolemic rat (SHC rat) were used, and as their corresponding controls, Wistar Lean rat (WL rat) corresponding to WF rat, Zucker Lean rat (ZL rat) corresponding to ZF rat, and SD rat (SD rat) corresponding to SHC rat were used.

The Wistar Fatty rat (WF rat) shows symptoms characteristic of diabetes in addition to renal hypofunction and is thus reported as a diabetic nephropathy model (Frontiers in diabetes research, lessons from animal diabetes II, 535-541, 1988); similar the WF rat, the Zucker Fatty rat (ZF rat) shows both renal hypofunction and diabetic symptoms and is thus reported as a diabetic nephropathy model (Kidney international, 52, S218-S220, 1997); and the spontaneous hypercholesterolemic rat (SHC rat) shows symptoms similar to human focal glomerular sclerosis and is thus reported as a focal glomerular sclerosis model (Journal of Japanese Society of Nephrology, 37, 91-99, 1995).

(1) The disease model animals and the control animals were bred under the same conditions, and the total RNA was extracted in the following manner from the WF rat and WL rat which were 13-week-old (before onset), 20-week-old (after onset), 42-week-old (developing stage) and 68-week-old (renal function depression stage) respectively; the total RNA was extracted from the SHC rat and SD rat which were 6-week-old (before onset), 12-week-old (after onset), 20-week-old (developing stage) and 26 to 30-week-old (renal function depression stage) respectively; and the total RNA was extracted from the ZF rat and ZL rat which were 8-week-old (before onset) and 27-week-old (after onset) respectively.

Each kidney from the WF rat group (n=5 in each group of the same age), the WL rat group (n=5 in each group of the same age), the SHC rat group (n=5 in each group of the same age), the SD rat group (n=5 in each group of the same age), the ZF rat group (n=9 in each group of the same age), and the ZL rat group (n=9 in each group of the same age) was sliced in an institutional face including mamillary parts to prepare an about 100 mg slice, and the total RNA was extracted by using ISOGEN according to its attached manual. Contaminant DNA was removed by using QIAGEN RNeasy Mini kit (manufactured by Qiagen) and RNase-Free DNase set (manufactured by Qiagen). The total RNA thus prepared was subjected to reverse transcription reaction using TaqMan Reverse Transcription Reagents (manufactured by Applied Biosystems, Inc.) to prepare the cDNA.

Figure 15:
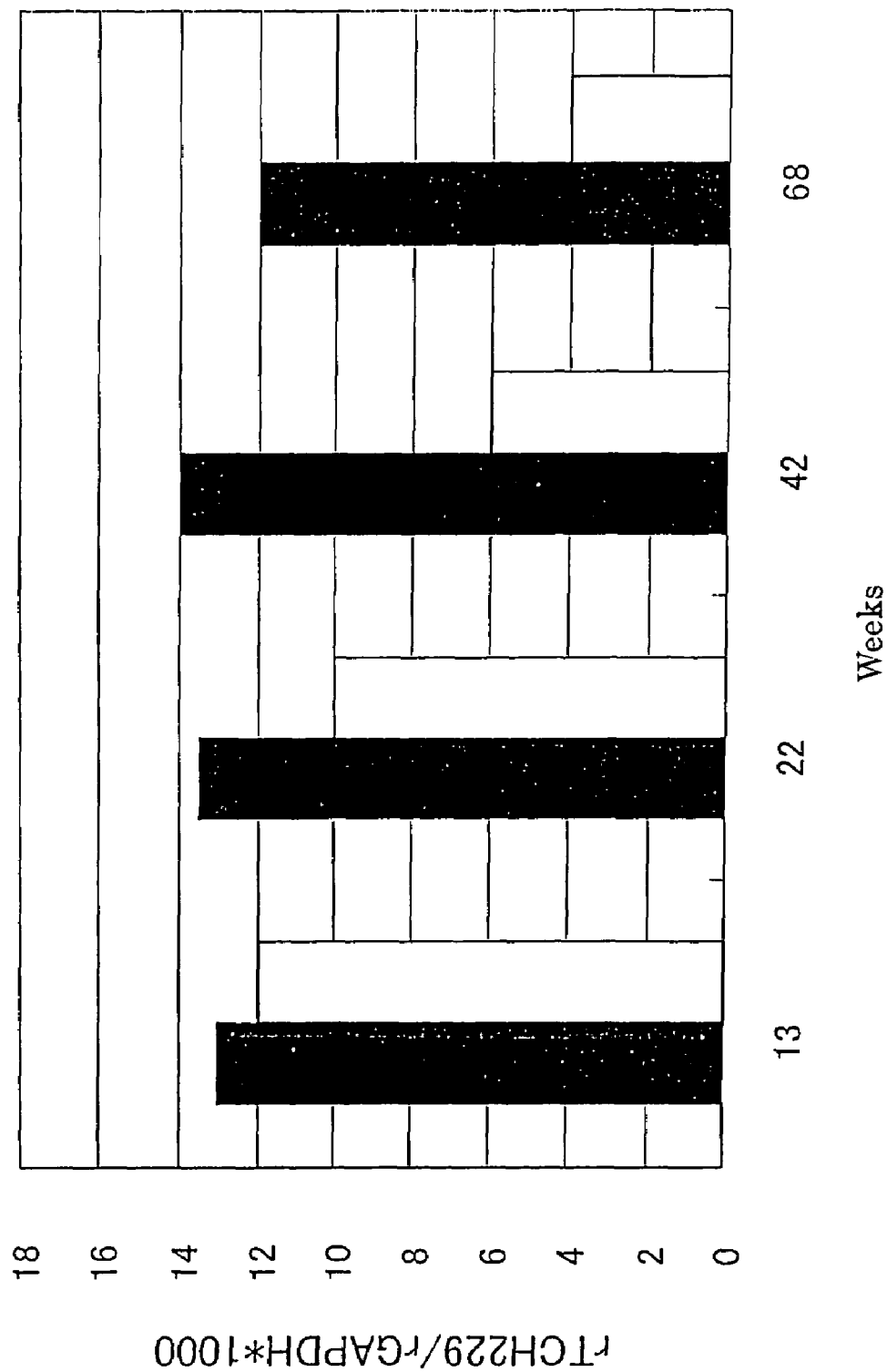
FIG. 15 shows the expression level of rat TCH229 gene product. In the figure, ((the expression level of rat TCH229 gene relative to rodent GAPDH)×1,000)) is shown on the ordinate, and the age (unit: week-old) of rats from which kidneys were removed. -□- shows results of an experimental group (WF rat), and -■- shows results of a control group (WL rat).
Figure 16:
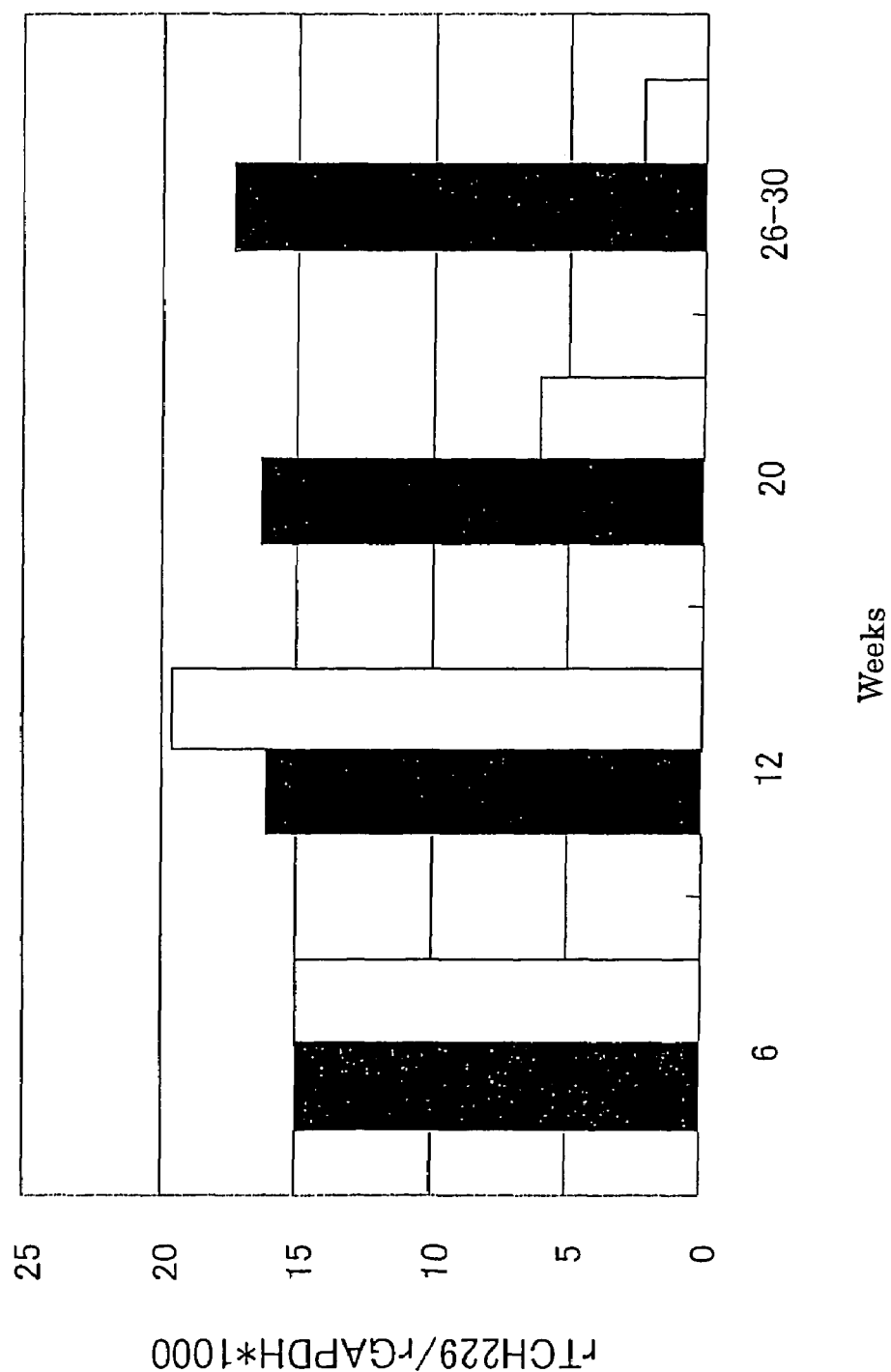
FIG. 16 shows the expression level of rat TCH229 gene product. In the figure, ((the expression level of rat TCH229 gene relative to rodent GAPDH)×1,000)) is shown on the ordinate, and the age (unit: week-old) of rats from which kidneys were removed. -□- shows results of an experimental group (SHC rat), and -■- shows results of a control group (SD rat).
Figure 17:
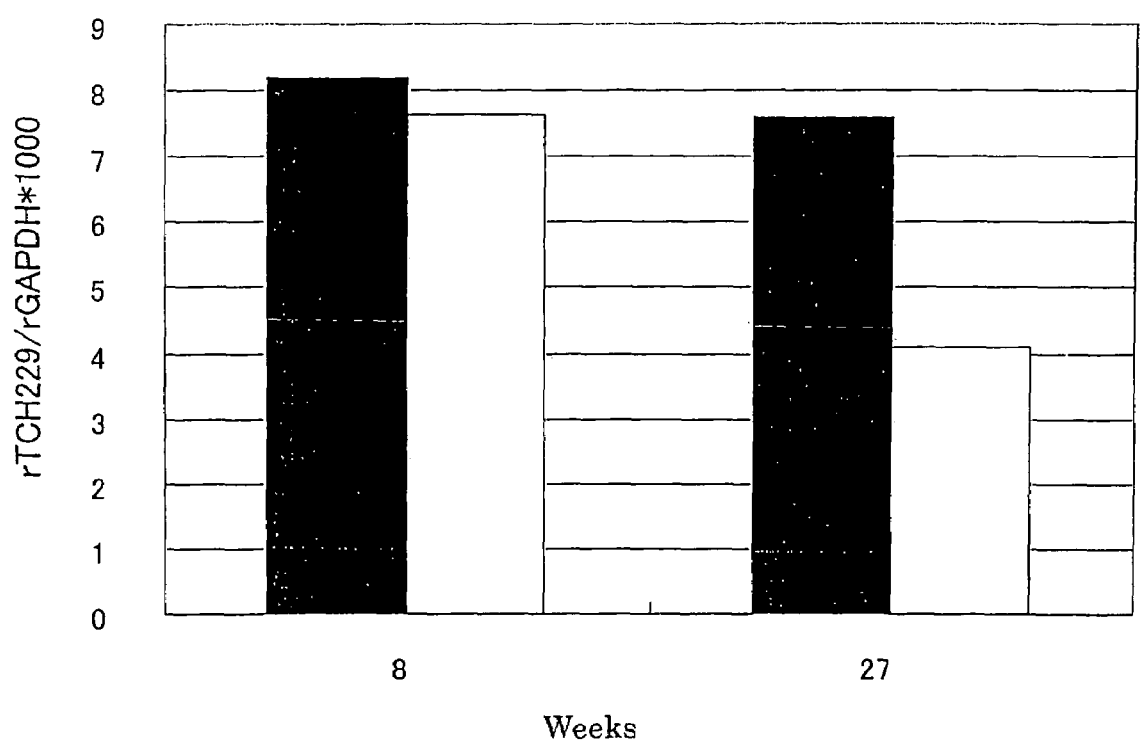
FIG. 17 shows the expression level of rat TCH229 gene product. In the figure, ((the expression level of rat TCH229 gene relative to rodent GAPDH)×1,000)) is shown on the ordinate, and the age (unit: week-old) of rats from which kidneys were removed. -□- shows results of an experimental group (ZF rat), and -■- shows results of a control group (ZL rat).

(2) Analysis of Expression of Rat TCH229 Gene Product in the Kidney in the Renal Disease Model Rat For the renal disease model rat kidney cDNA prepared above in (1), the expression level (copy number) of rat TCH229 was measured by TaqMan PCR by using the 2 primer DNAs used in Example 12 (that is, primer rTMF (SEQ ID NO: 70) and primer rTMR (SEQ ID NO: 69)) and TaqMan probe rP1 (SEQ ID NO: 76). The expression level (copy number) of rodent glyceraldehyde-3-phosphate dehydrogenase (GAPDH) was also assayed for the same cDNA using TaqMan rodent GAPDH control reagents (manufactured by Applied Biosystems, Inc.). Using TaqMan Universal PCR Master Mix (manufactured by Applied Biosystems, Inc.), the reaction was carried out by initially reacting at 50° C. for 2 minutes and then at 95° C. for 10 minutes, followed by 40 cycles each consisting of a reaction at 95° C. for 15 seconds and at 60° C. for 1 minute, while detection was simultaneously made on the ABI PRISM 7900 sequence detection system (manufactured by Applied Biosystems, Inc.). The results of the WF rat group are shown in FIG. 15, and the results of the SHC rat group in FIG. 16, and the results of the ZF rat group in FIG. 17.

In the kidneys in the 3 kinds of renal disease model rats, renal disorders occurred and then the expression of rat TCH229 was reduced as compared with the control group. From this result, it can be considered that TCH229 is involved in renal diseases such as nephropathy.

INDUSTRIAL APPLICABILITY

The protein, polynucleotide and antibody of the present invention are useful for example as diagnostic markers for example renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease, etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. The compound that promotes or inhibits the activity of the protein, the compound that promotes or inhibits the expression of a gene for the protein, and the compound that promotes or inhibits the expression of the protein, which are obtained by the screening method using the protein, polynucleotide or antibody can be used as prophylactic/therapeutic agents for renal diseases (e.g., renal insufficiency, glomerulonephritis, diabetic nephropathy, focal glomerular sclerosis, nephritic syndrome, renal edema, tubulointerstitial nephritis, nephrosclerosis, uremia etc.), hepatic diseases (e.g., hepatocirrhosis, hepatitis, alcoholic liver disease etc.), pancreatic disorders (e.g., pancreatitis etc.), immune diseases caused by thymic abnormalities, genital diseases (e.g., prostate enlargement, prostatitis, testis neuritis, ovarian cystoma etc.), digestive diseases (e.g., irritable bowel syndrome, ulcerous colitis, ischemic colitis, gastritis etc.), spleen diseases (e.g., spleen hyperfunction, splenomegaly syndrome etc.), cancers (e.g., lung cancer, kidney cancer, hepatoma, non-small cell lung cancer, ovarian cancer, prostate cancer, stomach cancer, bladder cancer, breast cancer, uterine cervix cancer, colon cancer, rectum cancer, pancreatic cancer, thymoma, myelocytic leukemia etc.), respiratory diseases (e.g., sclerotitis, pneumonia, chronic obstructive pulmonary disease, asthma etc.), osteomyelitis, diabetes, hypertension, ischemia-reperfusion injury, retinitis, central nerve diseases (e.g., epilepsy, Alzheimer's disease, Parkinson's syndrome, schizophrenia etc.), skin diseases (e.g., atopic dermatitis, sebrrhoticus dermatitis etc.), thyroid hormone-related diseases (e.g., Refetoff syndrome, Basedow's disease, cretinism, hyperthyroidism etc.), etc. Preferably, they are used as prophylactic/therapeutic agents for renal diseases and thyroid hormone-related diseases, more preferably as prophylactic/therapeutic agent for diabetic nephropathy.

The invention claimed is:

1. An isolated protein comprising the amino acid sequence of SEQ ID NO: 1, or a salt thereof.

2. A composition comprising the protein, or salt thereof, according to claim 1, and a pharmaceutically acceptable carrier, excipient or diluent.

3. The protein according to claim 1, which consists of the amino acid sequence of SEQ ID NO: 1, or a salt thereof.

* * * * *

```
SEQUENCE LISTING

<160> NUMBER OF SEQ ID NOS: 84

<210> SEQ ID NO 1
<211> LENGTH: 724
<212> TYPE: PRT
<213> ORGANISM: Homo sapiens

<400> SEQUENCE: 1

Met Lys Ser Ala Lys Gly Ile Glu Asn Leu Ala Phe Val Pro Ser Ser
                 5                  10                  15

Pro Asp Ile Leu Arg Arg Leu Ser Ala Ser Pro Ser Gln Ile Glu Val
             20                  25                  30

Ser Ala Leu Ser Ser Asp Pro Gln Arg Glu Asn Ser Gln Pro Gln Glu
         35                  40                  45

Leu Gln Lys Pro Gln Glu Pro Gln Lys Ser Pro Glu Pro Ser Leu Pro
     50                  55                  60

Ser Ala Pro Pro Asn Val Ser Glu Glu Lys Leu Arg Ser Leu Ser Leu
 65                  70                  75                  80

Ser Glu Phe Glu Glu Gly Ser Tyr Gly Trp Arg Asn Phe His Pro Gln
                 85                  90                  95

Cys Leu Gln Arg Cys Asn Thr Pro Gly Gly Phe Leu Leu His Tyr Cys
            100                 105                 110

Leu Leu Ala Val Thr Gln Gly Ile Val Val Asn Gly Leu Val Asn Ile
        115                 120                 125

Ser Ile Ser Thr Val Glu Lys Arg Tyr Glu Met Lys Ser Ser Leu Thr
    130                 135                 140
```

```
Gly Leu Ile Ser Ser Ser Tyr Asp Ile Ser Phe Cys Leu Leu Ser Leu
145                 150                 155                 160

Phe Val Ser Phe Phe Gly Glu Arg Gly His Lys Pro Arg Trp Leu Ala
                165                 170                 175

Phe Ala Ala Phe Met Ile Gly Leu Gly Ala Leu Val Phe Ser Leu Pro
            180                 185                 190

Gln Phe Phe Ser Gly Glu Tyr Lys Leu Gly Ser Leu Phe Glu Asp Thr
        195                 200                 205

Cys Val Thr Thr Arg Asn Ser Thr Ser Cys Thr Ser Ser Thr Ser Ser
210                 215                 220

Leu Ser Asn Tyr Leu Tyr Val Phe Ile Leu Gly Gln Leu Leu Leu Gly
225                 230                 235                 240

Ala Gly Gly Thr Pro Leu Tyr Thr Leu Gly Thr Ala Phe Leu Asp Asp
                245                 250                 255

Ser Val Pro Thr His Lys Ser Ser Leu Tyr Ile Gly Thr Gly Tyr Ala
            260                 265                 270

Met Ser Ile Leu Gly Pro Ala Ile Gly Tyr Val Leu Gly Gly Gln Leu
        275                 280                 285

Leu Thr Ile Tyr Ile Asp Val Ala Met Gly Glu Ser Thr Asp Val Thr
290                 295                 300

Glu Asp Asp Pro Arg Trp Leu Gly Ala Trp Trp Ile Gly Phe Leu Leu
305                 310                 315                 320

Ser Trp Ile Phe Ala Trp Ser Leu Ile Ile Pro Phe Ser Cys Phe Pro
                325                 330                 335

Lys His Leu Pro Gly Thr Ala Glu Ile Gln Ala Gly Lys Thr Ser Gln
            340                 345                 350

Ala His Gln Ser Asn Ser Asn Ala Asp Val Lys Phe Gly Lys Ser Ile
        355                 360                 365

Lys Asp Phe Pro Ala Ala Leu Lys Asn Leu Met Lys Asn Ala Val Phe
370                 375                 380

Met Cys Leu Val Leu Ser Thr Ser Ser Glu Ala Leu Ile Thr Thr Gly
385                 390                 395                 400

Phe Ala Thr Phe Leu Pro Lys Phe Ile Glu Asn Gln Phe Gly Leu Thr
                405                 410                 415

Ser Ser Phe Ala Ala Thr Leu Gly Gly Ala Val Leu Ile Pro Gly Ala
            420                 425                 430

Ala Leu Gly Gln Ile Leu Gly Gly Phe Leu Val Ser Lys Phe Arg Met
        435                 440                 445

Thr Cys Lys Asn Thr Met Lys Phe Ala Leu Phe Thr Ser Gly Val Ala
450                 455                 460

Leu Thr Leu Ser Phe Val Phe Met Tyr Ala Lys Cys Glu Asn Glu Pro
465                 470                 475                 480

Phe Ala Gly Val Ser Glu Ser Tyr Asn Gly Thr Gly Glu Leu Gly Asn
                485                 490                 495

Leu Ile Ala Pro Cys Asn Ala Asn Cys Asn Cys Ser Arg Ser Tyr Tyr
            500                 505                 510

Tyr Pro Val Cys Gly Asp Gly Val Gln Tyr Phe Ser Pro Cys Phe Ala
        515                 520                 525

Gly Cys Ser Asn Pro Val Ala His Arg Lys Pro Lys Val Tyr Tyr Asn
530                 535                 540

Cys Ser Cys Ile Glu Arg Lys Thr Glu Ile Thr Ser Thr Ala Glu Thr
545                 550                 555                 560

Phe Gly Phe Glu Ala Lys Ala Gly Lys Cys Glu Thr His Cys Ala Lys
```

```
                        565                 570                 575
Leu Pro Ile Phe Leu Cys Ile Phe Phe Ile Val Ile Ile Phe Thr Phe
                580                 585                 590

Met Ala Gly Thr Pro Ile Thr Val Ser Ile Leu Arg Cys Val Asn His
                595                 600                 605

Arg Gln Arg Ser Leu Ala Leu Gly Ile Gln Phe Met Val Leu Arg Leu
                610                 615                 620

Leu Gly Thr Ile Pro Gly Pro Ile Ile Phe Gly Phe Thr Ile Asp Ser
625                 630                 635                 640

Thr Cys Ile Leu Trp Asp Ile Asn Asp Cys Gly Ile Lys Gly Ala Cys
                645                 650                 655

Trp Ile Tyr Asp Asn Ile Lys Met Ala His Met Leu Val Ala Ile Ser
                660                 665                 670

Val Thr Cys Lys Val Ile Thr Met Phe Phe Asn Gly Phe Ala Ile Phe
                675                 680                 685

Leu Tyr Lys Pro Pro Pro Ser Ala Thr Asp Val Ser Phe His Lys Glu
                690                 695                 700

Asn Ala Val Val Thr Asn Val Leu Ala Glu Gln Asp Leu Asn Lys Ile
705                 710                 715                 720

Val Lys Glu Gly

<210> SEQ ID NO 2
<211> LENGTH: 2172
<212> TYPE: DNA
<213> ORGANISM: Homo sapiens

<400> SEQUENCE: 2
atgaagagcg ccaaaggtat tgagaacttg gcttttgtcc cctccagccc agacatcctg      60
cgccgcttgt ctgcgtcgcc ctcccaaatc gaagtctctg ccttgtcctc tgaccccaa      120 agagagaatt ctcagccaca ggagcttcag aagcccagg agcccagaa gtcacccgag       180 ccatctctgc cttcagcccc tcccaatgtc tccgaagaga agctccggtc actgtcgctg      240
tccgagtttg aggaggggtc ttacggctgg aggaacttcc atcctcaatg tctccagcgc     300
tgcaacacac ctggaggctt tctgcttcac tactgcctct ggccgtcac gcaaggtatt      360 gtagttaatg gcctagtaaa tattagcatt tccactgttg agaagcgtta tgaaatgaag     420
agttccctga ctggcctgat tcatcaagc tacgatattt cattctgttt gttgtcttta     480
tttgtatcat tctttggtga aagaggacat aagccgagat ggcttgcatt tgcagccttt    540
atgattggac tgggagcact tgtattctca ttgccacaat ttttcagtgg agaatataaa    600
ttggggtctc tttttgaaga cacttgtgta acaacaagga atagcaccag ttgtacatct    660
tcaacttctt cactttctaa ctacttgtat gtcttcatct gggacaact attgctgggg    720 gcaggaggaa ctcctcttta tactctggga acagcctttc ttgatgattc tgtgcccaca    780
cacaagtctt ctctctatat aggaaccggt tatgctatgt caatcttagg ccctgctatt    840
ggctatgtat tgggaggaca actgctaacc atatacattg atgttgctat gggagaaagc    900
actgatgtca ctgaggatga tccgcgatgg ttgggagctt ggtggattgg gtttcttcta    960
tcatggatct ttgcttggtc tttaataata cctttttctt gctttccaaa acatttacca   1020
ggtacagcag aaattcaagc tggaaaaact ccccaggctc atcagagtaa tagtaatgca   1080
gatgtgaaat ttggaaaaag tattaaagat tttccagctg ctctaaagaa tttgatgaag   1140
aatgctgtct ttatgtgttt agttctatca acttcttcag aagccttaat tactactgga   1200
```

```
tttgctacat ttttacctaa atttatagaa aatcaattcg gattgacatc cagcttcgca    1260
gctactcttg gagggctgt tttaattcct ggagctgctc tcggtcaaat tttaggtggc    1320
ttccttgttt caaaattcag aatgacatgt aaaaacacaa tgaagtttgc actgttcaca    1380
tctggagttg cacttacgct gagttttgta tttatgtatg ccaaatgtga aaatgagcca    1440
tttgctggtg tatctgaatc atataatggg actggagaat tgggaaactt gatagcccct    1500
tgtaatgcca attgtaactg ttcgcgatca tattattatc ctgtctgtgg agatggagtc    1560
caatattttt ctccctgctt tgcaggctgt tcaaacccag ttgcacacag gaagccaaag    1620
gtatattaca actgttcctg tattgaaagg aaaacagaaa taacatccac tgcagaaact    1680
tttggttttg aagctaaagc tggaaaatgt gaaactcatt gtgcgaaact gcccatattc    1740
ctttgcattt tctttattgt aattattttt acctttatgg ccggtactcc tataactgtg    1800
tctatcctaa ggtgtgttaa tcacagacaa cggtccctag ccttgggaat acaatttatg    1860
gtccttcgat tattaggaac aattcctgga ccaattatat ttggtttcac aatagacagc    1920
acatgtattc tttgggatat aaatgattgt ggaattaaag gagcttgctg gatttatgat    1980
aacatcaaga tggcccatat gctagtagcc ataagtgtta cttgtaaagt tatcaccatg    2040
ttcttcaatg gatttgcaat cttttttgtat aaaccacctc catcagccac agatgtgtca    2100
tttcataaag agaatgcagt tgtgactaat gttttagcag aacaggatct caacaaaata    2160
gtaaaagaag gg                                                      2172

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
ccatcctaat acgactcact atagggc                                       27

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
aaacccaatc caccaagctc ccaacc                                        26

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
actcactata gggctcgagc ggc                                           23

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
```

```
ccaatccacc aagctcccaa ccatc                                            25

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
gttcctccag ccgtaagacc cctcctca                                         28

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
cggagacatt gggagggct gaagg                                             25

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
ttgggagctt ggtggattgg gtttcttc                                         28

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
gggactggag aattgggaaa cttgatagc                                        29

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cacgggggcg ctgtcacctg                                                  20

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
atcgaggtaa attttccagg tgtaa                                            25

<210> SEQ ID NO 13
<211> LENGTH: 23
<212> TYPE: DNA
```

<213> ORGANISM: Artificial Sequence
<220> FEATURE:
<223> OTHER INFORMATION: Primer

<400> SEQUENCE: 13
agggacctgg ctctgctgct ctg                                    23

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
aacagtcttc tcttttccca tttca                                  25

<210> SEQ ID NO 15
<211> LENGTH: 16
<212> TYPE: DNA
<213> ORGANISM: Artificial Sequence
<220> FEATURE:
<223> OTHER INFORMATION: Primer

<400> SEQUENCE: 15
gtaaaacgac ggccag                                            16

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
caggaaacag ctatgac                                           17

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ctgggaacag cctttcttga tgat                                   24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
cagcaagctc ctttaattcc acaa                                   24

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
tgggaggaca actgctaacc a                                      21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
atcgcggatc atcctcagtg                                                  20

<210> SEQ ID NO 21
<211> LENGTH: 32
<212> TYPE: DNA
<213> ORGANISM: Artificial Sequence
<220> FEATURE:
<223> OTHER INFORMATION: Probe

<400> SEQUENCE: 21
cattgatgtt gctatgggag aaagcactga tg                                    32

<210> SEQ ID NO 22
<211> LENGTH: 782
<212> TYPE: DNA
<213> ORGANISM: Homo sapiens

<400> SEQUENCE: 22
aagtcacccg agccatctct gccttcagcc cctcccaatg tctccgaaga gaagctccgg      60
tcactgtcgc tgtccgagtt tgaggagggg tcttacggct ggaggaactt ccatcctcaa     120
tgtctccagc gctgcaacac acctggaggc tttctgcttc actactgcct cttggccgtc     180
acgcaaggta tttgtagttaa tggcctagta aatattagca tttccactgt tgagaagcgt    240
tatgaaatga agagttccct gactggcctg atttcatcaa gctacgatat ttcattctgt     300
ttgttgtctt tatttgtatc attctttggt gaaagaggac ataagccgag atggcttgca     360
tttgcagcct ttatgattgg actgggagca cttgtattct cattgccaca atttttcagt    420
ggagaatata aattggggtc tcttttttgaa gacacttgtg taacaacaag gaatagcacc    480
agttgtacat cttcaacttc ttcactttct aactacttgt atgtcttcat cttgggacaa    540
ctattgctgg gggcaggagg aactcctctt tatactctgg gaacagcctt tcttgatgat    600
tctgtgccca cacacaagtc ttctctctat ataggaaccg ttatgctat gtcaatctta     660 ggccctgcta ttggctatgt attgggagga caactgctaa ccatatacat tgatgttgct    720
atgggagaaa gcactgatgt cactgaggat gatccgcgat ggttgggagc ttggtggatt    780
gg                                                                   782

<210> SEQ ID NO 23
<211> LENGTH: 485
<212> TYPE: DNA
<213> ORGANISM: Homo sapiens

<400> SEQUENCE: 23
ctaacgcccc cgctcagcgc tctgcgctcc agacagctgc gagctggagt aggaaggttc      60
aggcggtggc ggagagtgcg ctggaggctg gagggccagg aggcgggaag cttcccgcac    120
gggggcgctg tcacctgcct gtgggaggag ccagagaggg acctggctct gctgctctga    180
agcaccggag tcgggagaac ccatccagac atgaagagcg ccaaaggtat tgagaacttg    240
gcttttgtcc cctccagccc agacatcctg cgccgcttgt ctgcgtcgcc ctcccaaatc    300

| | |
|---|---|
| gaagtctctg ccttgtcctc tgaccccaa agagagaatt ctcagccaca ggagcttcag | 360 |
| aagccccagg agccccagaa gtcaccagag ccatctctgc cttcagcccc tcccaatgtc | 420 |
| tccgaagaga agctccggtc actgtcgctg tccgagtttg aggaggggtc ttacggctgg | 480 |
| aggaa | 485 |

<210> SEQ ID NO 24
<211> LENGTH: 792
<212> TYPE: DNA
<213> ORGANISM: Homo sapiens

<400> SEQUENCE: 24

| | |
|---|---|
| gggactggag aattgggaaa cttgatagcc ccttgtaatg ccaattgtaa ctgttcgcga | 60 |
| tcatattatt atcctgtctg tggagatgga gtccaatatt tttctccctg ctttgcaggc | 120 |
| tgttcaaacc cagttgcaca caggaagcca aggtatatt acaactgttc ctgtattgaa | 180 |
| aggaaaacag aaataacatc cactgcgaaa acttttggtt ttgaagctaa agctggaaaa | 240 |
| tgtgaaactc attgtgcgaa actgcccata ttcctttgca ttttctttat tgtaattatt | 300 |
| tttacccttta tggccggtac tcctataact gtgtctatcc taaggtgtgt taatcacaga | 360 |
| caacggtccc tagccttggg aatacaattt atggtccttc gattattagg aacaattcct | 420 |
| ggaccaatta tatttggttt cacaatagac agcacatgta ttctttggga tataaatgat | 480 |
| tgtggaatta aaggagcttg ctggatttat gataacatca agatggccca tatgctagta | 540 |
| gccataagtg ttacttgtaa agttatcacc atgttcttca atggatttgc aatcttttg | 600 |
| tataaaccac ctccatcagc cacagatgtg tcatttcata agagaatgc agttgtgact | 660 |
| aatgttttag cagaacagga tctcaacaaa atagtaaaag aagggtgaaa tgggaaaaga | 720 |
| gaagactgtt ttacacctgg aaaatttacc tcgattttta agaacacaca ttgccatggc | 780 |
| aggattatct at | 792 |

<210> SEQ ID NO 25
<211> LENGTH: 2251
<212> TYPE: DNA
<213> ORGANISM: Homo sapiens

<400> SEQUENCE: 25

| | |
|---|---|
| agggacctgg ctctgctgct ctgaagcacc ggagtcggga gaacccatcc agacatgaag | 60 |
| agcgccaaag gtattgagaa cttggctttt gtcccctcca gcccagacat cctgcgccgc | 120 |
| ttgtctgcgt cgcccctccca aatcgaagtc tctgccttgt cctctgaccc ccaaagagag | 180 |
| aattctcagc cacaggagct tcagaagccc caggagcccc agaagtcacc cgagccatct | 240 |
| ctgccttcag cccctcccaa tgtctccgaa gagaagctcc ggtcactgtc gctgtccgag | 300 |
| tttgaggagg ggtcttacgg ctggaggaac ttccatcctc aatgtctcca gcgctgcaac | 360 |
| acacctggag gctttctgct tcactactgc ctcttggccg tcacgcaagg tattgtagtt | 420 |
| aatggcctag taaatattag catttccact gttgagaagc gttatgaaat gaagagttcc | 480 |
| ctgactggcc tgatttcatc aagctacgat atttcattct gtttgttgtc tttatttgta | 540 |
| tcattctttg gtgaaagagg acataagccg agatggcttg catttgcagc ctttatgatt | 600 |
| ggactggag cacttgtatt ctcattgcca caattttca gtggagaata taaattgggg | 660 |
| tctcttttg aagacacttg tgtaacaaca aggaatagca ccagttgtac atcttcaact | 720 |
| tcttcacttt ctaactactt gtatgtcttc atcttgggac aactattgct gggggcagga | 780 |
| ggaactcctc tttatactct gggaacagcc tttcttgatg attctgtgcc cacacacaag | 840 |

-continued

```
tcttctctct ataTaggaac cggttatgct atgtcaatct taggccctgc tattggctat      900
gtattgggag acaactgct  aaccatatac attgatgttg ctatgggaga agcactgat       960
gtcactgagg atgatccgcg atggttggga gcttggtgga ttgggtttct tctatcatgg     1020
atctttgctt ggtctttaat aataccttt  tcttgctttc caaaacattt accaggtaca     1080
gcagaaattc aagctggaaa aacttcccag gctcatcaga gtaatagtaa tgcagatgtg     1140
aaatttggaa aaagtattaa agattttcca gctgctctaa agaatttgat gaagaatgct     1200
gtctttatgt gtttagttct atcaacttct tcagaagcct taattactac tggatttgct     1260
acatttttac ctaaatttat agaaaatcaa ttcggattga catccagctt cgcagctact     1320
cttgagggg  ctgttttaat tcctggagct gctctcggtc aaattttagg tggcttcctt     1380
gtttcaaaat tcagaatgac atgtaaaaac acaatgaagt ttgcactgtt cacatctgga     1440
gttgcactta cgctgagttt tgtatttatg tatgccaaat gtgaaaatga gccatttgct     1500
ggtgtatctg aatcatataa tgggactgga gaattgggaa acttgatagc cccttgtaat     1560
gccaattgta actgttcgcg atcatattat tatcctgtct gtggagatgg agtccaatat     1620
ttttctccct gctttgcagg ctgttcaaac ccagttgcac acaggaagcc aaaggtatat     1680
tacaactgtt cctgtattga aaggaaaaca gaaataacat ccactgcaga aacttttggt     1740
tttgaagcta aagctggaaa atgtgaaact cattgtgcga aactgcccat attcctttgc     1800
attttcttta ttgtaattat ttttaccttt atggccggta ctcctataac tgtgtctatc     1860
ctaaggtgtg ttaatcacag acaacggtcc ctagccttgg gaatacaatt tatggtcctt     1920
cgattattag gaacaattcc tggaccaatt atatttggtt tcacaataga cagcacatgt     1980
attctttggg atataaatga ttgtggaatt aaaggagctt gctggattta tgataacatc     2040
aagatggccc atatgctagt agccataagt gttacttgta aagttatcac catgttcttc     2100
aatggatttg caatcttttt gtataaacca cctccatcag ccacagatgt gtcatttcat     2160
aaagagaatg cagttgtgac taatgtttta gcagaacagg atctcaacaa aatagtaaaa     2220
gaagggtgaa atgggaaaag agaagactgt t                                    2251
```

<210> SEQ ID NO 26
<211> LENGTH: 722
<212> TYPE: PRT
<213> ORGANISM: Mus musculus

<400> SEQUENCE: 26

```
Met Gln Gly Ser Lys Gly Ile Glu Asn Pro Ala Phe Val Pro Ser Ser
              5                  10                  15
Pro Gly Thr Pro Arg Arg Ala Ser Ala Ser Pro Ser Gln Val Glu Val
         20                  25                  30
Ser Ala Val Ala Ser Arg Asn Gln Asn Gly Gly Ser Gln Pro Arg Glu
     35                  40                  45
Ser Glu Glu Pro Gln Lys Ser Thr Glu Pro Ser Pro Pro Ser Ser Asn
 50                  55                  60
Pro Pro Ala Ser Asp Glu Pro Pro Gly Ser Gln Leu Ser Glu Leu Glu
 65                  70                  75                  80
Glu Gly Pro Cys Gly Trp Arg Gly Phe His Pro Gln Cys Leu Gln Arg
                 85                  90                  95
Cys Asn Thr Pro Gln Gly Phe Leu Leu His Tyr Cys Leu Leu Ala Leu
            100                 105                 110
Thr Gln Gly Ile Val Val Asn Gly Leu Val Asn Ile Ser Ile Ser Thr
```

```
            115                 120                 125
Ile Glu Lys Arg Tyr Glu Met Lys Ser Ser Leu Thr Gly Leu Ile Ser
    130                 135                 140

Ser Ser Tyr Asp Ile Ser Phe Cys Val Leu Ser Leu Phe Val Ser Phe
145                 150                 155                 160

Phe Gly Glu Arg Gly His Lys Pro Arg Trp Leu Ala Phe Ala Ser Phe
                165                 170                 175

Met Ile Gly Leu Gly Ala Leu Val Phe Ser Leu Pro His Phe Phe Ser
            180                 185                 190

Gly Arg Tyr Glu Leu Gly Ser Ile Phe Glu Asp Thr Cys Leu Thr Arg
        195                 200                 205

Asn Ser Thr Arg Cys Ser Ser Ser Thr Ser Leu Leu Ser Asn Tyr Phe
    210                 215                 220

Tyr Val Phe Val Leu Gly Gln Leu Leu Leu Gly Thr Gly Gly Thr Pro
225                 230                 235                 240

Leu Tyr Thr Leu Gly Thr Ala Phe Ile Asp Asp Ser Val Pro Thr His
                245                 250                 255

Lys Ser Ser Leu Tyr Ile Gly Ile Gly Tyr Ser Met Ser Ile Leu Gly
            260                 265                 270

Pro Ala Ile Gly Tyr Val Leu Gly Gly Gln Leu Leu Thr Met Tyr Ile
        275                 280                 285

Asp Ile Ala Met Gly Gln Ser Ser Asp Leu Thr Glu Asp Asp Pro Arg
    290                 295                 300

Trp Leu Gly Ala Trp Trp Ile Gly Phe Leu Leu Ala Trp Leu Phe Ala
305                 310                 315                 320

Trp Ser Leu Ile Met Pro Phe Ser Cys Phe Pro Lys His Leu Pro Gly
                325                 330                 335

Thr Ala Lys Ile Gln Ala Gly Lys Thr Ser Gln Thr His Gln Asn Asn
            340                 345                 350

Ser Thr Ser Phe Gln His Thr Asp Glu Asn Phe Gly Lys Ser Ile Lys
        355                 360                 365

Asp Phe Pro Thr Ala Val Lys Asn Leu Met Arg Asn Thr Val Phe Ile
    370                 375                 380

Cys Leu Val Leu Ser Thr Thr Ser Glu Ala Leu Ile Thr Thr Gly Phe
385                 390                 395                 400

Ala Thr Phe Leu Pro Lys Phe Ile Glu Asn Gln Gly Leu Thr Ser
                405                 410                 415

Ser Phe Ala Ala Thr Leu Gly Gly Ala Val Leu Ile Pro Gly Ala Ala
            420                 425                 430

Leu Gly Gln Ile Leu Gly Gly Val Leu Val Ser Lys Phe Lys Met Lys
        435                 440                 445

Cys Lys Asn Thr Met Lys Phe Ala Leu Cys Thr Ser Gly Val Ala Leu
    450                 455                 460

Val Leu Ser Phe Val Phe Ile Tyr Ala Lys Cys Glu Asn Glu Pro Phe
465                 470                 475                 480

Ala Gly Val Ser Glu Ser Tyr Asn Gly Thr Gly Glu Met Gly Asn Leu
                485                 490                 495

Thr Ala Pro Cys Asn Ala Asn Cys Asn Cys Leu Arg Ser Tyr Tyr Tyr
            500                 505                 510

Pro Leu Cys Gly Ser Asp Gly Ile Gln Tyr Phe Ser Pro Cys Phe Ala
        515                 520                 525

Gly Cys Leu Asn Ser Val Ser Asn Arg Lys Pro Lys Val Tyr Tyr Asn
    530                 535                 540
```

```
Cys Ser Cys Ile Glu Arg Lys Ile Thr Ser Thr Ala Glu Ser Thr Asp
545                 550                 555                 560

Phe Glu Ala Lys Ala Gly Lys Cys Arg Thr Arg Cys Ser Asn Leu Pro
                565                 570                 575

Ile Phe Leu Gly Ile Phe Phe Ile Thr Val Ile Phe Thr Phe Met Ala
            580                 585                 590

Gly Thr Pro Ile Thr Val Ser Ile Leu Arg Cys Val Asn His Arg His
        595                 600                 605

Arg Ser Leu Ala Leu Gly Val Gln Phe Met Leu Leu Arg Leu Leu Gly
    610                 615                 620

Thr Ile Pro Gly Pro Ile Ile Phe Gly Val Ile Ile Asp Ser Thr Cys
625                 630                 635                 640

Val Leu Trp Asp Val Asn Glu Cys Gly Ile Lys Gly Ala Cys Trp Ile
                645                 650                 655

Tyr Asp Asn Ile Lys Met Ala His Met Leu Val Ala Ile Ser Val Thr
            660                 665                 670

Cys Lys Val Ile Thr Ile Phe Phe Asn Gly Leu Ala Ile Val Leu Tyr
        675                 680                 685

Lys Pro Pro Pro Pro Gly Thr Glu Val Ser Phe Gln Ser Gln Asn Val
    690                 695                 700

Ile Val Ser Thr Ile Ser Val Glu Glu Asp Leu Asp Lys Ala Glu Asn
705                 710                 715                 720

Glu Gly

<210> SEQ ID NO 27
<211> LENGTH: 2166
<212> TYPE: DNA
<213> ORGANISM: Mus musculus

<400> SEQUENCE: 27
atgcagggct ccaaaggaat agagaacccg gctttcgtcc cttccagccc aggcacccca      60
cgccgtgcgt ctgcttcgcc ctcccaggtg gaggtctctg ctgtggcctc caggaatcag     120
aatgggggtt cgcagcctcg ggaatctgag gagcctcaga agtcaactga gccatccccg     180
ccttcttcga atcccccagc ttctgatgag ccgccggggt cacagctaag cgagcttgag     240
gagggaccct tgcgggtgga gggctttcac ccccagtgtc tccagcgctg caacaccccc     300
caaggctttt tgcttcacta ctgtctctta gccctaacgc aaggtattgt agtaaacggc     360
ctggtaaaca ttagcatctc caccattgag aagcgttatg aaatgaaaag ctcactgaca     420
ggcctgatat catcgagcta cgacatctcc ttttgtgtgt tatctctatt tgtgtctttc     480
tttggggaga gaggacacaa acctcgctgg ctcgcctttg catcctttat gataggcctg     540
ggagcgctgg tgttttcctt accacacttc ttcagtggaa gatatgaact gggatccatt     600
tttgaagata cgtgcttaac aaggaacagt accagatgtt catcttcaac ctccctgctt     660
tctaactact tctatgtctt tgtcctggga caattgttgc tggggaccgg agggactccg     720
ctctacaccc tggggacagc ctttattgat gactctgtgc ccacacacaa atcttctctc     780
tatataggta ttggctattc tatgtcaatc ctaggccctg ccattggata tgtgttgggt     840
ggacagctgt tgacaatgta cattgatatt gctatgggac aaagttcgga tctgactgag     900
gatgatcccc ggtggctggg ggcttggtgg attggattcc ttttagcttg gctctttgct     960
tggtctttga taatgccttt ctcctgtttt cccaagcatt taccagggac agcaaaaatt    1020
caagctggca aaacttccca gactcatcaa aataatagta cttccttcca acatacggat    1080
```

-continued

```
gaaaattttg gaaaaagtat taaagatttt ccaactgctg taaagaattt gatgaggaat    1140
acagtcttta tatgtttagt tctatcaact acttctgaag cattaattac tacgggattt    1200
gccacatttt tacctaaatt tatagaaaat caatttggat tgacatcgag ctttgcagcc    1260
actcttggag gggctgtttt aattcctgga gctgctcttg gtcaaatctt aggtggtgtt    1320
cttgtttcaa aattcaaaat gaagtgtaaa aatacaatga agtttgcctt atgtacatct    1380
ggagtagcac ttgtgctgag ttttgtattt atttatgcaa aatgtgaaaa tgagccattt    1440
gctggtgtgt ctgaatcata taatggaact ggagaaatgg ggaatttgac tgcaccttgt    1500
aatgccaact gcaactgttt gcggtcctac tattaccac tctgtggaag tgatggaatc      1560
cagtattttt ctccctgctt tgcaggttgt ttaaactcag tttcaaacag gaaacccaag    1620
gtatattata attgttcctg tatagaaagg aaaatcactt ctactgcaga aagtactgat    1680
tttgaagcta aagctggaaa atgtagaact cggtgttcaa acttgcccat atttcttggc    1740
attttcttca ttacagttat ctttaccttt atggcaggca ctcctataac tgtgtctata    1800
ttaaggtgtg ttaatcacag acatcggtct ctagcattgg gagtgcagtt catgcttctt    1860
cgattgctag gtacaatacc tgggccaatt atatttggtg tcataataga cagcacatgt    1920
gttctgtggg atgtcaatga atgtggaata aaaggagcat gttggattta tgataacatc    1980
aagatggcac atatgctggt agctataagt gttacttgta aagttatcac catattcttc    2040
aatggacttg cgattgttct ctataaacca ccgcccccag gaacagaggt atcatttcaa    2100
agtcagaatg tcattgtgtc tactatttcg gtcgaagagg atctagacaa agcagaaaat    2160
gaaggg    2166
```

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28

```
cgagcttgag gagggacctt gcggg                                          25
```

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29

```
atccaacatg ctccttttat tcc                                            23
```

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30

```
aggcgagcca gcgaggtttg tgtcc                                          25
```

<210> SEQ ID NO 31
<211> LENGTH: 25
<212> TYPE: DNA

-continued

```
<213> ORGANISM: Artificial Sequence
<220> FEATURE:
<223> OTHER INFORMATION: Primer

<400> SEQUENCE: 31
gatgcaaagg cgagccagcg aggtt                                          25

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
aactgtttgc ggtcctacta ttac                                           24

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
ggatgtcaat gaatgtggaa taaaaggag                                      29

<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34
cctttcttga ccatgcaggg ctccaa                                         26

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
agccagttcc caaagcaatc tcctc                                          25

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
atgcagggct ccaaaggaat agag                                           24

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
tcacccttca ttttctgctt tgtctag                                        27
```

```
<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
cagtaccaga tgttcatctt caacc                                              25

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
actgaggatg atccccggtg gctg                                               24

<210> SEQ ID NO 40
<211> LENGTH: 29
<212> TYPE: DNA
<213> ORGANISM: Artificial Sequence
<220> FEATURE:
<223> OTHER INFORMATION: Primer

<400> SEQUENCE: 40
tttattccac attcattgac atcccacag                                          29

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
gataactgta atgaagaaaa tgccaagaaa                                         30

<210> SEQ ID NO 42
<211> LENGTH: 29
<212> TYPE: DNA
<213> ORGANISM: Artificial Sequence
<220> FEATURE:
<223> OTHER INFORMATION: Primer

<400> SEQUENCE: 42
gcaatctcct cctccttttc acccttcat                                          29

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
cagcccaggc accccacgcc                                                    20

<210> SEQ ID NO 44
<211> LENGTH: 22
<212> TYPE: DNA
<213> ORGANISM: Artificial Sequence
<220> FEATURE:
```

```
<223> OTHER INFORMATION: Primer

<400> SEQUENCE: 44
aaggcgagcc agcgaggttt gt                                              22

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
gaagtcaact gagccatccc c                                               21

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
agctcgctta gctgtgaccc                                                 20

<210> SEQ ID NO 47
<211> LENGTH: 26
<212> TYPE: DNA
<213> ORGANISM: Artificial Sequence
<220> FEATURE:
<223> OTHER INFORMATION: Probe

<400> SEQUENCE: 47
tcttcgaatc ccccagcttc tgatga                                          26

<210> SEQ ID NO 48
<211> LENGTH: 1737
<212> TYPE: DNA
<213> ORGANISM: Mus musculus

<400> SEQUENCE: 48
cgagcttgag gagggacctt gcgggtggag gggctttcac ccccagtgtc tccagcgctg     60
caacaccccc caaggctttt tgcttcacta ctgtctctta gccctaacgc aaggtattgt    120
agtaaacggc ctggtaaaca ttagcatctc caccattgag aagcgttatg aaatgaaaag    180
ctcactgaca ggcctgatat catcgagcta cgacatctcc ttttgtgtgt tatctctatt    240
tgtgtctttc tttggggaga gaggacacaa acctcgctgg ctcgcctttg catccttat    300
gataggcctg ggagcgctgg tgttttcctt accacacttc ttcagtggaa gatatgaact    360
gggatccatt tttgaagata cgtgcttaac aaggaacagt accagatgtt catcttcaac    420
ctccctgctt tctaactact tctatgtctt tgtcctggga caattgttgc tggggaccgg    480
agggactccg ctctacaccc tggggacagc ctttattgat gactctgtgc ccacacacaa    540
atcttctctc tatataggta ttggctattc tatgtcaatc ctaggccctg ccattggata    600
tgtgttgggt ggacagctgt tgacaatgta cattgatatt gctatgggac aaagttcgga    660
tctgactgag gatgatcccc ggtggctggg ggcttggtgg attggattcc ttttagcttg    720
gctctttgct tggtctttga taatgccttt ctcctgtttt cccaagcatt taccagggac    780
agcaaaaatt caagctggca aaacttccca gactcatcaa aataatagta cttccttcca    840
acatacggat gaaaattttg gaaaaagtat taaagatttt ccaactgctg taaagaattt    900
```

```
gatgaggaat acagtcttta tatgtttagt tctatcaact acttctgaag cattaattac    960
tacgggattt gccacatttt tacctaaatt tatagaaaat caatttggat tgacatcgag   1020
ctttgcagcc actcttggag gggctgtttt aattcctgga gctgctcttg gtcaaatctt   1080
aggtggtgtt cttgtttcaa aattcaaaat gaagtgtaaa aatacaatga agtttgcctt   1140
atgtacatct ggagtagcac ttgtgctgag ttttgtattt atttatgcaa aatgtgaaaa   1200
tgagccattt gctggtgtgt ctgaatcata taatggaact ggagaaatgg ggaatttgac   1260
tgcaccttgt aatgccaact gcaactgttt gcggtcctac tattacccac tctgtggaag   1320
tgatggaatc cagtattttt ctccctgctt tgcaggttgt ttaaactcag tttcaaacag   1380
gaaacccaag gtatattata attgttcctg tatagaaagg aaaatcactt ctactgcaga   1440
aagtactgat tttgaagcta aagctggaaa atgtagaact cggtgttcaa acttgcccat   1500
atttcttggc attttcttca ttacagttat ctttaccttt atggcaggca ctcctataac   1560
tgtgtctata ttaaggtgtg ttaatcacag acatcggtct ctagcattgg gagtgcagtt   1620
catgcttctt cgattgctag gtacaatacc tgggccaatt atatttggtg tcataataga   1680
cagcacatgt gttctgtggg atgtcaatga atgtggaata aaaggagcat gttggat     1737

<210> SEQ ID NO 49
<211> LENGTH: 532
<212> TYPE: DNA
<213> ORGANISM: Mus musculus

<400> SEQUENCE: 49
gaacctttct tgaccatgca gggctccaaa ggaatagaga acccggcttt cgtcccttcc     60
agcccaggca ccccacgccg tgcgtctgct tcgccctccc aggtggaggt ctctgctgtg    120
gcctccagga atcagaatgg gggttcgcag cctcgggaat ctgaggagcc tcagaagtca    180
actgagccat ccccgccttc ttcgaatccc ccagcttctg atgagccgcc ggggtcacag    240
ctaagcgagc ttgaggaggg accttgcggg tggaggggct ttcaccccca gtgtctccag    300
cgctgcaaca ccccccaagg cttttttgct tcactactgtc tcttagccct aacgcaaggt    360
attgtagtaa acggcctggt aaacattagc atctccacca ttgagaagcg ttatgaaatg    420
aaaagctcac tgacaggcct gatatcatcg agctacgaca tctccttttg tgtgttatct    480
ctatttgtgt ctttctttgg ggagagagga cacaaacctc gctggctcgc ct             532

<210> SEQ ID NO 50
<211> LENGTH: 273
<212> TYPE: DNA
<213> ORGANISM: Mus musculus

<400> SEQUENCE: 50
ggatgtcaat gaatgtggaa taaaaggagc atgttggatt tatgataaca tcaagatggc     60
acatatgctg gtagctataa gtgttacttg taaagttatc accatattct tcaatggact    120
tgcgattgtt ctctataaac caccgccccc aggaacagag gtatcatttc aaagtcagaa    180
tgtcattgtg tctactattt cggtcgaaga ggatctagac aaagcagaaa atgaagggtg    240
aaaaggagga ggagattgct ttgggaactg gct                                  273

<210> SEQ ID NO 51
<211> LENGTH: 2169
<212> TYPE: DNA
<213> ORGANISM: Mus musculus
```

<400> SEQUENCE: 51

```
atgcagggct ccaaaggaat agagaacccg gctttcgtcc cttccagccc aggcacccca    60
cgccgtgcgt ctgcttcgcc ctcccaggtg gaggtctctg ctgtggcctc caggaatcag   120
aatgggggtt cgcagcctcg ggaatctgag gagcctcaga agtcaactga gccatccccg   180
ccttcttcga atccccccagc ttctgatgag ccgccggggt cacagctaag cgagcttgag   240
gagggacctt gcgggtggag gggctttcac ccccagtgtc tccagcgctg caacaccccc   300
caaggctttt tgcttcacta ctgtctctta gccctaacgc aaggtattgt agtaaacggc   360
ctggtaaaca ttagcatctc caccattgag aagcgttatg aaatgaaaag ctcactgaca   420
ggcctgatat catcgagcta cgacatctcc ttttgtgtgt tatctctatt tgtgtctttc   480
tttggggaga gaggacacaa acctcgctgg ctcgcctttg catcctttat gataggcctg   540
ggagcgctgg tgttttcctt accacacttc ttcagtggaa gatatgaact gggatccatt   600
tttgaagata cgtgcttaac aaggaacagt accagatgtt catcttcaac ctccctgctt   660
tctaactact tctatgtctt tgtcctggga caattgttgc tggggaccgg agggactccg   720
ctctacaccc tggggacagc ctttattgat gactctgtgc ccacacacaa atcttctctc   780
tatataggta ttggctattc tatgtcaatc ctaggccctg ccattggata tgtgttgggt   840
ggacagctgt tgacaatgta cattgatatt gctatgggac aaagttcgga tctgactgag   900
gatgatcccc ggtggctggg ggcttggtgg attggattcc ttttagcttg gctctttgct   960
tggtctttga taatgccttt ctcctgtttt cccaagcatt taccagggac agcaaaaatt  1020
caagctggca aaacttccca gactcatcaa ataatagta cttccttcca acatacggat  1080
gaaaattttg gaaaaagtat taaagatttt ccaactgctg taaagaattt gatgaggaat  1140
acagtcttta tatgtttagt tctatcaact acttctgaag cattaattac tacgggattt  1200
gccacatttt tacctaaatt tatagaaaat caatttggat tgacatcgag ctttgcagcc  1260
actcttggag gggctgtttt aattcctgga gctgctcttg gtcaaatctt aggtggtgtt  1320
cttgtttcaa aattcaaaat gaagtgtaaa aatacaatga agtttgcctt atgtacatct  1380
ggagtagcac ttgtgctgag ttttgtattt atttatgcaa aatgtgaaaa tgagccattt  1440
gctggtgtgt ctgaatcata taatggaact ggagaaatgg ggaatttgac tgcaccttgt  1500
aatgccaact gcaactgttt gcggtcctac tattacccac tctgtggaag tgatggaatc  1560
cagtatttt ctccctgctt tgcaggttgt ttaaactcag tttcaaacag gaaacccaag  1620
gtatattata attgttcctg tatagaaagg aaaatcactt ctactgcaga aagtactgat  1680
tttgaagcta aagctggaaa atgtagaact cggtgttcaa acttgcccat atttcttggc  1740
atttcttca ttacagttat cttaccttt atggcaggca ctcctataac tgtgtctata   1800
ttaaggtgtg ttaatcacag acatcggtct ctagcattgg gagtgcagtt catgcttctt  1860
cgattgctag gtacaatacc tgggccaatt atatttggtg tcataataga cagcacatgt  1920
gttctgtggg atgtcaatga atgtggaata aaaggagcat gttggattta tgataacatc  1980
aagatggcac atatgctggt agctataagt gttacttgta aagttatcac catattcttc  2040
aatggacttg cgattgttct ctataaacca ccgcccccag gaacagaggt atcatttcaa  2100
agtcagaatg tcattgtgtc tactatttcg gtcgaagagg atctagacaa agcagaaaat  2160
gaagggtga                                                          2169
```

<210> SEQ ID NO 52
<211> LENGTH: 724

```
<212> TYPE: PRT
<213> ORGANISM: Rattus norvegicus

<400> SEQUENCE: 52

Met Gln Gly Ser Lys Gly Val Glu Asn Pro Ala Phe Val Pro Ser Ser
                 5                  10                  15

Pro Asp Thr Pro Arg Ala Ser Ala Ser Pro Ser Gln Val Glu Val
             20                  25                  30

Ser Ala Val Ala Ser Arg Asn Gln Asn Gly Gly Ser Gln Pro Arg Glu
             35                  40                  45

Ser Glu Asp Pro Gln Lys Ser Thr Glu Pro Ser Pro Ser Ser Thr
 50                  55                  60

Leu Pro Ala Ser Asp Glu Pro Pro Gly Ser Gln Leu Ser Glu Leu Glu
 65                  70                  75                  80

Glu Gly Pro Cys Gly Trp Arg Asn Phe His Pro Gln Cys Leu Gln Arg
                 85                  90                  95

Cys Asn Asn Pro Lys Gly Phe Leu Leu His Tyr Cys Leu Leu Ala Leu
                100                 105                 110

Thr Gln Gly Ile Val Val Asn Gly Leu Val Asn Ile Ser Ile Ser Thr
                115                 120                 125

Ile Glu Lys Arg Tyr Glu Met Lys Ser Ser Leu Thr Gly Leu Ile Ser
 130                 135                 140

Ser Ser Tyr Asp Ile Ser Phe Cys Val Leu Ser Leu Phe Val Ser Phe
145                 150                 155                 160

Phe Gly Glu Arg Gly His Lys Pro Arg Trp Leu Ala Phe Ala Ser Phe
                165                 170                 175

Met Ile Gly Leu Gly Ala Leu Val Phe Ser Leu Pro His Phe Phe Ser
                180                 185                 190

Gly Arg Tyr Glu Leu Gly Thr Ile Phe Glu Asp Thr Cys Leu Thr Arg
                195                 200                 205

Asn Ser Thr Arg Cys Ala Ser Ser Thr Ser Leu Leu Ser Asn Tyr Phe
 210                 215                 220

Tyr Val Phe Val Leu Gly Gln Leu Leu Leu Gly Thr Gly Thr Pro
225                 230                 235                 240

Leu Tyr Thr Leu Gly Thr Ala Phe Ile Asp Asp Ser Val Pro Thr His
                245                 250                 255

Lys Ser Ser Leu Tyr Ile Gly Ile Gly Tyr Ser Met Ser Ile Leu Gly
                260                 265                 270

Pro Ala Ile Gly Tyr Val Leu Gly Gly Gln Leu Leu Thr Met Tyr Ile
                275                 280                 285

Asp Val Ala Met Gly Gln Ser Ser Asp Leu Thr Glu Asp Asp Pro Arg
 290                 295                 300

Trp Leu Gly Ala Trp Trp Ile Gly Phe Leu Leu Ala Trp Leu Phe Ala
305                 310                 315                 320

Trp Ser Leu Ile Met Pro Phe Ser Cys Phe Pro Lys His Leu Pro Gly
                325                 330                 335

Thr Ala Lys Ile Gln Ala Gly Lys Thr Ser Gln Thr His Gln Asn Asn
                340                 345                 350

Ser Thr Ser Phe Gln His Met Asp Glu Asn Phe Gly Lys Ser Ile Lys
                355                 360                 365

Asp Phe Pro Thr Ala Val Lys Asn Leu Met Arg Asn Thr Val Phe Ile
                370                 375                 380

Cys Leu Val Leu Ser Thr Thr Ser Glu Ala Leu Val Thr Thr Gly Phe
385                 390                 395                 400
```

-continued

```
Ala Thr Phe Leu Pro Lys Phe Ile Glu Asn Gln Phe Gly Leu Thr Ser
            405                 410                 415
Ser Ile Ala Ala Thr Leu Gly Gly Ala Val Leu Ile Pro Gly Ala Ala
        420                 425                 430
Leu Gly Gln Ile Leu Gly Gly Val Leu Val Ser Lys Phe Lys Met Lys
    435                 440                 445
Cys Lys Asn Thr Met Lys Phe Ala Leu Cys Thr Ser Gly Val Ala Leu
    450                 455                 460
Met Leu Ser Phe Val Phe Ile Tyr Ala Lys Cys Glu Asn Gly Pro Phe
465                 470                 475                 480
Ala Gly Val Ser Glu Ser Tyr Asn Gly Thr Gly Glu Met Gly Asn Leu
            485                 490                 495
Thr Ala Pro Cys Asn Ala Asn Cys Asn Cys Leu Arg Ser Tyr Tyr Tyr
        500                 505                 510
Pro Leu Cys Gly Ser Asp Gly Val Gln Tyr Phe Ser Pro Cys Phe Ala
    515                 520                 525
Gly Cys Leu Asn Ser Val Ser Asn Arg Lys Pro Lys Ala Tyr Tyr Asn
    530                 535                 540
Cys Ser Cys Ile Glu Arg Lys Val Asp Ile Thr Ser Thr Ala Glu Ser
545                 550                 555                 560
Pro Asp Phe Glu Ala Arg Ala Gly Lys Cys Lys Thr Gln Cys Ser Asn
            565                 570                 575
Leu Pro Ile Phe Leu Gly Ile Phe Phe Ile Thr Val Ile Phe Thr Phe
        580                 585                 590
Met Ala Gly Thr Pro Ile Thr Val Ser Ile Leu Arg Cys Val Asn His
    595                 600                 605
Arg Gln Arg Ser Leu Ala Leu Gly Val Gln Phe Met Leu Leu Arg Leu
    610                 615                 620
Leu Gly Thr Ile Pro Gly Pro Ile Ile Phe Gly Val Thr Ile Asp Ser
625                 630                 635                 640
Thr Cys Val Leu Trp Asp Ile Asn Glu Cys Gly Thr Lys Gly Ala Cys
            645                 650                 655
Trp Ile Tyr Asp Asn Ile Arg Met Ala His Met Leu Val Ala Ile Ser
        660                 665                 670
Val Thr Cys Lys Val Ile Thr Ile Phe Phe Asn Gly Leu Ala Ile Val
    675                 680                 685
Leu Tyr Lys Pro Pro Pro Gly Thr Glu Val Ser Phe Gln Ser Gln
    690                 695                 700
Asn Val Val Val Ser Thr Ile Thr Val Glu Glu Asp Leu Asn Lys Ile
705                 710                 715                 720
Glu Asn Glu Gly

<210> SEQ ID NO 53
<211> LENGTH: 2172
<212> TYPE: DNA
<213> ORGANISM: Rattus norvegicus

<400> SEQUENCE: 53
atgcagggtt ccaagggagt cgagaacccg gcattcgtcc cttccagccc agacacccca      60
cgccgtgcgt ctgcgtcgcc ttcccaggtg gaggtctctg ctgtggcctc caggaatcag     120
aatgggggtt cgcaacctcg ggaatctgaa gatcccagaa gtcaactga gccatctcct      180 ccttcttcga ctctcccagc ttctgatgag ccgccggggt cacagctaag cgagcttgag     240
```

```
gagggacctt gcgggtggag gaacttccac ccccagtgtc ttcagcgctg caacaacccc      300
aaaggttttc tgcttcacta ctgtctctta gccctaacgc aaggtattgt agtaaatggc      360
ctagtaaata ttagcatttc caccatcgag aagcgctatg aaatgaagag ttccctgacc      420
ggcctgatat catcgagcta cgacatctcc ttttgcgtgt tgtctctgtt tgtgtctttc      480
tttggtgaga gaggacacaa acctcgctgg cttgcctttg catcctttat gatcggactg      540
ggagcgctgg tgttttcttt accacacttc ttcagtggga gatatgaact gggaaccatt      600
ttcgaagata cctgcttaac aaggaacagc accagatgtg cttcttcaac ctctctgctt      660
tctaactact tctatgtctt tgtcctggga caactgttgc tggggactgg aggaactccg      720
ctctacaccc tgggaacggc cttcattgat gactctgtac ccacacacaa atcttctcta      780
tatatcggta ttggctattc tatgtcaatc ctaggcccag ccattggcta tgtgttggga      840
ggacagctgt tgacaatgta cattgatgtt gctatggac aaagttcaga tctgactgag       900
gatgatcccc ggtggttggg ggcttggtgg attggattcc ttttagcttg gctctttgct      960
tggtctttga taatgccttt ctcctgtttt ccaaagcatt taccagggac agcaaaaatt     1020
caagctggca aaacttccca gactcatcaa aataatagta cttccttcca acatatggat     1080
gaaaattttg ggaaaagtat taagatttt ccaactgctg tgaagaattt gatgaggaat      1140
acagtcttta tatgtttagt tctatcaact acttctgaag cactagttac cacgggatt      1200 gccacgtttt tacctaaatt tatagaaaat caatttggat tgacatcgag cattgcggca     1260
acacttggag gggctgtttt aattcctgga gctgctcttg gtcaaatctt aggtggtgtt     1320
cttgtttcaa aattcaaaat gaagtgtaaa atacaatga gtttgcgtt atgtacatct       1380 ggagtagcac ttatgctgag ttttgtattt atttatgcaa aatgtgaaaa tgggccattt     1440
gctggtgtgt ctgaatcata taatggaaca ggagagatgg ggaatctgac tgcaccttgc     1500
aatgccaatt gcaattgttt gagatcctat tattacccac tctgtggaag tgatggagtc     1560 cagtatttt ctccctgctt tgcaggttgt ttaaactcag tttcaaacag gaaaccaaag      1620
gcatattata attgttcctg tattgaaagg aaagtcgaca tcacttctac tgcagaaagc     1680
cctgattttg aagcaagggc tggaaaatgt aaaactcagt gttcaaacct gcccatattt     1740
ctcggcatct tcttcatcac tgtgattttt acctttatgg caggtacccc cataactgtg     1800
tccatattaa ggtgtgtcaa tcacagacag cgatctctag cactgggagt gcagttcatg     1860
cttcttcggt tgttaggcac gatacctggg ccaattatat ttggcgtcac aatagacagc     1920
acgtgtgttc tgtgggacat caatgaatgt ggaacaaagg gggcgtgttg gatctatgat     1980
aacatcagga tggcgcatat gctggtggct ataagtgtta cttgtaaagt catcaccata     2040
ttcttcaatg gacttgcgat agttctctat aaaccaccgc ccccaggaac ggaggtatca     2100
tttcaaagtc agaatgtagt tgtgtcgacg attacagtgg aggaggacct caacaaaata     2160
gagaacgaag ga                                                         2172

<210> SEQ ID NO 54
<211> LENGTH: 724
<212> TYPE: PRT
<213> ORGANISM: Rattus norvegicus

<400> SEQUENCE: 54

Met Gln Gly Ser Lys Gly Val Glu Asn Pro Ala Phe Val Pro Ser Ser
              5                   10                  15

Pro Asp Thr Pro Arg Arg Ala Ser Ala Ser Pro Ser Gln Val Glu Val
         20                  25                  30
```

```
Ser Ala Val Ala Ser Arg Asn Gln Asn Gly Gly Ser Gln Pro Arg Asp
            35                  40                  45

Ser Glu Asp Pro Gln Lys Ser Thr Glu Pro Ser Pro Pro Ser Ser Thr
        50                  55                  60

Leu Pro Ala Ser Asp Glu Pro Pro Gly Ser Gln Leu Arg Glu Leu Glu
 65                 70                  75                  80

Glu Gly Pro Cys Gly Trp Arg Asn Phe His Pro Gln Cys Leu Gln Arg
                85                  90                  95

Cys Asn Asn Pro Lys Gly Phe Leu Leu His Tyr Cys Leu Leu Ala Leu
            100                 105                 110

Thr Gln Gly Ile Val Val Asn Gly Leu Val Asn Ile Ser Ile Ser Thr
            115                 120                 125

Ile Glu Lys Arg Tyr Glu Met Lys Ser Ser Leu Thr Gly Leu Ile Ser
            130                 135                 140

Ser Ser Tyr Asp Ile Ser Phe Cys Val Leu Ser Leu Phe Val Ser Phe
145                 150                 155                 160

Phe Gly Glu Arg Gly His Lys Pro Arg Trp Leu Ala Phe Ala Ser Phe
                165                 170                 175

Met Ile Gly Leu Gly Ala Leu Val Phe Ser Leu Pro His Phe Phe Ser
            180                 185                 190

Gly Arg Tyr Glu Leu Gly Thr Ile Phe Glu Asp Thr Cys Leu Thr Arg
            195                 200                 205

Asn Ser Thr Arg Cys Ala Ser Ser Thr Ser Leu Leu Ser Asn Tyr Phe
            210                 215                 220

Tyr Val Phe Val Leu Gly Gln Leu Leu Leu Gly Thr Gly Gly Thr Pro
225                 230                 235                 240

Leu Tyr Thr Leu Gly Thr Ala Phe Ile Asp Asp Ser Val Pro Thr His
                245                 250                 255

Lys Ser Ser Leu Tyr Ile Gly Ile Gly Tyr Ser Met Ser Ile Leu Gly
            260                 265                 270

Pro Ala Ile Gly Tyr Val Leu Gly Gly Gln Leu Leu Thr Met Tyr Ile
            275                 280                 285

Asp Val Ala Met Gly Gln Ser Ser Asp Leu Thr Glu Asp Asp Pro Arg
            290                 295                 300

Trp Leu Gly Ala Trp Trp Ile Gly Phe Leu Leu Ala Trp Leu Phe Ala
305                 310                 315                 320

Trp Ser Leu Ile Met Pro Phe Ser Cys Phe Pro Lys His Leu Pro Gly
                325                 330                 335

Thr Ala Lys Ile Gln Ala Gly Lys Thr Ser Gln Thr His Gln Asn Asn
            340                 345                 350

Ser Thr Ser Phe Gln His Met Asp Glu Asn Phe Gly Lys Ser Ile Lys
            355                 360                 365

Asp Phe Pro Thr Ala Val Lys Asn Leu Met Arg Asn Thr Val Phe Ile
            370                 375                 380

Cys Leu Val Leu Ser Thr Thr Ser Glu Ala Leu Val Thr Thr Gly Phe
385                 390                 395                 400

Ala Thr Phe Leu Pro Lys Phe Ile Glu Asn Gln Phe Gly Leu Thr Ser
                405                 410                 415

Ser Phe Ala Ala Thr Leu Gly Gly Ala Val Leu Ile Pro Gly Ala Ala
            420                 425                 430

Leu Gly Gln Ile Leu Gly Gly Val Leu Val Ser Lys Phe Lys Met Lys
            435                 440                 445
```

-continued

Cys Lys Asn Thr Met Lys Phe Ala Leu Cys Thr Ser Gly Val Ala Leu
            450                 455                 460

Met Leu Ser Phe Val Phe Ile Tyr Ala Lys Cys Glu Asn Gly Pro Phe
465                 470                 475                 480

Ala Gly Val Ser Glu Ser Tyr Asn Gly Thr Gly Glu Met Gly Asn Leu
                485                 490                 495

Thr Ala Pro Cys Asn Ala Asn Cys Asn Cys Leu Arg Ser Tyr Tyr Tyr
            500                 505                 510

Pro Leu Cys Gly Ser Asp Gly Val Gln Tyr Phe Ser Pro Cys Phe Ala
            515                 520                 525

Gly Cys Leu Asn Ser Val Ser Asn Arg Lys Pro Lys Ala Tyr Tyr Asn
            530                 535                 540

Cys Ser Cys Ile Glu Arg Lys Val Asp Ile Thr Ser Thr Ala Glu Ser
545                 550                 555                 560

Pro Asp Phe Glu Ala Arg Ala Gly Lys Cys Lys Thr Gln Cys Ser Asn
                565                 570                 575

Leu Pro Ile Phe Leu Gly Ile Phe Ile Thr Val Ile Phe Thr Phe
            580                 585                 590

Met Ala Gly Thr Pro Ile Thr Val Ser Ile Leu Arg Cys Val Asn His
            595                 600                 605

Arg Gln Arg Ser Leu Ala Leu Gly Val Gln Phe Met Leu Leu Arg Leu
            610                 615                 620

Leu Gly Thr Ile Pro Gly Pro Ile Ile Phe Gly Val Thr Ile Asp Ser
625                 630                 635                 640

Thr Cys Val Leu Trp Asp Ile Asn Glu Cys Gly Thr Lys Gly Ala Cys
                645                 650                 655

Trp Ile Tyr Asp Asn Ile Arg Met Ala His Met Leu Val Ala Ile Ser
            660                 665                 670

Val Thr Cys Lys Val Ile Thr Ile Phe Phe Asn Gly Leu Ala Ile Val
            675                 680                 685

Leu Tyr Lys Pro Pro Pro Gly Thr Glu Val Ser Phe Gln Ser Gln
            690                 695                 700

Asn Val Val Val Ser Thr Ile Thr Val Glu Glu Asp Leu Asn Lys Ile
705                 710                 715                 720

Glu Asn Glu Gly

<210> SEQ ID NO 55
<211> LENGTH: 2172
<212> TYPE: DNA
<213> ORGANISM: Rattus norvegicus

<400> SEQUENCE: 55
atgcagggtt ccaagggagt cgagaacccg gcattcgtcc cttccagccc agacacccca      60
cgccgtgcgt ctgcgtcgcc ttcccaggtg gaggtctctg ctgtggcctc caggaatcag     120
aatgggggtt cgcaacctcg ggattctgaa gatccccaga gtcaactga gccatctcct     180 ccttcttcga ctctcccagc ttctgatgag ccgccggggt cacagctaag agagcttgag     240
gagggacctt gcgggtggag gaacttccac ccccagtgtc ttcagcgctg caacaacccc     300
aaaggttttc tgcttcacta ctgtctctta gccctaacgc aaggtattgt agtaaatggc     360
ctagtaaata ttagcatttc caccatcgag aagcgctatg aaatgaagag ttccctgacc     420
ggcctgatat catcgagcta cgacatctcc tttgcgtgt gtctctgtt tgtgtctttc      480 tttggtgaga gaggacacaa acctcgctgg cttgcctttg catcctttat gatcggactg     540

```
ggagcgctgg tgttttcttt accacacttc ttcagtggga gatatgaact gggaaccatt    600
ttcgaagata cctgcttaac aaggaacagc accagatgtg cttcttcaac ctctctgctt    660
tctaactact tctatgtctt tgtcctggga caactgttgc tggggactgg aggaactccg    720
ctctacaccc tgggaacggc cttcattgat gactctgtac ccacacacaa atcttctcta    780
tatatcggta ttggctattc tatgtcaatc ctaggcccag ccattggcta tgtgttggga    840
ggacagctgt tgacaatgta cattgatgtt gctatggaca aaagttcaga tctgactgag    900
gatgatcccc ggtggttggg ggcttggtgg attggattcc ttttagcttg gctctttgct    960
tggtctttga taatgccttt ctcctgtttt ccaaagcatt taccagggac agcaaaaatt   1020
caagctggca aaacttccca gactcatcaa aataatagta cttccttcca acatatggat   1080
gaaaattttg ggaaaagtat taagattttt ccaactgctg tgaagaattt gatgaggaat   1140
acagtcttta tatgtttagt tctatcaact acttctgaag cactagttac cacgggattt   1200
gccacgtttt tacctaaatt tatagaaaat caatttggat tgacatcgag ctttgcggca   1260
acacttggag gggctgtttt aattcctgga gctgctcttg gtcaaatctt aggtggtgtt   1320 cttgttttcaa aattcaaaat gaagtgtaaa aatacaatga agtttgcgtt atgtacatct   1380
ggagtagcac ttatgctgag ttttgtattt atttatgcaa aatgtgaaaa tgggccattt   1440
gctggtgtgt ctgaatcata taatggaaca ggagagatgg ggaatctgac tgcaccttgc   1500
aatgccaatt gcaattgttt gagatcctat tattacccgc tctgtggaag tgatggagtc   1560
cagtattttt ctccctgctt tgcaggttgt ttaaactcag tttcaaacag gaaaccaaag   1620
gcatattata attgttcctg tattgaaagg aaagtcgaca tcacttctac tgcagaaagc   1680
cctgattttg aagcaagggc tggaaaatgt aaaactcagt gttcaaacct gcccatattt   1740
ctcggcatct tcttcatcac tgtgattttt acctttatgg caggtacccc cataactgtg   1800
tccatattaa ggtgtgtcaa tcacagacag cgatctctag cactgggagt gcagttcatg   1860
cttcttcggt tgttaggcac gatacctggg ccaattatat ttggcgtcac aatagacagc   1920
acgtgtgttc tgtgggacat caatgaatgt ggaacaaagg gggcgtgttg gatctatgat   1980
aacatcagga tggcgcatat gctggtggct ataagtgtta cttgtaaagt catcaccata   2040
ttcttcaatg gacttgcgat agttctctat aaaccaccgc ccccaggaac ggaggtatca   2100
tttcaaagtc agaatgtagt tgtgtcgacg attacagtgg aggaggacct caacaaaata   2160
gagaacgaag ga                                                      2172
```

<210> SEQ ID NO 56
<211> LENGTH: 25
<212> TYPE: DNA
<213> ORGANISM: Artificial Sequence
<220> FEATURE:
<223> OTHER INFORMATION: Primer

<400> SEQUENCE: 56
tcaactgagc catccccgcc ttctt                                          25

<210> SEQ ID NO 57
<211> LENGTH: 25
<212> TYPE: DNA
<213> ORGANISM: Artificial Sequence
<220> FEATURE:
<223> OTHER INFORMATION: Primer

<400> SEQUENCE: 57
tctgttcctg ggggcggtgg tttat                                          25

-continued

```
<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58
gacacaaaca gagacaacac gcaaaaggag                                    30

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
acaaacagag acaacacgca aaaggagatg                                    30

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
atcggactgg gagcgctggt gtttt                                         25

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61
tattattacc cactctgtgg aagtgatgga                                    30

<210> SEQ ID NO 62
<211> LENGTH: 26
<212> TYPE: DNA
<213> ORGANISM: Artificial Sequence
<220> FEATURE:
<223> OTHER INFORMATION: Primer

<400> SEQUENCE: 62
ctttcttgac catgcagggt tccaag                                        26

<210> SEQ ID NO 63
<211> LENGTH: 26
<212> TYPE: DNA
<213> ORGANISM: Artificial Sequence
<220> FEATURE:
<223> OTHER INFORMATION: Primer

<400> SEQUENCE: 63
atcctcttct ttctcatcct tcgttc                                        26

<210> SEQ ID NO 64
<211> LENGTH: 27
<212> TYPE: DNA
<213> ORGANISM: Artificial Sequence
<220> FEATURE:
```

```
<223> OTHER INFORMATION: Primer

<400> SEQUENCE: 64
atgcagggtt ccaagggagt cgagaac                                         27

<210> SEQ ID NO 65
<211> LENGTH: 28
<212> TYPE: DNA
<213> ORGANISM: Artificial Sequence
<220> FEATURE:
<223> OTHER INFORMATION: Primer

<400> SEQUENCE: 65
tcatccttcg ttctctattt tgttgagg                                        28

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
taatacgact cactataggg                                                 20

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
catacgattt aggtgacact atag                                            24

<210> SEQ ID NO 68
<211> LENGTH: 25
<212> TYPE: DNA
<213> ORGANISM: Artificial Sequence
<220> FEATURE:
<223> OTHER INFORMATION: Primer

<400> SEQUENCE: 68
atcgagaagc gctatgaaat gaaga                                           25

<210> SEQ ID NO 69
<211> LENGTH: 18
<212> TYPE: DNA
<213> ORGANISM: Artificial Sequence
<220> FEATURE:
<223> OTHER INFORMATION: Primer

<400> SEQUENCE: 69
agcgctccca gtccgatc                                                   18

<210> SEQ ID NO 70
<211> LENGTH: 23
<212> TYPE: DNA
<213> ORGANISM: Artificial Sequence
<220> FEATURE:
<223> OTHER INFORMATION: Primer

<400> SEQUENCE: 70
tttggtgaga gaggacacaa acc                                             23
```

```
<210> SEQ ID NO 71
<211> LENGTH: 28
<212> TYPE: DNA
<213> ORGANISM: Artificial Sequence
<220> FEATURE:
<223> OTHER INFORMATION: Primer

<400> SEQUENCE: 71
ggactgggag cgctggtgtt ttctttac                                          28

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
cccagggtgt agagcggagt t                                                 21

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
tggtctttga taatgccttt ctcct                                             25

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74
ctgctgtgaa gaatttgatg aggaa                                             25

<210> SEQ ID NO 75
<211> LENGTH: 25
<212> TYPE: DNA
<213> ORGANISM: Artificial Sequence
<220> FEATURE:
<223> OTHER INFORMATION: Primer

<400> SEQUENCE: 75
cagtgatgaa gaagatgccg agaaa                                             25

<210> SEQ ID NO 76
<211> LENGTH: 25
<212> TYPE: DNA
<213> ORGANISM: Artificial Sequence
<220> FEATURE:
<223> OTHER INFORMATION: Probe

<400> SEQUENCE: 76
cgctggcttg cctttgcatc cttta                                             25

<210> SEQ ID NO 77
<211> LENGTH: 1931
<212> TYPE: DNA
<213> ORGANISM: Rattus norvegicus

<400> SEQUENCE: 77
```

```
tcaactgagc catctcctcc ttcttcgact ctcccagctt ctgatgagcc gccggggtca      60
cagctaagcg agcttgagga gggaccttgc gggtggagga acttccaccc ccagtgtctt     120
cagcgctgca acaacccaa aggttttctg cttcactact gtctcttagc cctaacgcaa     180
ggtattgtag taaatggcct agtaaatatt agcatttcca ccatcgagaa gcgctatgaa     240
atgaagagtt ccctgaccgg cctgatatca tcgagctacg acatctcctt ttgcgtgttg     300
tctctgtttg tgtctttctt tggtgagaga ggacacaaac ctcgctggct tgcctttgca     360
tcctttatga tcggactggg agcgctggtg ttttctttac cacacttctt cagtgggaga     420
tatgaactgg gaaccatttt cgaagatacc tgcttaacaa ggaacagcac cagatgtgct     480
tcttcaacct ctctgctttc taactacttc tatgtctttg tcctgggaca actgttgctg     540
gggactggag gaactccgct ctacaccctg gaacggcct tcattgatga ctctgtaccc     600
acacacaaat cttctctata tatcggtatt ggctattcta tgtcaatcct aggcccagcc     660
attggctatg tgttgggagg acagctgttg acaatgtaca ttgatgttgc tatgggacaa     720
agttcagatc tgactgagga tgatcccgg tggttggggg cttggtggat tggattcctt     780
ttagcttggc tctttgcttg gtctttgata atgccttctt cctgttttcc aaagcattta     840
ccagggacag caaaaattca agctggcaaa acttcccaga ctcatcaaaa taatagtact     900
tccttccaac atatggatga aaattttggg aaaagtatta agattttcc aactgctgtg     960 aagaatttga tgaggaatac agtctttata tgtttagttc tatcaactac ttctgaagca    1020
ctagttacca cggatttgc cacgttttta cctaaattta tagaaaatca atttggattg    1080
acatcgagca ttgcggcaac acttggaggg gctgttttaa ttcctggagc tgctcttggt    1140
caaatcttag gtggtgttct tgtttcaaaa ttcaaaatga agtgtaaaaa tacaatgaag    1200
tttgcgttat gtacatctgg agtagcactt atgctgagtt ttgtatttat ttatgcaaaa    1260
tgtgaaaatg ggccatttgc tggtgtgtct gaatcatata atggaacagg agagatgggg    1320
aatctgactg caccttgcaa tgccaattgc aattgtttga gatcctatta ttacccactc    1380
tgtggaagtg atggagtcca gtattttct ccctgctttg caggttgttt aaactcagtt    1440
tcaaacagga aaccaaaggc atattataat tgttcctgta ttgaaaggaa agtcgacatc    1500
acttctactg cagaaagccc tgattttgaa gcaagggctg gaaaatgtaa aactcagtgt    1560
tcaaacctgc ccatatttct cggcatcttc ttcatcactg tgatttttac ctttatggca    1620
ggtaccccca taactgtgtc catattaagg tgtgtcaatc acagacagcg atctctagca    1680
ctgggagtgc agttcatgct tcttcggttg ttaggcacga tacctgggcc aattatattt    1740
ggcgtcacaa tagacagcac gtgtgttctg tgggacatca atgaatgtgg aacaaagggg    1800
gcgtgttgga tctatgataa catcaggatg gcgcatatgc tggtggctat aagtgttact    1860
tgtaaagtca tcaccatatt cttcaatgga cttgcgatag ttctctataa accaccgccc    1920
ccaggaacgg a                                                         1931
```

<210> SEQ ID NO 78
<211> LENGTH: 484
<212> TYPE: DNA
<213> ORGANISM: Rattus norvegicus

<400> SEQUENCE: 78

```
ctttcttgac catgcagggt tccaaggag tcgagaaccc ggcattcgtc ccttccagcc      60
cagacacccc acgccgtgcg tctgcgtcgc cttcccaggt ggaggtctct gctgtggcct    120
ccaggaatca gaatgggggt tcgcaacctc gggaatctga agatccccag aagtcaactg    180
```

```
agccatctcc tccttcttcg actctcccag cttctgatga gccgccgggg tcacagctaa      240
gcgagcttga ggagggacct tgcgggtgga ggaacttcca cccccagtgt cttcagcgct      300
gcaacaaccc caaggttttt ctgcttcact actgtctctt agccctaacg caaggtattg      360
tagtaaatgg cctagtaaat attagcattt ccaccatcga aagcgctat gaaatgaaga       420 gttccctgac cggcctgata tcatcgagct acgacatctc cttttgcgtg ttgtctctgt      480
ttgt                                                                   484

<210> SEQ ID NO 79
<211> LENGTH: 704
<212> TYPE: DNA
<213> ORGANISM: Rattus norvegicus

<400> SEQUENCE: 79
tattattacc cactctgtgg aagtgatgga gtccagtatt tttctccctg ctttgcaggt       60
tgtttaaact cagtttcaaa caggaaacca aaggcatatt ataattgttc ctgtattgaa      120
aggaaagtcg acatcacttc tactgcagaa agccctgatt tgaagcaag gctggaaaa       180 tgtaaaactc agtgttcaaa cctgcccata tttctcggca tcttcttcat cactgtgatt      240 tttacctta tggcaggtac ccccataact gtgtccatat taaggtgtgt caatcacaga       300
cagcgatctc tagcactggg agtgcagttc atgcttcttc ggttgttagg cacgatacct      360
gggccaatta tatttggcgt cacaatagac agcacgtgtg ttctgtggga catcaatgaa      420
tgtggaacaa aggggggcgtg ttggatctat gataacatca ggatgcgca tatgctggtg      480 gctataagtg ttacttgtaa agtcatcacc atattcttca atggacttgc gatagttctc      540
tataaaccac cgcccccagg aacgaggta tcatttcaaa gtcagaatgt agttgtgtcg       600
acgattacag tggaggagga cctcaacaaa atagagaacg aaggatgaga agaagagga      660 tactgcttta gaaaagtggc tccttcctgt cagaacaaac tgtg                       704

<210> SEQ ID NO 80
<211> LENGTH: 2175
<212> TYPE: DNA
<213> ORGANISM: Rattus norvegicus

<400> SEQUENCE: 80
atgcagggtt ccaagggagt cgagaacccg gcattcgtcc cttccagccc agacacccca       60
cgccgtgcgt ctgcgtcgcc ttcccaggtg gaggtctctg ctgtggcctc caggaatcag      120
aatgggggtt cgcaaccctcg ggaatctgaa gatccccaga agtcaactga gccatctcct    180
ccttcttcga ctctcccagc ttctgatgag ccgccgggt cacagctaag cgagcttgag      240
gagggacctt gcgggtggag gaacttccac ccccagtgtc ttcagcgctg caacaacccc    300 aaaggtttc tgcttcacta ctgtctctta gccctaacgc aaggtattgt agtaaatggc     360
ctagtaaata ttagcatttc caccatcgag aagcgctatg aaatgaagag ttccctgacc     420
ggcctgatat catcgagcta cgacatctcc ttttgcgtgt tgtctctgtt tgtgtctttc      480
tttggtgaga gaggacacaa acctcgctgg cttgcctttg catcctttat gatcggactg    540
ggagcgctgg tgttttcttt accacacttc ttcagtggga gatatgaact gggaaccatt     600
ttcgaagata cctgcttaac aaggaacagc accagatgtg cttcttcaac ctctctgctt     660
tctaactact tctatgtctt tgtcctggga caactgttgc tggggactgg aggaactccg    720
ctctacaccc tgggaacggc cttcattgat gactctgtac ccacacacaa atcttctcta    780
```

```
tatatcggta ttggctattc tatgtcaatc ctaggcccag ccattggcta tgtgttggga      840
ggacagctgt tgacaatgta cattgatgtt gctatgggac aaagttcaga tctgactgag      900
gatgatcccc ggtggttggg ggcttggtgg attggattcc ttttagcttg gctctttgct      960
tggtctttga taatgccttt ctcctgtttt ccaaagcatt taccagggac agcaaaaatt     1020
caagctggca aaacttccca gactcatcaa aataatagta cttccttcca acatatggat     1080
gaaaattttg ggaaaagtat taaagatttt ccaactgctg tgaagaattt gatgaggaat     1140
acagtcttta tatgtttagt tctatcaact acttctgaag cactagttac cacgggattt     1200
gccacgtttt tacctaaatt tatagaaaat caatttggat tgacatcgag cattgcggca     1260
acacttggag gggctgtttt aattcctgga gctgctcttg gtcaaatctt aggtggtgtt     1320
cttgtttcaa aattcaaaat gaagtgtaaa aatacaatga agtttgcgtt atgtacatct     1380
ggagtagcac ttatgctgag ttttgtattt atttatgcaa aatgtgaaaa tgggccattt     1440
gctggtgtgt ctgaatcata taatggaaca ggagagatgg ggaatctgac tgcaccttgc     1500
aatgccaatt gcaattgttt gagatcctat tattacccac tctgtggaag tgatggagtc     1560
cagtattttt ctccctgctt tgcaggttgt ttaaactcag tttcaaacag gaaaccaaag     1620
gcatattata attgttcctg tattgaaagg aaagtcgaca tcacttctac tgcagaaagc     1680
cctgattttg aagcaagggc tggaaaatgt aaaactcagt gttcaaacct gcccatattt     1740
ctcggcatct tcttcatcac tgtgattttt accttttatgg caggtacccc cataactgtg     1800
tccatattaa ggtgtgtcaa tcacagacag cgatctctag cactgggagt gcagttcatg     1860
cttcttcggt tgttaggcac gatacctggg ccaattatat ttggcgtcac aatagacagc     1920
acgtgtgttc tgtgggacat caatgaatgt ggaacaaagg gggcgtgttg gatctatgat     1980
aacatcagga tggcgcatat gctggtggct ataagtgtta cttgtaaagt catcaccata     2040
ttcttcaatg gacttgcgat agttctctat aaaccaccgc ccccaggaac ggaggtatca     2100
tttcaaagtc agaatgtagt tgtgtcgacg attacagtgg aggaggacct caacaaaata     2160
gagaacgaag gatga                                                     2175
```

<210> SEQ ID NO 81
<211> LENGTH: 2175
<212> TYPE: DNA
<213> ORGANISM: Rattus norvegicus

<400> SEQUENCE: 81

```
atgcagggtt ccaagggagt cgagaacccg gcattcgtcc cttccagccc agacacccca       60
cgccgtgcgt ctgcgtcgcc ttcccaggtg gaggtctctg ctgtggcctc caggaatcag      120
aatgggggtt cgcaacctcg ggattctgaa gatccccaga agtcaactga gccatctcct      180
ccttcttcga ctctcccagc ttctgatgag ccgccggggt cacagctaag agagcttgag      240
gagggacctt gcgggtggag gaacttccac ccccagtgtc ttcagcgctg caacaacccc      300
aaaggttttc tgcttcacta ctgtctctta gccctaacgc aaggtattgt agtaaatggc      360
ctagtaaata ttagcatttc caccatcgag aagcgctatg aaatgaagag ttccctgacc      420
ggcctgatat catcgagcta cgacatctcc ttttgcgtgt tgtctctgtt tgtgtctttc      480
tttggtgaga gaggacacaa acctcgctgg cttgcctttg catcctttat gatcggactg      540
ggagcgctgg tgttttcttt accacacttc ttcagtggga gatatgaact gggaaccatt      600
ttcgaagata cctgcttaac aaggaacagc accagatgtg cttcttcaac ctctctgctt      660
tctaactact tctatgtctt tgtcctggga caactgttgc tggggactgg aggaactccg      720
```

```
ctctacaccc tgggaacggc cttcattgat gactctgtac ccacacacaa atcttctcta      780
tatatcggta ttggctattc tatgtcaatc ctaggcccag ccattggcta tgtgttggga      840
ggacagctgt tgacaatgta cattgatgtt gctatgggac aaagttcaga tctgactgag      900
gatgatcccc ggtggttggg ggcttggtgg attggattcc ttttagcttg gctctttgct      960
tggtctttga taatgccttt ctcctgtttt ccaaagcatt taccagggac agcaaaaatt     1020
caagctggca aaacttccca gactcatcaa ataatagta cttccttcca acatatggat      1080
gaaaattttg ggaaaagtat taaagatttt ccaactgctg tgaagaattt gatgaggaat     1140
acagtcttta tatgtttagt tctatcaact acttctgaag cactagttac cacgggattt     1200
gccacgtttt tacctaaatt tatagaaaat caatttggat tgacatcgag ctttgcggca     1260
acacttggag gggctgtttt aattcctgga gctgctcttg gtcaaatctt aggtggtgtt     1320
cttgtttcaa aattcaaaat gaagtgtaaa aatacaatga agtttgcgtt atgtacatct     1380
ggagtagcac ttatgctgag ttttgtattt atttatgcaa aatgtgaaaa tgggccattt     1440
gctggtgtgt ctgaatcata taatggaaca ggagagatgg ggaatctgac tgcaccttgc     1500
aatgccaatt gcaattgttt gagatcctat tattacccgc tctgtggaag tgatggagtc     1560
cagtattttt ctccctgctt tgcaggttgt ttaaactcag tttcaaacag gaaaccaaag     1620
gcatattata attgttcctg tattgaaagg aaagtcgaca tcacttctac tgcagaaagc     1680
cctgattttg aagcaagggc tggaaaatgt aaaactcagt gttcaaacct gcccatattt     1740
ctcggcatct tcttcatcac tgtgattttt acctttatgg caggtacccc cataactgtg     1800
tccatattaa ggtgtgtcaa tcacagacag cgatctctag cactgggagt gcagttcatg     1860
cttcttcggt tgttaggcac gatacctggg ccaattatat ttggcgtcac aatagacagc     1920
acgtgtgttc tgtgggacat caatgaatgt ggaacaaagg gggcgtgttg gatctatgat     1980
aacatcagga tggcgcatat gctggtggct ataagtgtta cttgtaaagt catcaccata     2040
ttcttcaatg gacttgcgat agttctctat aaaccaccgc ccccaggaac ggaggtatca     2100
tttcaaagtc agaatgtagt tgtgtcgacg attacagtgg aggaggacct caacaaaata     2160
gagaacgaag gatga                                                      2175
```

<210> SEQ ID NO 82
<211> LENGTH: 30
<212> TYPE: DNA
<213> ORGANISM: Artificial Sequence
<220> FEATURE:
<223> OTHER INFORMATION: Primer

<400> SEQUENCE: 82
atcgatatga agagcgccaa aggtattgag                                         30

<210> SEQ ID NO 83
<211> LENGTH: 30
<212> TYPE: DNA
<213> ORGANISM: Artificial Sequence
<220> FEATURE:
<223> OTHER INFORMATION: Primer

<400> SEQUENCE: 83
actagttcac ccttcttttta ctattttgtt                                        30

<210> SEQ ID NO 84
<211> LENGTH: 18
<212> TYPE: DNA

-continued

```
<213> ORGANISM: Artificial Sequence
<220> FEATURE:
<223> OTHER INFORMATION: Primer

<400> SEQUENCE: 84
tagaaggcac agtcgagg                                                 18
```